US011075910B2

(12) United States Patent
Dean et al.

(10) Patent No.: US 11,075,910 B2
(45) Date of Patent: Jul. 27, 2021

(54) SECURE SYSTEMS ARCHITECTURE FOR INTEGRATED MOTORIZED MOBILE SYSTEMS

(71) Applicant: Patroness, LLC, Nashville, TN (US)

(72) Inventors: Jered Harvey Dean, Arvada, CO (US); Barry George Dean, Franklin, TN (US); Dan Alan Preston, Bainbridge Island, WA (US)

(73) Assignee: Patroness, LLC, Brentwood, TN (US)

( * ) Notice: Subject to any disclaimer, the term of this patent is extended or adjusted under 35 U.S.C. 154(b) by 188 days.

(21) Appl. No.: 15/880,663

(22) Filed: Jan. 26, 2018

(65) Prior Publication Data
US 2019/0052637 A1    Feb. 14, 2019

Related U.S. Application Data

(60) Provisional application No. 62/612,617, filed on Dec. 31, 2017, provisional application No. 62/543,896, filed on Aug. 10, 2017.

(51) Int. Cl.
*H04L 29/06* (2006.01)
*G16H 40/67* (2018.01)
(Continued)

(52) U.S. Cl.
CPC ......... *H04L 63/0892* (2013.01); *G16H 10/65* (2018.01); *G16H 40/67* (2018.01);
(Continued)

(58) Field of Classification Search
CPC ... H04L 63/0892; H04L 63/08; H04L 63/061; H04W 12/06; H04W 12/00407;
(Continued)

(56) References Cited

U.S. PATENT DOCUMENTS 9,499,069 B2 * 11/2016 Hyde ................ B60N 2/002
10,096,228 B1 * 10/2018 Eulloqui ........... G06K 9/00892
(Continued)

FOREIGN PATENT DOCUMENTS

| EP | 3182315 A1 | 6/2017 | |
| WO | 2016110852 A2 | 7/2016 | |
| WO | WO-2016110852 A2 * | 7/2016 | ............. B60K 37/02 |

OTHER PUBLICATIONS

PCT/US2018/046059 Notification of Transmittal of International Preliminary Report on Patentability and International Preliminary Report on Patentability, dated Sep. 5, 2019, 40 pages.
(Continued)

*Primary Examiner* — Saleh Najjar
*Assistant Examiner* — Nhan Huu Nguyen
(74) *Attorney, Agent, or Firm* — Polsinelli PC

(57) ABSTRACT

Systems and methods are disclosed herein for secure communication of data between motorized mobile systems (MMS) and external devices, systems, networks, and servers. The data may include one or more of user, health, environment, and system data retrieved from one or more sensors located in, on, and around an MMS. The MMS stores and/or transmits the sensor data using secure protocols when the sensor data relates to personal information, such as personal health data, to protect the privacy of the user.

77 Claims, 31 Drawing Sheets

(51) Int. Cl.
*H04W 12/04* (2021.01)
*H04W 12/06* (2021.01)
*H04W 12/47* (2021.01)
*G16H 10/65* (2018.01)
*H04W 4/38* (2018.01)
*H04W 4/40* (2018.01)
*H04W 4/029* (2018.01)
*H04W 4/02* (2018.01)

(52) U.S. Cl.
CPC ............ *H04L 63/061* (2013.01); *H04L 63/08* (2013.01); *H04W 12/04* (2013.01); *H04W 12/06* (2013.01); *H04W 12/47* (2021.01); *H04W 4/026* (2013.01); *H04W 4/027* (2013.01); *H04W 4/029* (2018.02); *H04W 4/38* (2018.02); *H04W 4/40* (2018.02)

(58) Field of Classification Search
CPC ......... H04W 12/04; H04W 4/40; H04W 4/38; H04W 4/027; H04W 4/026; H04W 4/029; G16H 40/67; G16H 10/65
See application file for complete search history.

(56) References Cited

U.S. PATENT DOCUMENTS

| | | | |
|---|---|---|---|
| 10,212,570 B1* | 2/2019 | Ramalingam | H04L 51/18 |
| 2002/0121394 A1* | 9/2002 | Kamen | A61G 5/061 180/41 |
| 2004/0262859 A1* | 12/2004 | Turturiello | A61G 5/1089 280/5.515 |
| 2005/0041813 A1 | 2/2005 | Forest et al. | |
| 2005/0083207 A1* | 4/2005 | Smith | A61F 5/3776 340/668 |
| 2005/0151360 A1* | 7/2005 | Bertrand | F16F 9/535 280/755 |
| 2007/0038155 A1* | 2/2007 | Kelly, Jr. | A61B 5/1117 600/595 |
| 2007/0095582 A1* | 5/2007 | Stuijt | A61G 5/10 180/65.1 |
| 2007/0198850 A1* | 8/2007 | Martin | G07C 9/00087 713/186 |
| 2008/0135321 A1* | 6/2008 | Ripple | A61G 5/043 180/282 |
| 2008/0294300 A1* | 11/2008 | Ashmore | A61F 4/00 700/303 |
| 2010/0123574 A1* | 5/2010 | Yamamura | G08B 25/10 340/539.1 |
| 2012/0052469 A1* | 3/2012 | Sobel | A61B 5/087 434/262 |
| 2013/0197732 A1* | 8/2013 | Pearlman | A61G 5/1089 701/22 |
| 2013/0231800 A1* | 9/2013 | Ricci | B60W 50/0098 701/1 |
| 2014/0052319 A1* | 2/2014 | Taylor | G07C 5/008 701/22 |
| 2014/0165159 A1* | 6/2014 | Baade | H04L 63/08 726/4 |
| 2014/0210593 A1 | 7/2014 | Cattermole et al. | |
| 2014/0277888 A1* | 9/2014 | Dastoor | B60L 3/12 701/22 |
| 2014/0335902 A1 | 11/2014 | Guba et al. | |
| 2015/0183431 A1* | 7/2015 | Nanami | B60W 40/04 701/301 |
| 2015/0209207 A1* | 7/2015 | Cooper | A61G 5/14 701/49 |
| 2015/0244779 A1 | 8/2015 | Fitzgerald | |
| 2015/0268059 A1* | 9/2015 | Borghesani | H04W 4/029 701/32.3 |
| 2015/0346724 A1 | 12/2015 | Jones et al. | |
| 2015/0351981 A1* | 12/2015 | Sazonov | G01L 5/00 297/217.2 |
| 2015/0363986 A1* | 12/2015 | Hoyos | H05K 999/99 340/5.61 |
| 2016/0009169 A1* | 1/2016 | Biderman | B60L 3/0046 701/22 |
| 2016/0012721 A1* | 1/2016 | Biderman | E05B 49/006 701/117 |
| 2016/0025499 A1* | 1/2016 | Moore | G01S 19/13 701/1 |
| 2016/0052137 A1* | 2/2016 | Hyde | A61G 5/047 701/24 |
| 2016/0075177 A1* | 3/2016 | Biderman | A61B 5/6893 301/6.5 |
| 2017/0038787 A1 | 2/2017 | Baker et al. | |
| 2017/0266069 A1* | 9/2017 | Lozano | A61G 5/04 |
| 2018/0012433 A1* | 1/2018 | Ricci | B60L 53/65 |
| 2018/0042797 A1* | 2/2018 | Richter | A61G 5/041 |
| 2018/0135987 A1* | 5/2018 | Evans | A61G 5/1054 |
| 2019/0008461 A1* | 1/2019 | Gupta | A61B 5/7267 |
| 2019/0061772 A1* | 2/2019 | Prinz | A61B 5/18 |
| 2020/0121526 A1* | 4/2020 | Cooper | A61G 5/043 |

OTHER PUBLICATIONS

PCT/US2018/046059 International Search Report and Written Opinion, 24 pages, dated Oct. 22, 2018.

ANSI/IEEE Std 802.2, "IEEE Standard for Information technology—Telecommunications and information exchange between systems—Local and metropolitan area networks—Specific requirements—Part 2: Logical Link Control", The Institute of Electrical and Electronics Engineers, Inc., New York, NY, USA, ISBN 1-55937-019-X, Dec. 31, 1989, 114 pages.

ETSI European Standard EN 302 663 (V1.2.1), "Intelligent Transport Systems (ITS); Access layer specification for Intelligent Transport Systems operating in the 5 GHz frequency band", European Telecommunications Standards Institute, Sophia Antipolis, France, Reference REN/ITS-0040028, Jul. 2013, 24 pages.

ETSI Harmonized European Standard EN 302 571 (V1.2.1), "Intelligent Transport Systems (ITS); Radio commmunications equipment operating in the 5 855 MHz to 5 925 MHz frequency band; Harmonized EN covering the essential requirements of article 3.2 of the R&TTE Directive", European Telecommunications Standards Institute, Sophia Antipolis, France, Reference REN/ERM-TG37-009, Sep. 2013, 47 pages.

ETSI Technical Specification TS 102 687 (V1.1.1), "Intelligent Transport Systems (ITS); Decentralized Congestion Control Mechanisms for Intelligent Transport Systems operating in the 5 GHz range; Access layer part", European Telecommunications Standards Institute, Sophia Antipolis, France, Reference DTS/ITS-0040014, Jul. 2011, 45 pages.

ETSI Technical Specification TS 102 792 (V1.2.1), "Intelligent Transport Systems (ITS); Mitigation techniques to avoid interference between European CEN Dedicated Short Range Communication (CEN DSRC) equipment and Intelligent Transport Systems (ITS) operating in the 5 GHz frequency range", European Telecommunications Standards Institute, Sophia Antipolis, France, Reference RTS/ITS-00438, Jun. 2015, 23 pages.

IEC Std. 61851-1:2017 "Electric vehicle conductive charging system—Part 1: General requirements", the International Electrotechnical Commission, Geneva, Switzerland, ISBN 978-2-8322-3766-3, Feb. 7, 2017, 292 pages.

IEEE Std. 802.11-2016, "IEEE Standard for Information technology—Telecommunications and information exchange between systems Local and metropolitan area networks—Specific requirements—Part 11: Wireless LAN Medium Access Control (MAC) and Physical Layer (PHY) Specifications", The Institute of Electrical and Electronics Engineers, Inc., New York, NY, USA, ISBN 978-1-5044-3645-8 STDPD22369, Dec. 14, 2016, 3534 pages.

IEEE Std. 802.15.1-2005, "Wireless medium access control (MAC) and physical layer (PHY) specifications for wireless personal area networks (WPANs)", The Institute of Electrical and Electronics Engineers, Inc., New York, NY, USA, ISBN 0-7381-4707-9 SH95323, Jun. 14, 2005, 600 pages.

(56) References Cited

OTHER PUBLICATIONS

IEEE Std. 802.15.4-2015, "IEEE Standard for Low-Rate Wireless Networks", The Institute of Electrical and Electronics Engineers, Inc., New York, NY, USA, ISBN 978-1-5044-0846-2 STDPD20893, Apr. 22, 2016, 708 pages.

IEEE Std. 802.15.4q-2016, "IEEE Standard for Low-Rate Wireless Networks Amendment 2: Ultra-Low Power Physical Layer", The Institute of Electrical and Electronics Engineers, Inc., New York, NY, USA, ISBN 978-1-5044-0782-3 STD20852, Apr. 29, 2016, 52 pages.

IEEE Std. 802.15.4t-2017, "IEEE Standard for Low-Rate Wireless Networks Amendment 4: Higher Rate (2 Mb/s) Physical (PHY) Layer", The Institute of Electrical and Electronics Engineers, Inc., New York, NY, USA, ISBN 978-0-1-5044-3933-6 STDPD22524, Apr. 14, 2017, 25 pages.

IEEE Std. 802.16-2012, "IEEE Standard for Air Interface for Broadband Wireless Access Systems", The Institute of Electrical and Electronics Engineers, Inc., New York, NY, USA, ISBN 978-0-7381-7291-0 STD97266, Aug. 17, 2012, 2544 pages.

IEEE Std. 802-2014, "IEEE Standard for Local and Metropolitan Area Networks: Overview and Architecture", The Institute of Electrical and Electronics Engineers, Inc., New York, NY, USA, ISBN 978-0-7381-9219-2 STD98723, Jun. 30, 2014, 74 pages.

IEEE Std. 1003.1-2008, "IEEE Standard for Information Technology—Portable Operating System Interface (POSIX)", The Institute of Electrical and Electronics Engineers, Inc., New York, NY, USA, ISBN 978-0-7381-5798-6 STD95820, Dec. 1, 2008, 3874 pages.

IEEE Std. 1609.0-2013, "IEEE Guide for Wireless Access in Vehicular Environments (WAVE)—Architecture", The Institute of Electrical and Electronics Engineers, Inc., New York, NY, USA, ISBN 978-0-7381-8756-3 STD98459, Mar. 5, 2014, 78 pages.

IEEE Std. 1609.2-2016, "IEEE Standard for Wireless Access in Vehicular Environments—Security Services for Applications and Management Messages", The Institute of Electrical and Electronics Engineers, Inc., New York, NY, USA, ISBN 978-1-5044-0767-0 STD20841, Mar. 1, 2016, 884 pages.

IEEE Std. 1609.4-2016, "IEEE Standard for Wireless Access in Vehicular Environments (WAVE)—Multi-Channel Operation", The Institute of Electrical and Electronics Engineers, Inc., New York, NY, USA, ISBN 978-1-5044-0761-8 3TD20838, Mar. 21, 2016, 205 pages.

IEEE Std. 1609.11-2010, "IEEE Standard for Wireless Access in Vehicular Environments (WAVE)—Over-the-Air Electronic Payment Data Exchange Protocol for Intelligent Transportation Systems (ITS) ", The Institute of Electrical and Electronics Engineers, Inc., New York, NY, USA, ISBN 978-0-7381-6501-1 STD97080, Jan. 9, 2011, 62 pages.

IEEE Std. 1609.12-2016, "IEEE Standard for Wireless Access in Vehicular Environments (WAVE)—Identifier Allocations", The Institute of Electrical and Electronics Engineers, Inc., New York, NY, USA, ISBN 978-1-5044-0765-6 STD20840, Mar. 11, 2016, 39 pages.

IEEE Std. 11073-20601-2014, "IEEE Health informatics-Personal health device communication—Part 20601: Application profile—Optimized Exchange Protocol", The Institute of Electrical and Electronics Engineers, Inc., New York, NY, USA, ISBN 978-0-7381-9314-4 STD98793, Oct. 10, 2014, 253 pages.

ISO/IEC 7498-1:1994, "Information technology—Open Systems Interconnection—Basic Reference Model: The Basic Model", Geneva, Switzerland, Reference No. ISO/IEC 7498-1:1994(E), Nov. 15, 1994, 68 pages.

ISO/IEC Std. 15408-1:2009, 3rd Edition: "Information technology—Security techniques—Evaluation criteria for IT security—Part 1: Introduction and general model", the International Organization for Standardization and the International Electrotechnical Commission Joint Technical Committee, Geneva, Switzerland, Reference No. ISO/IEC 15408-1:2009(E), Dec. 15, 2009, 74 pages ISO/IEC Std. 15408-2:2008, 3rd Edition: "Information technology—Security techniques—Evaluation criteria for IT security—Part 2: Security functional components", the International Organization for Standardization and the International Electrotechnical Commission Joint Technical Committee, Geneva, Switzerland, Reference No. ISO/IEC 15408-2:2008(E), Aug. 15, 2008, 240 pages.

ISO/IEC Std. 15408-3:2008, 3rd Edition: "Information technology—Security techniques—Evaluation criteria for IT security—Part 3: Security assurance components", the International Organization for Standardization and the International Electrotechnical Commission Joint Technical Committee, Geneva, Switzerland, Reference No. ISO/IEC 15408-3:2008(E), Aug. 15, 2008, 188 pages.

ISO/IEC Std. 18092:2013, "Information technology—Telecommunications and information exchange between system—Near Field Communication—Interface and Protocol (NFCIP-1)", the International Organization for Standardization and the International Electrotechnical Commission Joint Technical Committee, Geneva, Switzerland, Reference No. ISO/IEC 18092:2013(E), Mar. 15, 2013, 52 pages.

ISO/IEC Std. 18092:2013 Technical Corrigendum 1, "Information technology—Telecommunications and information exchange between systems—Near Field Communication—Interface and Protocol (NFCIP-1)", the International Organization for Standardization and the International Electrotechnical Commission Joint Technical Committee, Geneva, Switzerland, Reference No. SO/IEC 18092:2013/Cor.1:2015(E), Jul. 15, 2015, 2 pages.

ITU-T Recommendation X.691 (2015), "Information technology—ASN.1 encoding rules: Specification of Packed Encoding Rules (PER)", International Telecommunication Union, Geneva, Switzerland, Aug. 2015, 74 pages.

SAE Std. J1772_201710, "SAE Electric Vehicle and Plug in Hybrid Electric Vehicle Conductive Charge Coupler", SAE International, Warrendale, Pennsylvania, USA, Oct. 13, 2017, 116 pages.

\* cited by examiner

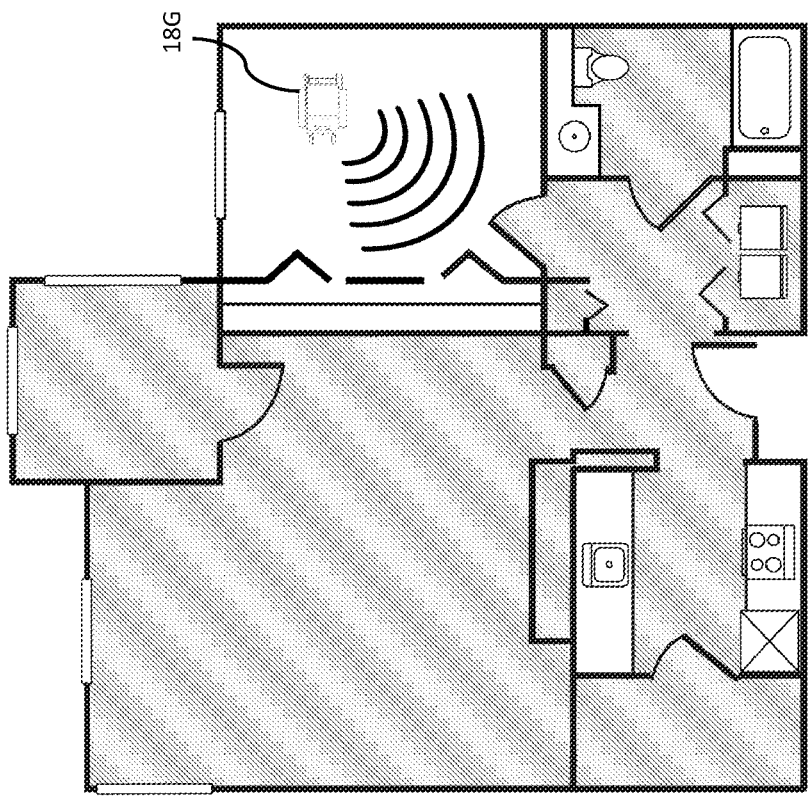
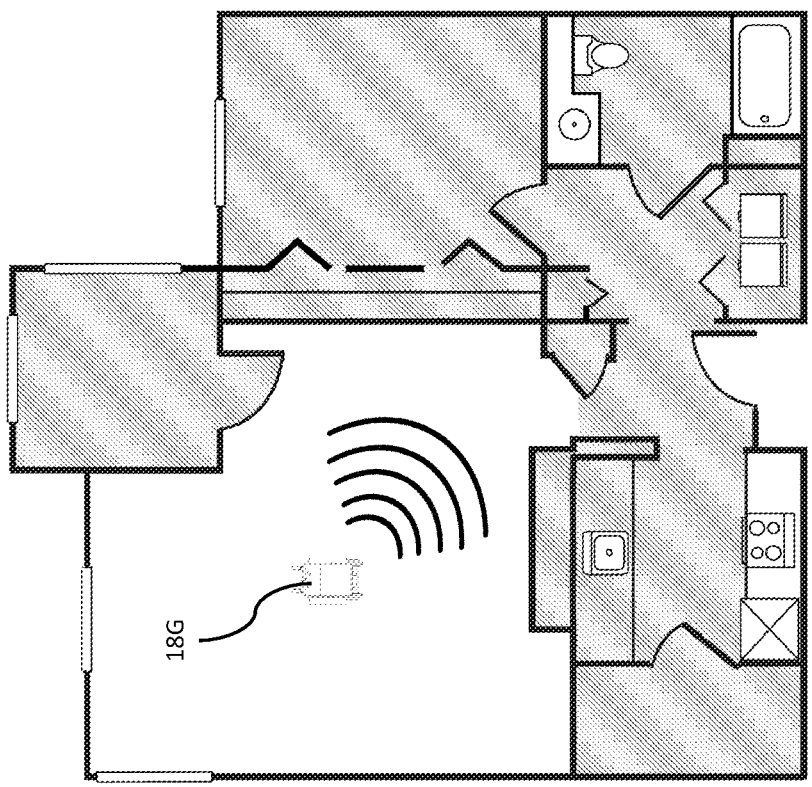
FIG. 25

SECURE SYSTEMS ARCHITECTURE FOR INTEGRATED MOTORIZED MOBILE SYSTEMS

RELATED APPLICATIONS

The present application claims priority to U.S. Provisional Patent App. No. 62/543,896, entitled Systems and Methods for Motorized Mobile Systems, filed Aug. 10, 2017, and U.S. Provisional Patent App. No. 62/612,617, entitled Systems and Methods for Enhanced Autonomous Operations of a Motorized Mobile System, filed Dec. 31, 2017, which are incorporated herein by reference in their entirety. The present application is related to U.S. patent application Ser. No. 15/880,686, entitled Federated Sensor Array for Use with a Motorized Mobile System and Method of Use, filed on the same date as the present application, U.S. patent application Ser. No. 15/880,699, entitled System and Method for Sensor Integration in Support of Situational Awareness for a Motorized Mobile, filed on the same date as the present application, all of which are incorporated herein by reference in their entirety.

INVENTORS

| | | | |
|---|---|---|---|
| Jered H. Dean | US Citizen | US Resident | Arvada, CO |
| Barry G. Dean | US Citizen | US Resident | Franklin, TN |
| Dan A. Preston | US Citizen | US Resident | Bainbridge Island, WA |

COPYRIGHT NOTICE

Contained herein is material that is subject to copyright protection. The copyright owner has no objection to the facsimile reproduction by anyone of the patent document or the patent disclosure, as it appears in the United States Patent and Trademark Office patent file or records, but otherwise reserves all rights to the copyright whatsoever. The following notice applies to the software, screenshots and data as described below and in the drawings hereto and All Rights Reserved.

FIELD

This disclosure relates generally to control systems and sensor systems for motorized mobile systems.

BACKGROUND

Drive-by-wire (DbW), steer-by-wire, or x-by-wire technology is the use of electrical or electro-mechanical systems for performing vehicle functions traditionally achieved by mechanical linkages. This technology replaces the traditional mechanical control systems with electronic control systems using electromechanical actuators and human-machine interfaces. The technology is similar to the fly-by-wire systems used in the aviation industry. Use of these "by-wire" systems began with manned aircraft, migrated to drones, as well as marine and rail operations, and are now being used in autonomous or self-driving vehicle applications. These once expensive technologies are emerging in the market as commodity products, including products with sensors, processors, integrated mobile devices, and various communication mediums, including bandwidth increases for soon to be $5^{th}$ generation (5G) wireless devices on 5G networks.

This application and co-pending applications will create and achieve safe, secure independence and a richer experience for all motorized mobile system (MMS) users. As an example of the need for improved MMSs, consider that today, with the advances in robotics and systems of systems integration, as well as medical advances that allow device integration with the human nervous system, there is a widening split between MMS users with varying physiological functionality. Some mobile chair users may have significant remaining upper body mobility and cognitive function. An example of this would be a person who does not have the use of their legs and who uses a manual mobile chair for mobility, but is otherwise able to navigate day-to-day life with minimal to no assistance. Such an individual may be able to adapt to an artificial limb, such as a leg, or an exoskeleton and reasonably be able to go about their day to day life with few restrictions. However, another example would be a user with certain health issues that greatly impacts the user's mobility and/or cognition. It is unlikely that these users will benefit from the same artificial leg or exoskeleton technologies due to their physiological condition. These users may use a motorized mobile system, such as a mobile chair.

Many mobile chair users report they are frequently frustrated by the general public's poor understanding of their abilities and needs. In general, the mobile chair is an extension of a user's body. People who use them have different disabilities and varying abilities. Some can use their arms and hands, while others can get out of their mobile chairs and walk for short distances. "Disability" is a general, medical term used for a functional limitation that interferes with a person's ability to walk, hear, learn, or utilize other physiological and/or cognitive functions of the body.

Conditions like cerebral palsy can be a sub-set of either physiological or cognitive disabilities since there are a number of sub-types classified based on specific ailments they present, resulting in varying degrees of ability. For example, those with stiff muscles have what is medically defined as spastic cerebral palsy, those with poor coordination have ataxic cerebral palsy, and those with writhing movements have athetoid cerebral palsy, each type requiring individual mobility plans.

Following are a few definitions used in this disclosure.

People with disabilities: This term represents a universe of potential conditions, including physical, cognitive, and/or sensory conditions.

Mobility disability: This term represents a condition for a person who uses a mobile chair or other MMS to assist in mobility.

User: This term refers to an individual who uses an MMS. A "user" of a mobile chair is referred to herein as a "mobile chair user".

Operator: This term refers to an individual who operates an MMS, including manual, local, and remote operation.

Caregiver: This term represents any individual that assists an MMS user. Family, friends, aides, and nurses may all be included in this category. The term "Attendant" is used synonymously with the term caregiver.

Technician: This term includes one or more of those individuals who setup, service, modify, or otherwise work technically on an MMS. These individuals may be formally licensed or may include operators and caregivers who are comfortable working with the system.

A mobile chair is essentially a chair with wheels used when walking is difficult or impossible due to illness, injury, or disability. Mobile chairs come in a wide variety to meet the specific needs of their users, including:

Manual self-propelled mobile chairs.
Manual attendant-propelled mobile chairs.
Powered mobile chairs (power-chairs).
Mobility scooters.
Single-arm drive mobile chairs.
Reclining mobile chairs.
Standing mobile chairs.
Combinations of the above.

Mobile Chairs include specialized seating adaptions and/or individualized controls and may be specific to particular activities. The most widely recognized distinction in mobile chairs is powered and unpowered. Unpowered mobile chairs are propelled manually by the user or attendant while powered mobile chairs are propelled using electric motors.

Motorized mobile chairs are useful for those unable to propel a manual mobile chair or who may need to use a mobile chair for distances or over terrain which would be fatiguing or impossible in a manual mobile chair. They may also be used not just by people with 'traditional' mobility impairments, but also by people with cardiovascular and fatigue-based conditions. A Motorized Mobile System (MMS) is a non-automobile motorized device which provides powered mobility to one or more users, including such systems as powered mobile chairs, mobility scooters, electronic conveyance vehicles, riding lawn mowers, grocery carts, all-terrain vehicles (ATVs), golf carts, and other recreational and/or medical mobility systems, but excludes automobiles (passenger cars, trucks, passenger buses, and other passenger or property transporting motorized vehicles intended for licensed operation on state and national highways). For the sake of clarity, a mobile chair MMS is described herein as an exemplary embodiment; however, it should be clear that the same or similar systems and methods may be applied to other MMS embodiments.

A mobile chair MMS is generally four-wheeled or six-wheeled and non-folding. Four general styles of mobile chair MMS drive systems exist: front, center, rear, and all-wheel drive. Powered wheels are typically somewhat larger than the trailing/castering wheels, while castering wheels on a motorized chair are typically larger than the casters on a manual chair. Center wheel drive mobile chair MMSs have casters at both front and rear for a six-wheel layout and are often favored for their tight turning radii. Front wheel drive mobile chair MMSs are often used because of their superior curb-climbing capabilities. Power-chair chassis may also mount a specific curb-climber, a powered device to lift the front wheels over a curb of 10 cm or less.

Mobile chair MMSs are most commonly controlled by arm-rest mounted joysticks which may have additional controls to allow the user to tailor sensitivity or access multiple control modes, including modes for the seating system. For users who are unable to use a hand controller, various alternatives are available, such as sip-and-puff controllers, worked by blowing into a sensor. In some cases, a controller may be mounted for use by an aide walking behind the chair rather than by the user. Capabilities include turning one drive-wheel forward while the other goes backward, thus turning the mobile chair within its own length.

The seating system on a mobile chair MMS can vary in design, including a basic sling seat and backrest, optional padding, comfortable cushions, backrest options, and headrests. Many companies produce aftermarket seat, back, leg, and head rest options which can be fitted onto mobile chair MMSs. Some seat, back, leg, and head rests are produced to aid with increased need for stability in the trunk or for those at increased risk of pressure sores from sitting. Leg rests may be integrated into the seating design and may include manual and/or powered adjustment for those users who want or need to vary their leg position. Mobile chair MMSs may also have a tilt-in-space, or reclining facility, which is particularly useful for users who are unable to maintain an upright seating position indefinitely. This function can also help with comfort by shifting pressure to different areas over time, or with positioning in a mobile chair when a user needs to get out of the chair or be hoisted.

Most mobile chairs are crash tested to ISO standards 7176 and 10542. These standards mean that a mobile chair can be used facing forward in a vehicle if the vehicle has been fitted with an approved tie down or docking system for securing the mobile chair and a method of securing the occupant to the mobile chair.

Rehabilitation engineering is the systematic application of engineering sciences to design, develop, adapt, test, evaluate, apply, and distribute technological solutions to problems confronted by individuals with disabilities. Current practitioners of rehabilitation engineering are often forced to work with limited information and make long term decisions about the technologies to be used by an individual on the basis of a single evaluation; a snapshot in time. Under current best-case conditions, rehabilitation engineering practitioners work closely in a long-term relationship with their clients to follow-up and readjust assistive technology systems on a regular basis. However, even in these situations, they are often working with limited information and only at periodic intervals.

What is needed is an evolution of existing motorized mobile systems (MMSs) to consider the users' abilities, needs, and health, with the goal of a safe, secure, and social independence. To accomplish this, systems and methods are disclosed herein comprising: integrated software and hardware systems, sensors for situational awareness, sensors for user monitoring, communications between users and caregivers, users and other users, and users and the "cloud", and human machine interfaces (HMIs) designed for users with a variety of physiological and cognitive conditions. The systems and methods disclosed herein are based on new underlying technologies, architectures, and network topologies that support the evolution of the MMS.

SUMMARY

Four co-pending-applications disclose various aspects of improved MMSs. All four are disclosed as related above and each incorporates by reference herein in the entirety of the other applications in full.

The application entitled "Secure Systems Architecture for Motorized Mobile Systems," relates to systems and methods for implementing a control system onboard an MMS capable of securely communicating with and utilizing external systems. This may include integrating external devices and user health monitoring sensors with an off the shelf (OTS) or custom MMS. Integration of a smart device, such as a smart phone or tablet, with an OTS or custom MMS is another example. Today, most smart devices contain a host of applications and sensors, including one or more of image capturing devices, rate and acceleration sensors, gyroscopes, global positioning system (GPS) receivers, biometric sensors, iris scanners, fingerprint scanners, and facial recognition software. Other sensors are possible. A secure architecture for an MMS controller is disclosed in support of device integration and data security with a focus on extensibility.

The application entitled "Federated Sensor Array for Use with a Motorized Mobile System and Method of Use"

discloses the integration of non-contact sensors and control logic into an MMS controller. The federated sensors have overlapping sensing fields, generally operate independently, and report certain data relevant to navigation and stability which is then used by the MMS controller. Motor, seat, and auxiliary controllers may be hosted in the MMS controller along with the federated sensor logic. The integration of these systems and applications into an MMS lays the foundation for situational awareness (SA).

Situational awareness is the ability to be cognizant of oneself in a given space. It is an organized knowledge of objects and state kinematics in relation to oneself in a given space or scenario. Situational awareness also involves understanding the relationship of these objects when there is a change of position or kinematic state. The goal is to integrate this data into the MMS and use it to support a richer, safer, and more independent experience for the user.

The application entitled "System and Methods for Sensor Integration in Support of Situational Awareness for a Motorized Mobile System" further discloses the integration of new sensor technologies in support of a deeper and richer situational awareness for the user. These new systems use the data generated about the user, the environment, targets in the environment, and the user's relationship to them. This information may be generated from one or more sources and include data from non-contact sensors, like radar, optical, laser, and ultrasonic sensors. These non-contact sensors can generate data about the environment, including range measurements, bearing measurements, target classification, and target kinematics. The new sensors provide a much richer set of data about the environment.

The federated system uses a single type of sensor that generates a single report (i.e. a communication with or identifying data sensed by the sensor) with what is called a single mode variance, where each sensor has distinct capabilities and one or more fixed errors inherent to the sensor. Ultra-sonic sensors have better range determination than cross range position determination, for instance. In an example, using data from a different type of sensor, a good cross range report can be generated, but with poor down range determination. In this evolving system, the best of two (or more) separate reports may be combined. This is referred to as a dual mode variance.

The application entitled "System and Methods for Enhanced Autonomous Operations of a Motorized Mobile System" discloses the implementation of advanced filtering techniques and sensor fusion in support of situational awareness and autonomy. Adding more sensors to a federation of sensors increases expense, weight, and power consumption. Integration and use of sensor fusion (e.g. using different types of sensors in one system) and advanced filtering techniques improves the information the MMS controller uses to track the user and environment, while reducing complexity and cost when compared to a federated approach. Decision logic consisting of data association techniques, track and target management, handling out of sequence measurements, and sensor frame management are all building blocks for this leap in system capability.

In this enhanced system, raw data is received and "filtered", or as is known in the art fused, with other data related to the MMS user and their activities while navigating in the environment. The other data may include certain biometric data, user inputs, and user activities. Filtering and state estimation are some of the most pervasive tools of engineering. In some embodiments, a model may be used to form a prediction of a state into the future, followed by an observation of the state or actual measurement of the expectation. A comparison of the predicted state and the measured state is then made. If the observations made are within the predicted measurements, the model may be adjusted by reducing the covariance of the next measurement, thereby increasing system confidence. If the observations are outside of the predicted measurements, the model may be adjusted to increase the covariance of the next measurement, thereby decreasing system confidence.

In this enhanced system, the MMS is fully aware of its environment and can travel safely wherever the user wishes to go, within reason. Moreover, the MMS may learn to anticipate the needs of the user. The result is a user experience that is safe, secure, and independent, based on the user's base abilities and current condition.

Other systems may be integrated to improve user experience. As a non-limiting example, augmented reality (AR) may be included. Augmented reality is a live direct or indirect view of a physical, real-world environment where the elements are augmented (or supplemented) by computer-generated sensory input. The input can be sound, smell, or graphics. It is related to a more general concept called computer-mediated reality, in which a view of reality is modified, possibly even diminished rather than augmented, by a computer. As a result, the technology functions by enhancing one's current perception of reality. Virtual Reality (VR) is another technology that may be integrated to improve user experience. By contrast, VR replaces the real world with a simulated one. Augmentation is conventionally in real time and in semantic context with environmental elements, such as sports scores on TV during a match. However, VR refers to computer technologies that use VR headsets, sometimes in combination with physical spaces or multi-projected environments, to generate realistic images, sounds, and other sensations that simulate a user's physical presence in a virtual or imaginary environment.

Applicant(s) herein expressly incorporate(s) by reference all of the following materials identified in each paragraph below. The incorporated materials are not necessarily "prior art".

ISO/IEC 15408-1:2009, 3rd Edition: "Information technology—Security techniques—Evaluation criteria for IT security—Part 1: Introduction and general model".

ISO/IEC 15408-2:2008, 3rd Edition: "Information technology—Security techniques—Evaluation criteria for IT security—Part 2: Security functional components".

ISO/IEC 15408-3:2008, 3rd Edition: "Information technology—Security techniques—Evaluation criteria for IT security—Part 3: Security assurance components".

802.11-2016: "IEEE Standard for Information technology—Telecommunications and information exchange between systems Local and metropolitan area networks—Specific requirements—Part 11: Wireless LAN Medium Access Control (MAC) and Physical Layer (PHY) Specifications".

1609.0-2013: "IEEE Guide for Wireless Access in Vehicular Environments (WAVE)—Architecture".

1609.2-2016: "IEEE Standard for Wireless Access in Vehicular Environments—Security Services for Applications and Management Messages".

1609.4-2016: "IEEE Standard for Wireless Access in Vehicular Environments (WAVE)—Multi-Channel Operation".

1609.11-2010: "IEEE Standard for Wireless Access in Vehicular Environments (WAVE)—Over-the-Air Electronic Payment Data Exchange Protocol for Intelligent Transportation Systems (ITS)".

1609.12-2016: "IEEE Standard for Wireless Access in Vehicular Environments (WAVE)—Identifier Allocations".

ETSI EN 302 663 (V1.2.1): "Intelligent Transport Systems (ITS); Access layer specification for Intelligent Transport Systems operating in the 5 GHz frequency band."

ETSI EN 302 571 (V1.2.1): "Intelligent Transport Systems (ITS); Radiocommunications equipment operating in the 5 855 MHz to 5 925 MHz frequency band; Harmonized EN covering the essential requirements of article 3.2 of the R&TTE Directive".

ETSI TS 102 792 (V1.2.1): "Intelligent Transport Systems (ITS); Mitigation techniques to avoid interference between European CEN Dedicated Short Range Communication (CEN DSRC) equipment and Intelligent Transport Systems (ITS) operating in the 5 GHz frequency range".

IEEE 802-2014: "IEEE Standard for Local and Metropolitan Area Networks: Overview and Architecture".

ANSI/IEEE Std 802.2 (1998): "IEEE Standard for Information technology—Telecommunications and information exchange between systems—Local and metropolitan area networks—Specific requirements—Part 2: Logical Link Control".

ISO/IEC 7498-1:1994: "Information technology—Open Systems Interconnection—Basic Reference Model: The Basic Model".

ITU-T Recommendation X.691 (2015): "Information technology—ASN.1 encoding rules: Specification of Packed Encoding Rules (PER)".

ETSI TS 102 687 (V1.1.1): "Intelligent Transport Systems (ITS); Decentralized Congestion Control Mechanisms for Intelligent Transport Systems operating in the 5 GHz range; Access layer part".

IEEE 1003.1-2008: "IEEE Standard for Information Technology—Portable Operating System Interface (POSIX (R))".

IEEE 802.15.1-2005: "Wireless medium access control (MAC) and physical layer (PHY) specifications for wireless personal area networks (WPANs)".

IEEE 802.15.4-2015: "IEEE Standard for Low-Rate Wireless Networks".

ISO/IEC 18092:2013: "Information technology—Telecommunications and information exchange between systems—Near Field Communication—Interface and Protocol (NFCIP-1)".

IEEE 802.16-2012: "IEEE Standard for Air Interface for Broadband Wireless Access Systems".

ISO/IEEE 11073-20601-2014: "IEEE Health informatics—Personal health device communication—Part 20601: Application profile—Optimized Exchange Protocol".

Bluetooth SIG: "Bluetooth Core Specification", v5.0.

If it is believed that any of the above-incorporated material constitutes "essential material" within the meaning of 37 CFR 1.57(d)(1)-(3), applicant(s) reserve the right to amend the specification to expressly recite the essential material that is incorporated by reference as allowed by the applicable rules.

Aspects and applications presented here are described below in the drawings and detailed description. Unless specifically noted, it is intended that the words and phrases in the specification and the claims be given their plain and ordinary meaning to those of ordinary skill in the applicable arts. The inventors are aware that they can be their own lexicographers if desired. The inventors expressly elect, as their own lexicographers, to use only the plain and ordinary meaning of terms in the specification and claims unless they clearly state otherwise and expressly set forth the "special" definition of that term. Absent such clear statements of intent to apply a "special" definition, it is the inventors' intent and desire that the plain and ordinary meaning to the terms be applied to the interpretation of the specification and claims.

Further, the inventors are informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f) to define the systems, methods, processes, and/or apparatuses disclosed herein. To the contrary, if the provisions of 35 U.S.C. § 112(f) are sought to be invoked to define the embodiments, the claims will specifically and expressly state the exact phrases "means for" or "step for" and will also recite the word "function" (i.e., will state "means for performing the function of . . . "), without also reciting in such phrases any structure, material, or act in support of the function. Thus, even when the claims recite a "means for performing the function of . . . " or "step for performing the function of . . . ", if the claims also recite any structure, material, or acts in support of that means or step then it is the clear intention of the inventors not to invoke the provisions of 35 U.S.C. § 112(f). Moreover, even if the provisions of 35 U.S.C. § 112(f) are invoked to define the claimed embodiments, it is intended that the embodiments not be limited only to the specific structures, materials, or acts that are described in the preferred embodiments, but in addition, include any and all structures, materials, or acts that perform the claimed function as described in alternative embodiments or forms, or that are well known present or later-developed equivalent structures, materials, or acts for performing the claimed function.

BRIEF DESCRIPTION OF THE DRAWINGS

A more complete understanding of the systems, methods, processes, and/or apparatuses disclosed herein may be derived by referring to the detailed description when considered in connection with the following illustrative figures. In the figures, like-reference numbers refer to like-elements or acts throughout the figures.

FIG. 25 depicts a mobile chair S-MMS communicating with in-home smart automation devices.

Figure 1:
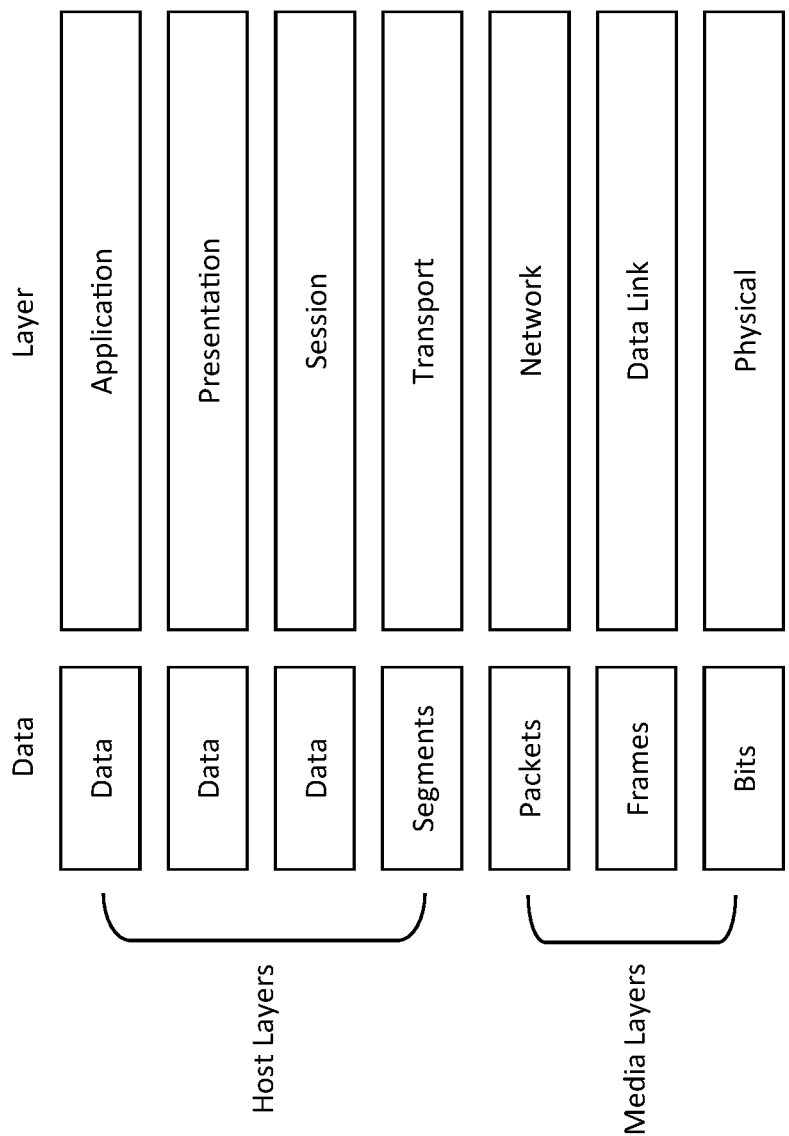
FIG. 1 depicts the Open Systems Interconnection (OSI) model.

Elements and acts in the figures are illustrated for simplicity and have not necessarily been rendered according to any particular sequence or embodiment.

DETAILED DESCRIPTION

In the following description, and for the purposes of explanation, numerous specific details, process durations, and/or specific formula values are set forth in order to provide a thorough understanding of the various aspects of exemplary embodiments. However, it will be understood by those skilled in the relevant arts that the apparatus, systems, and methods herein may be practiced without all of these specific details, process durations, and/or specific formula values. Other embodiments may be utilized and structural and functional changes may be made without departing from the scope of the apparatus, systems, and methods herein. It should be noted that there are different and alternative configurations, devices, and technologies to which the disclosed embodiments may be applied. The full scope of the embodiments is not limited to the examples that are described below.

In the following examples of the illustrated embodiments, references are made to the accompanying drawings which form a part hereof, and in which is shown by way of illustration various embodiments in which the systems, methods, processes, and/or apparatuses disclosed herein may be practiced. It is to be understood that other embodiments may be utilized and structural and functional changes may be made without departing from the scope.

Systems and methods are disclosed for the implementation of a secure systems architecture for integrated motorized systems including non-automobile motorized mobile systems (MMS). For the purposes of this disclosure, automobiles are defined as passenger cars, trucks, passenger buses, and other passenger or property transporting motorized vehicles intended for licensed operation on state and national highways. A software architecture represents a collection of components that accomplish a specific function or set of functions. In other words, an architecture is focused on organizing components to support specific functionality. This organization of functionality is often referred to as grouping components into "areas of concern." A goal of this disclosure, and the others referenced above, is to create systems that adhere to engineering principles, promote usability, and promote extendibility, while minimizing costs and maintenance requirements.

A first consideration in the development of a system architecture is selection of a type of operating system (OS). There are two primary choices: non-real-time OS (NRTOS) and real-time OS (RTOS). An RTOS is an OS intended to serve applications that process data in real-time. An RTOS is either event driven or time sharing. An event driven RTOS switches between tasks based on their priorities, while a time sharing RTOS switches tasks based on clock interrupts. Independent of type, RTOSs are fairly consistent in the amount of time they take to accept and complete a task. The variability in processing time is generally referred to as jitter. The amount of jitter defines the RTOS as either hard or soft, where a hard RTOS has less jitter than a soft one. Soft RTOSs are capable of meeting deadlines, whereas hard RTOSs are not. Life, health, independence, and safety applications are typically a blending of soft and hard RTOS attributes.

Latency is a key factor in an RTOS, including thread switching latency and interrupt latency. An RTOS is valued more for how quickly or how predictably it can respond than for the amount of work it can perform in a given period of time. RTOSs are frequently dedicated to a narrow set of applications. An RTOS that has an advanced algorithm for scheduling, or has scheduling flexibility, enables a wider computer-system orchestration of process priorities.

The National Institute of Standards and Technology (NIST) developed a series of standards based on what is termed an Evaluation Assurance Level (EAL). The score is based on certain criteria ranging from EAL1 through EAL7 of a software/OS product or system. The numerical grade is assigned following the completion of a Common Criteria (CC) security evaluation. The increasing assurance levels reflect added assurance requirements that must be met to achieve a CC certification. The CC for Information Technology Security Evaluation is an international standard, ISO/IEC 15408, herein incorporated by reference in its entirety.

Common Criteria is a framework in which computer system users can specify their security functional and assurance requirements (SFRs and SARs, respectively) through the use of Protection Profiles (PPs). Product security attributes may be evaluated against the Common Criteria to determine if they meet vendor claims. Common Criteria provides assurance that the process of specification, implementation, and evaluation of a computer security product has been conducted in a rigorous, standard, and repeatable manner at a level that is commensurate with the target environment for use.

The intent of the higher levels of EAL is to provide higher confidence that a system's principal security features are reliably implemented. To achieve a particular EAL, the system must meet specific assurance requirements. Most of these requirements involve design documentation, design analysis, functional testing, or penetration testing. The higher EALs involve more detailed documentation, analysis, and testing than the lower ones. The EAL number assigned to a certified system indicates that the system completed all requirements for that level. The EAL is indicative of what level a system was tested to; it does not measure the security of the system itself.

Although every product and system must fulfill the same assurance requirements to achieve a particular level, they do not have to fulfill the same functional requirements. Assurance levels are:

EAL1: Functionally Tested
EAL2: Structurally Tested
EAL3: Methodically Tested and Checked
EAL4: Methodically Designed, Tested, and Reviewed
EAL5: Semi-formally Designed and Tested
EAL6: Semi-formally Verified Design and Tested
EAL7: Formally Verified Design and Tested Other considerations for life health and safety applications are known as the Development Assurance Level (DAL) and Item Development Assurance Level (IDAL). The IDAL is determined by examining the effects of a failure condition in the system. Failure conditions are categorized by their effects on the primary user. These include:

Catastrophic—Error or loss of critical function required to operate.
Hazardous—Failure has a large negative impact on safety or performance.
Major—Failure is significant, but has a lesser impact than a Hazardous failure.
Minor—Failure is noticeable, but has a lesser impact than a Major failure.
No Effect—Failure has no impact.

Assurance levels alone are not intended to guarantee software safety attributes. Safety requirements must be demonstrated with objective evidence typically addressed in a software safety plan.

Another design consideration is for the "portability" of source code developed for applications, drivers, and services. Code requirements should be able to implement rapidly between systems and devices for the product or application developer. One approach to increase portability is the use of a wrapper, with a private application programming interface (API) inward and a public API outward. One such wrapper supports the Portable Operating System Interface (POSIX). POSIX standards IEEE 1003.1 are a family of standards specified by the IEEE for maintaining compatibility between operating systems and hardware, herein incorporated by reference in their entirety. POSIX defines the API, along with command line shells and utility interfaces for software compatibility with variants of Unix and other operating systems. Unix was selected as the basis for a standard system interface partly because it was "manufacturer-neutral."

Motorized mobile systems may often operate around other vehicles. Therefore, it is important for MMSs and other vehicles to be able to communicate with each other for increased safety and reduced accidents. Communication standards were developed to support and enhance communications vehicle-to-vehicle (V2V) or vehicle-to-infrastructure (V2I). The standards define an architecture and a complementary standardized set of services and interfaces that collectively enable secure V2V and V2I wireless communications. Together, these standards provide the foundation for a broad range of applications in the transportation environment, including vehicle safety, automated tolling, enhanced navigation, traffic management, and many others. Recently, another standard was adopted as IEEE 1609 for Wireless Access in Vehicular Environments (WAVE). The European Telecommunications Standards Institute (ETSI) Technical Committee Intelligent Transport System (ITS) developed and adopted a related set of standards collectively called the ITS-G5. The WAVE and ITS-G5 standards are herein incorporated by reference in their entirety.

Motorized mobile systems may often operate around Internet of Things (IoT) devices. The IoT is defined as a network of physical devices and other items embedded with electronics, software, sensors, actuators, and network connectivity which enable these objects to collect and exchange data. Communication with surrounding IoT devices is, therefore, important for MMSs for increased functionality (e.g. the ability to cause action of IoT actuators) and situational awareness (e.g. the ability to access data from remote sensors). A single communication standard for IoT has not yet coalesced. The most popular wireless communication/transport layers currently in use by IoT devices include:

Bluetooth.
IEEE 802.11 based Wi-Fi communication.
multiple low-rate wireless personal area networks (LR-WPANS) based on IEEE 802.15.4 including ZigBee, MiWi, and Wireless HART.
near field communications (NFC) protocol based on ISO/IEC 18092,
cellular.
IEEE 802.16 based WiMAX communication.

These common standards are herein incorporated by reference in their entirety. IoT devices may use IPv6 internet layer protocol for packet-switched networks to deliver messages over one of the communication/transport layers listed previously in a variety of formats. Message Queuing Telemetry Transport (MQTT) protocol is a publish/subscribe messaging model that may be used to deliver data within this framework. MQTT is a popular IoT option because of its a small code footprint and limited network bandwidth needs. Other alternatives are available and may be used based on the data rate, communication range, and power consumption requirements of a particular IoT device.

The National Institute of Health reports that more individuals are moving to home healthcare. It is anticipated that this is especially true of MMS users and will necessitate the transmission and/or storage of healthcare data on user devices. In some embodiments, wireless devices may be integrated with an MMS and a user's health data may be sent over wireless networks. Health data may include one or more of user medical data and/or MMS data items, such as raw sensor data, conclusions data, patient measurements, weight, temperature, heart rate, pulse, respiratory rate, blood pressure, wetness, sight, hearing, reaction time, pain status, emotional state, orientation, location, event, state, and action. Wireless devices used on or in connection with the MMS herein may communicate using one or more of cellular, 802.11, Wi-Fi, 802.15, Bluetooth, Bluetooth Low Energy (BLE), 802.20, WiMAX, or other wireless communication standards or methods. For this type of service or application, certain standards will need to be upheld to protect user identity, security, and data. One such standard is the Health Insurance Portability and Accountability Act (HIPPA). HIPAA sets the standard for protecting sensitive user data. Any product or service that deals with protected health information (PHI) must ensure that all the required physical, network, and process security measures are in place and followed. This includes covered entities, anyone who provides treatment, payment, and operations in healthcare, and anyone with access to patient information and provides support in treatment. Subcontractors and business associates must also be in compliance with HIPAA.

The HIPAA Privacy Rule addresses the saving, accessing, and sharing of medical and personal information of any individual, while the HIPAA Security Rule more specifically outlines security standards to protect health data created, received, maintained, or transmitted electronically, also known as electronic PHI (ePHI). Anyone hosting ePHI data with a HIPAA compliant hosting provider must have certain administrative, physical, and technical safeguards in place, according to the U.S. Department of Health and Human Services. The physical and technical safeguards are most relevant to services provided by the HIPAA compliant host as listed below, with detail on what constitutes a HIPAA compliant data center.

Physical safeguards include limited facility access and control. All HIPAA compliant entities must have policies about use and access to workstations and electronic media. This includes transferring, removing, disposing, and re-using electronic media and ePHI. Technical safeguards require access control to allow only authorized personnel to access ePHI. Access control may include the use of unique user IDs, biometric login, authentication, emergency access procedures, automatic log off, and encryption and decryption, among others.

Audit reports and tracking logs should be implemented to track activity on hardware and software. These reports are useful in pinpointing the source(s) of any security violations or failures. Technical policies may also cover integrity measures put in place to confirm that ePHI has not been damaged. It is important to have Information technology (IT) disaster recovery and offsite backup measures in place to ensure that any electronic media errors or failures can be repaired and ePHI can be recovered accurately and intact.

Network security is another technical safeguard required of HIPAA compliant hosts to protect against unauthorized access of ePHI from methods of transmitting data, including Internet and private networks. Use of secure connections is required to support the secure storage and secure transmission of personal health data. A supplemental act was passed in 2009 called The Health Information Technology for Economic and Clinical Health (HITECH) Act which supports the enforcement of HIPAA requirements by raising the penalties of health organizations that violate HIPAA Privacy and Security Rules. The HITECH Act was formed in response to health technology development and increased use, storage, and transmittal of ePHI.

Countries, companies, and individuals around the world are looking for better ways to monitor health data as a growing percentage of the population is requiring medical care, both because of the changing demographics and the incidence of long-term chronic disease. This is reflected in a growing demand for connected health devices where user data can be collected by medical institutions and/or by individuals. As the use of these devices increases, along with the volume of data produced, it becomes increasingly important to ensure interoperability between devices so that similar devices connect and transfer data in a standard way.

Health device manufacturers may use Bluetooth wireless technology for a secure and reliable connection. Until recently, Bluetooth technology, as defined in the Bluetooth Core Specification, provided a wireless link, but underlying data protocols and formats were proprietary. Agreement was lacking over the best profile on which to base these underlying layers. Most devices used serial port profile (SPP) to emulate a standard RS-232 (EIA-232) serial cable, but DUN, FAX, PAN, and HID have also been put to use. In order for a consumer mass market in health and fitness devices to evolve, an interoperable wireless standard was needed.

The Bluetooth Special Interest Group (SIG) established a Medical Devices Working Group (MED WG). This group developed a profile to provide for interoperability between health devices and data sources (such as blood pressure meters, weighing scales, and thermometers) and health device sinks (such as personal computers (PCs), personal data assistants (PDAs), mobile phones, tablets, wearable computing devices, and displays) from different manufacturers. The Health Device Profile (HDP) and the Multi-Channel Adaptation Protocol (MCAP) together fulfill this need. The Bluetooth HDP defines the underlying wireless connection and protocol. It operates in conjunction with the ISO/IEEE 11073-20601 Personal Health Data Exchange Protocol (PHDEP) and associated device specialization specifications to provide application level interoperability for a wide variety of personal health devices. The Bluetooth Core Specification and ISO/IEEE 17073-20601 are herein incorporated by reference in their entirety.

Bluetooth Low Energy (BLE) was introduced in the Bluetooth 4.0 core specification by the Bluetooth SIG. It provides low energy demand, low bandwidth communication and is widely adopted by internet of things sensors and devices. Bluetooth Low Energy is an extremely flexible framework that can enable open broadcasting of data (beacon functionality) and developer configuration. It is less mature than classical Bluetooth. The Generic Attributes (GATT) define a common data structure that is exposed to connected BLE devices. While the HDP and MCAP are not incorporated in BLE, methods and services have been incorporated into GATT which support the transmission of ePHI, such as heart rate and temperature. When configured as a point-to-point device (i.e. not broadcasting), encrypted, and using GATT, a BLE connection provides application level interoperability for a wide variety of person health devices. For the purpose of this disclosure, unless explicitly stated, the term Bluetooth is meant to generically encompass classical or low energy Bluetooth embodiments.

Regarding deployment of the system architecture disclosed onto a physical electronic system, several standards exist depending on the MMS market being considered. As a non-limiting example, in the case of electrically powered mobile chair and scooter MMSs, existing standards such as the ISO 7176 series and EN12184 set electrical control system requirements and tests that are to be met. These requirements include items such as hardware fault tolerance levels, safe-failure expectations, failure mode analysis requirements, and related tests. For the purpose of this disclosure, and in some embodiments, the architecture disclosed will be deployed on a standards compliant physical system taking appropriate steps to ensure functional safety, such as lock-step processors and other best practices for critical health and safety applications.

FIGS. 2-31 disclose architectures for a Smart Motorized Mobile System (S-MMS). This new S-MMS architecture supports non-automobile motorized devices which provide powered mobility to one or more users, including such systems as powered mobile chairs, mobility scooters, electronic conveyance vehicles, riding lawn mowers, grocery carts, ATVs, golf carts, off-road vehicles, and other recreational and/or medical mobility systems, but excludes automobiles (cars, trucks, buses, and other passenger or property transporting motorized vehicles intended for operation on highways). A non-limiting, illustrative example of a motorized mobile chair is used in the disclosure. As an introduction to the evolution and growth of the system, all of the discussion above is embraced, yielding an architecture geared to grow with the availability of certain technologies, technology costs and availability, infrastructure build out, and demand.

Some embodiments of the S-MMS architecture(s) of the present disclosure and related applications may be referred to as separate generations based on different functionality. While these generations are discussed as separate embodiments, one or more aspects of one or more generations may be combined to form other control systems not explicitly disclosed herein (or in the related co-pending applications). The generations are as follows: Generation 0 (Gen 0), Generation I (Gen I), Generation II (Gen II), and Generation III (Gen III).

The motorized mobile systems (MMS) in existence today are referred to herein as Generation 0 (Gen 0). This existing MMS has a user interface and a limited control system. Gen 0 is basically hosted in (e.g. processed by) a controller with a Human Machine Interface (HMI) typically consisting of a joystick, tactile surface array, sip and puff type array, or similar interface. In some embodiments, the HMI may further include touch screens, voice command interfaces, and audible indicators, or be replaced by, a brain machine interface (BMI). The joystick receives input indicating a direction for movement, the command is generated, and control instructions are sent to the motor controller, which responds with a preconfigured response. The control instructions may include a change in state or an adjustment of an operating parameter. The preconfigured response may include taking operational control of steering, starting the MMS, or stopping the MMS. The state of the art for this type of system is to provide extremely simple control instructions and open loop limits on the MMS. Open loop systems lack the ability for self-correcting actions. An example of an open loop limit currently in use on MMSs is to cut the maximum MMS speed to a predetermined set point if the user raises the seat position above a certain threshold. The motor controller responds directly to the user input regardless of the environment proximate to the MMS. A new user may have a learning curve to master before they can confidently maneuver close to people, objects, or in confined environments.

The present application and one or more related applications disclose improved generations of S-MMS architectures, including Generations I-III architectures. Generation I is an embodiment for a group of sensors reporting to a controller for the S-MMS. Generation II embodiments further include consideration for scanning and/or image sensors operating in overlapping regions. Using a sensor with good down range error, and a second sensor with good cross range error, a Generation II system embodiment can coordinate reports in real-time, associate them, and take the best measurements in an ability to make the situational awareness picture more accurate. This use of more than one sensor is typically referred to as dual mode variance. Generation III is an embodiment for a multi-generation controller architecture and logic. In some embodiments, a Generation III system may host one or more of the previous generations or combinations thereof. Generation III systems go beyond dual mode variance to true sensor fusion.

In the Generation I-III systems, the S-MMS controller may include one or more processors (hardware), application-specific integrated circuits, and/or field-programmable gate arrays. Control signals may be via wired or wireless communications, and comprised of digital and/or analog signals.

The Open Systems Interconnection (OSI) model characterizes and standardizes the communication functions of a computing system without regard to the underlying internal structure and technology which increases interoperability of differing systems that adhere to it. A typical OSI model is partitioned into seven abstraction layers, though other models exist with differing numbers of layers. Each layer serves the layer above it and is served by the layer below it. The OSI model depicted in FIG. 1 comprises seven layers with Layer 1 on the bottom up to Layer 7 at the top.

Layer 1 is a physical layer which allows for the transmission and reception of raw bit data streams over a physical medium. It defines the electrical and physical specifications of a data connection. Layer 2 is a data link layer which allows for the reliable transmission of data frames between nodes connected by a physical layer (Layer 1). Layer 3 is a network layer which allows for structuring and management of a network, including addressing, routing, and traffic control. Layer 4 is a transport layer which allows for reliable transmission of data across a network. Layer 5 is a session layer which allows for the management of communication sessions over a network. Layer 6 is a presentation layer which translates data between a network and an application. Layer 7 is an application layer which includes resource sharing and remote file access. The application layer, Layer 7, is the layer closest to the end user—both the application layer and the end user interact with an application directly. Some functions operate across two or more of the layers.

Figure 2:
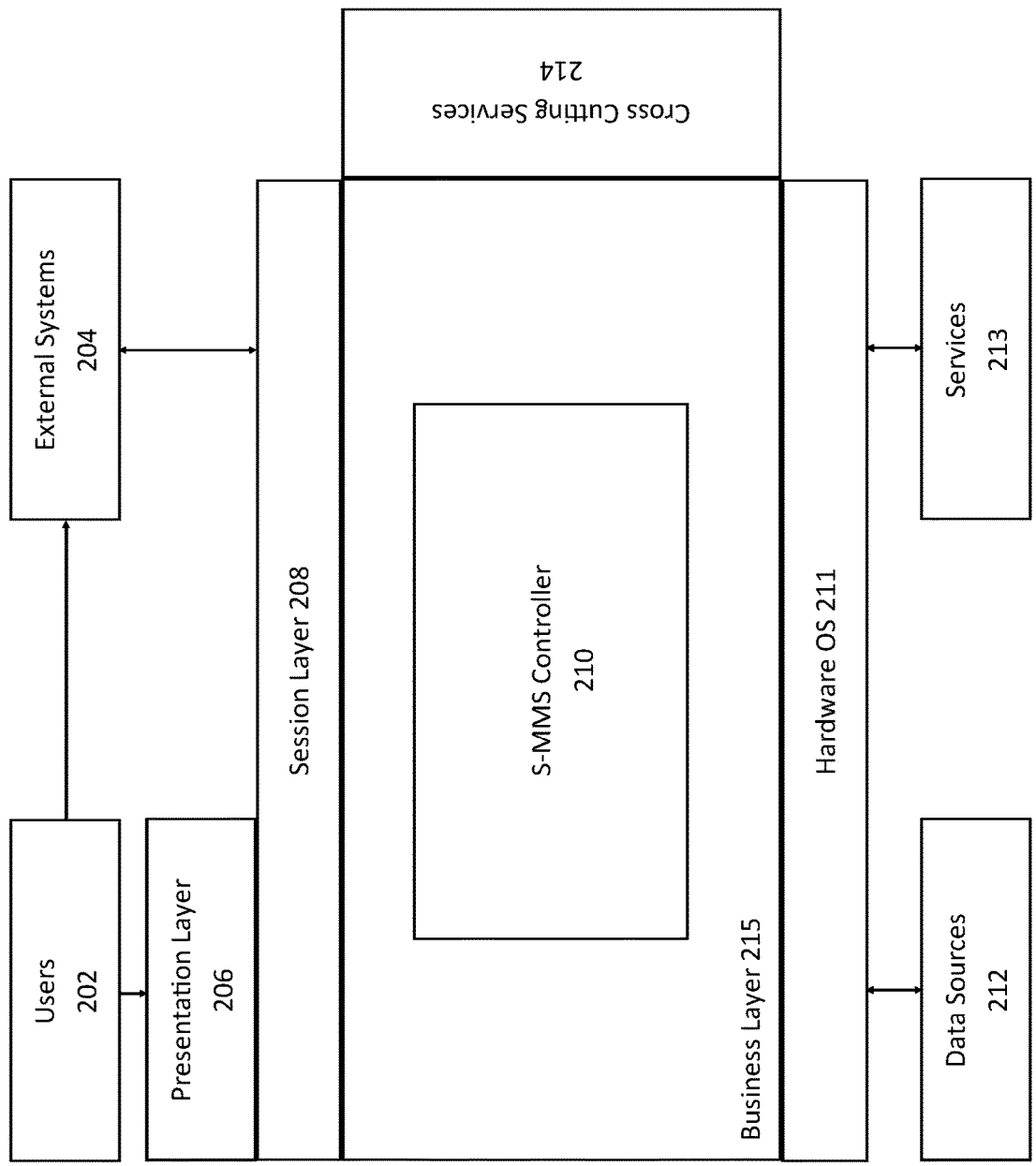
FIG. 2 depicts a control architecture adaptation of an OSI model for an embodiment of an S-MMS.

FIG. 2 depicts a control architecture adaptation of an OSI model for an embodiment of an S-MMS of the present disclosure. In the depicted embodiment, users 202 interact with external systems 204 (such as a joystick) and/or through an application. User 202 commands are transmitted through the OSI layers such as the presentation layer 206 and the session layer 208. The S-MMS controller 210 resides in a business layer 215. Below the business layer 215 lays a hardware OS 211 which shares data with data sources 212 and services 213. In some embodiments, the business layer may be protected through abstraction layers. Abstraction layers are used as a way of hiding the implementation details of a particular set of functionalities, allowing the separation of concerns to facilitate interoperability and platform independence. Cross-cutting services 214 provide services across one or more layers. Services 213 may include web services or other services that may be useful to the users 202. This overall architecture defines a structured solution that meets the technical and operational requirements for the S-MMS, while optimizing cross cutting requirements, like security, operational management, and communication.

Figure 3:
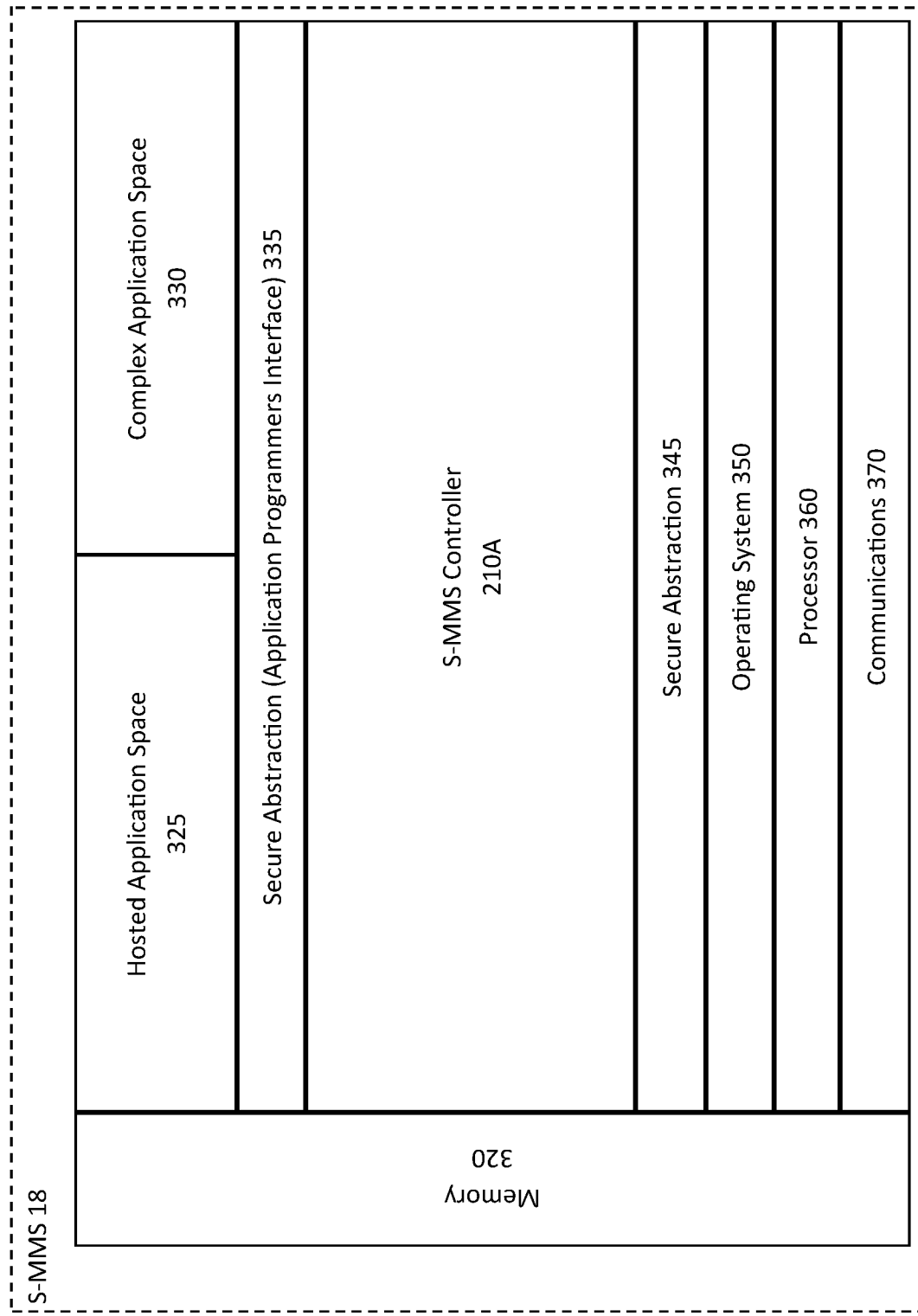
FIG. 3 is an embodiment depicting a further refinement of higher level elements into a system of hardware and software components of the S-MMS.

FIG. 3 is an embodiment depicting a further refinement of higher level elements into a system of hardware and software components for an S-MMS 18. An S-MMS controller 210A lies between two secure abstraction layers 335 and 345. The upper abstraction layer 335 abstracts through an Application Programmers Interface (API) to a hosted application space 325 and a complex application space 330. The API is a set of subroutine definitions, protocols, and tools for building applications. An API allows for communication between the various components. The complex application space 330 may include hosted control logic for an S-MMS 18. Below the S-MMS controller 210A and its secure abstraction 345 is a breakout of the operating system 350, one or more processors 360 (which are hardware), and communications layer 370, which may include a hardware communications interface. Memory 320, which is hardware, cross cuts all of the layers in the depicted embodiment and may include volatile and non-volatile non-transitory computer storage media for storing information. The S-MMS controller 210A is software that executes on one or more processors 360 on the S-MMS 18 and is stored in memory 320.

Figure 4:
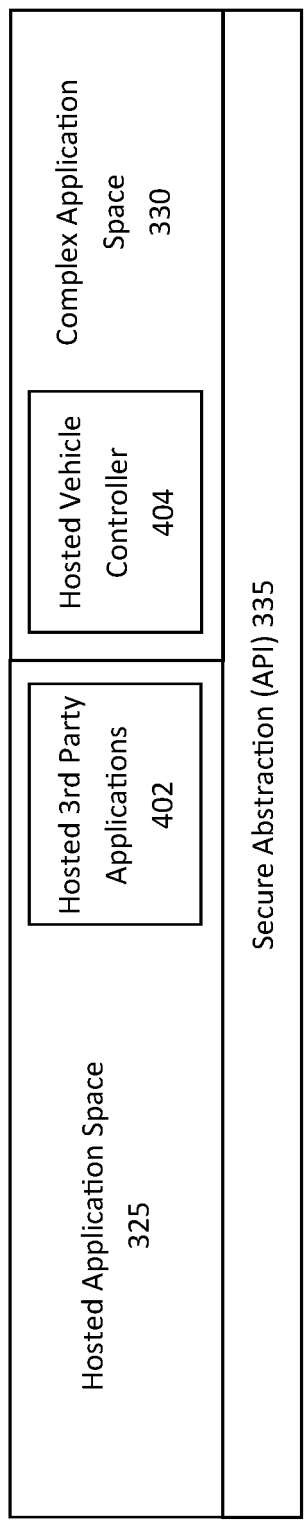
FIG. 4 depicts an embodiment of application spaces above the secure abstraction layer of the S-MMS.

FIG. 4 depicts an embodiment of the application spaces above the secure abstraction layer 335. In the depicted embodiment, the application spaces comprise a hosted application space 325 and a complex application space 330. The hosted application space 325 in the depicted embodiment comprises one or more hosted $3^{rd}$ party applications 402. The complex application space 330 in the depicted embodiment comprises a hosted vehicle controller 404.

Figure 5:
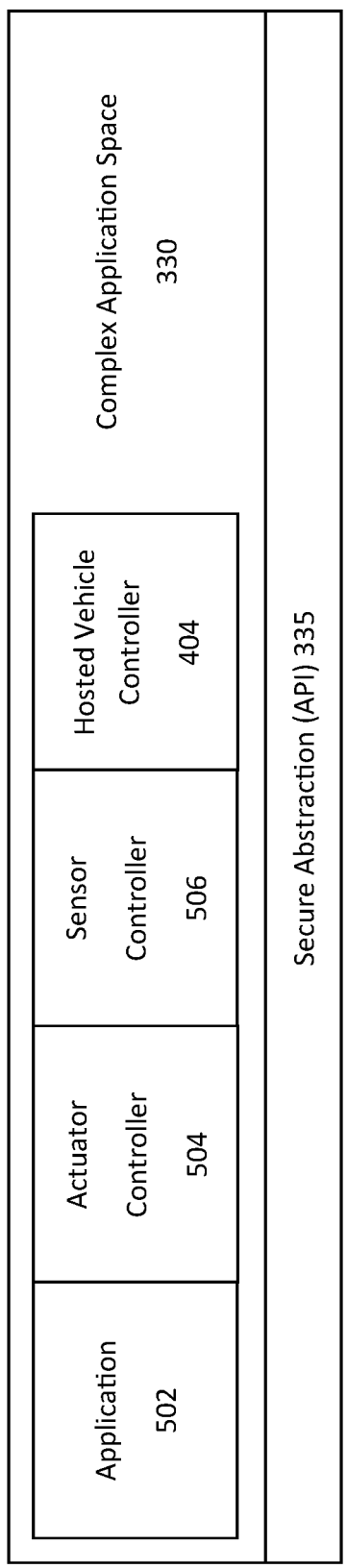
FIG. 5 depicts an embodiment of a complex application space of the S-MMS.

FIG. 5 depicts an embodiment of a complex application space 330. In the depicted embodiment, the complex application space 330 hosts applications 502, actuator controllers 504, sensor controllers 506, and hosted vehicle controllers 404 through the API 335. The concept allows for flexibility in design and implementation. As an example, a hosted vehicle controller 404 may be proprietary to a particular vendor. The depicted embodiment allows the proprietary controller 404 to either share the API or make primitive calls through the API 335 to the S-MMS controller 210A (FIG. 3).

Figure 6:
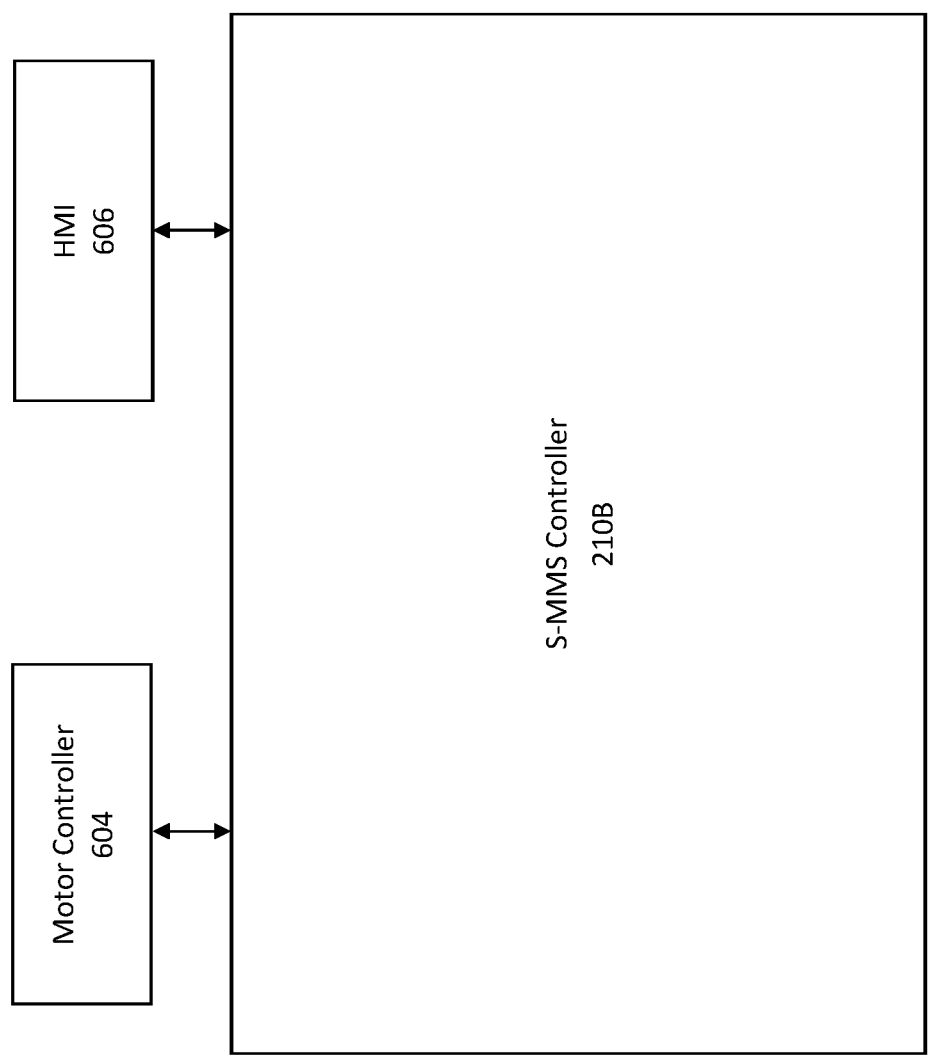
FIG. 6 depicts an embodiment of an S-MMS motor controller and Human Machine Interface (HMI) communicating with an S-MMS controller.

FIG. 6 depicts an embodiment in which the S-MMS controller 210B of the present disclosure is deployed on an S-MMS. In this embodiment, the actuator or motor controller 604 of the S-MMS may be overridden by placing the S-MMS controller 210B between the Human Machine Interface (HMI) 606 (a joystick, for instance) and the motor controller 604. In some embodiments, the HMI 606 may include one or more touch screens, buttons, voice command interfaces, keyboards, joysticks, lights, visual indicators, speakers, audible indicators, haptic devices, and/or other input and/or output devices or be replaced by or include a brain machine interface (BMI). These interfaces, in some embodiments, are open and published so an application developer can select appropriate control and HMI hardware for a desired application. In some embodiments, the HMI 606 is responsible for accepting inputs by the user as well as system warnings, displays, and notifications whether visual, audible, or tactile. The HMI is operably configured to provide control instructions to one or more of the S-MMS controller 210B or motor controller 604.

The concept of a systems control override depicted in FIG. 6 may occur with support from the supplier. The override approach may be a step toward a fully integrated control system.

The motor controller 604 controls one or more drive motors and/or one or more steering motors. In one embodiment, the motor controller 604 receives control signals from the S-MMS controller 210B and controls the drive and/or steering motors in response to those control signals. Additionally or alternatively, the motor controller 604 controls one or more motors and/or actuators used to position ancillary systems. In one embodiment, the motor controller 604 receives control signals from the S-MMS controller 210B and controls one or more actuators of a seating system in response to those control signals. In The motor controller 604 may be a controller of an existing MMS (for example, a retrofit MMS) or a new S-MMS.

In one embodiment, the control logic contained in the S-MMS controller 210B may replace an existing motor controller, the new control logic of the S-MMS controller may work with an existing motor controller and generate new commands, signals, and/or data to an existing motor controller, or the new control logic can intercept commands, signals, and/or data from an existing motor controller and generate new or different commands, signals, and/or data to one or more other system components. In some embodiments, the motor controller 604 may control the drive and/or steering motors of an S-MMS 18. In an embodiment, the motor controller 604 may control a seating system or other ancillary components on the S-MMS 18. One or more elements of the new control logic of the S-MMS controller 210B may also be integrated directly into the HMI 606 and vice versa.

Figure 7:
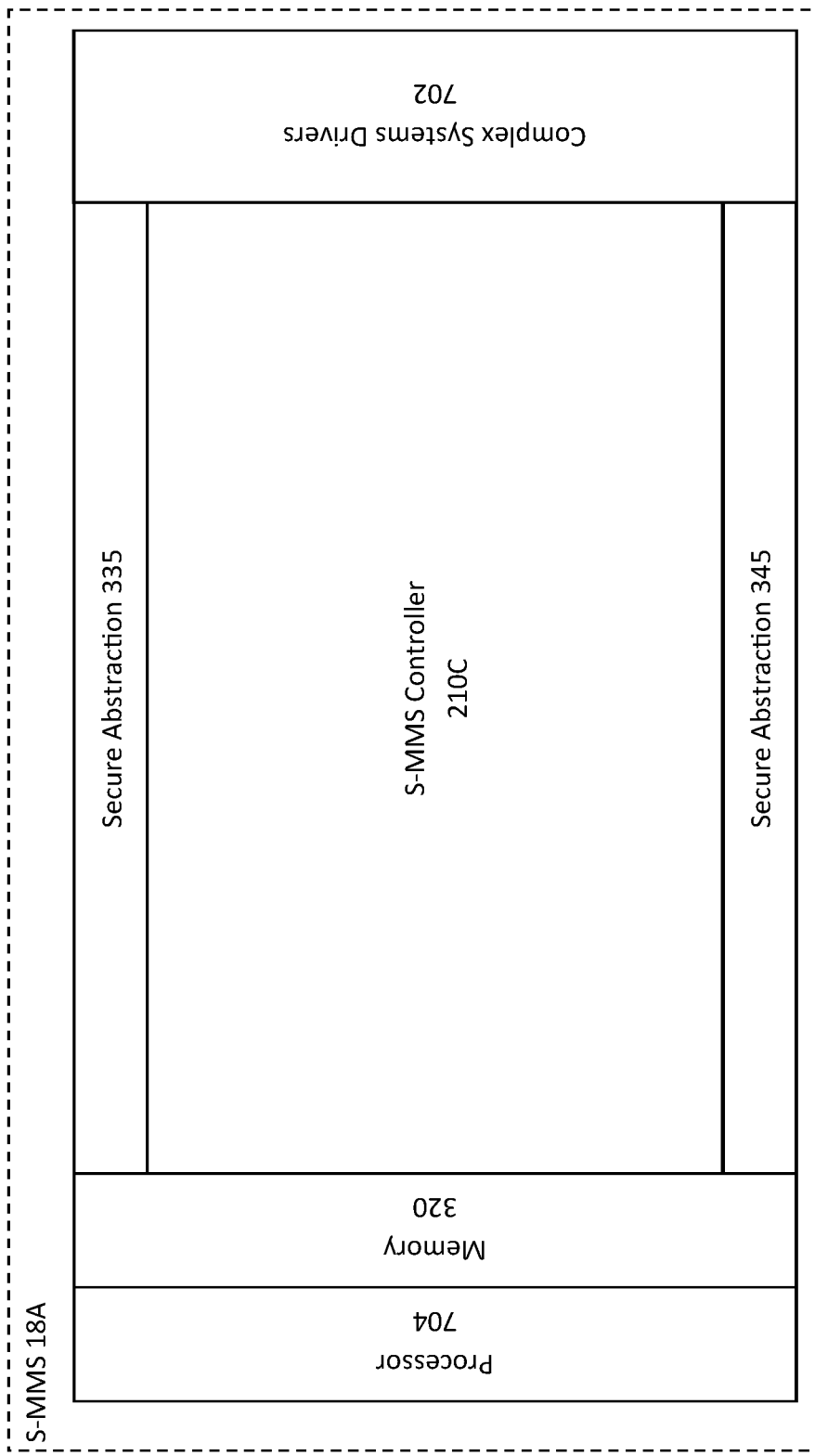
FIG. 7 depicts a simplified embodiment of an S-MMS architecture.

FIG. 7 depicts a simplified embodiment of an S-MMS architecture 18A of the present disclosure. The depicted S-MMS architecture comprises an S-MMS controller 210C between two secure abstraction layers 335 and 345. The S-MMS controller 210C and secure abstraction layers 335, 345 are run on one or more processors 704, which are hardware. Memory 320 (hardware) and complex systems drivers 702 cross-cut the layers. In some embodiments, complex systems drivers 702 may be executed by the S-MMS controller 210C and may interface to the hosted complex applications 330 (FIG. 3) through a secure abstraction layer 335 and down to the communications drivers in the communications layer/interface 370 (FIG. 3) through another secure abstraction layer 345. In some embodiments, one or more of the secure abstraction layers 335, 345 may use API's based on Bluetooth HDP to interface with complex system drivers 375 (FIG. 3) or the communication layer/interface 370 (FIG. 3). The ISO/IEEE 11073-20601 Personal Health Data Exchange Protocol (PHDEP) and associated device specialization specifications may be used to provide application level interoperability for a wide variety of devices.

Figure 8:
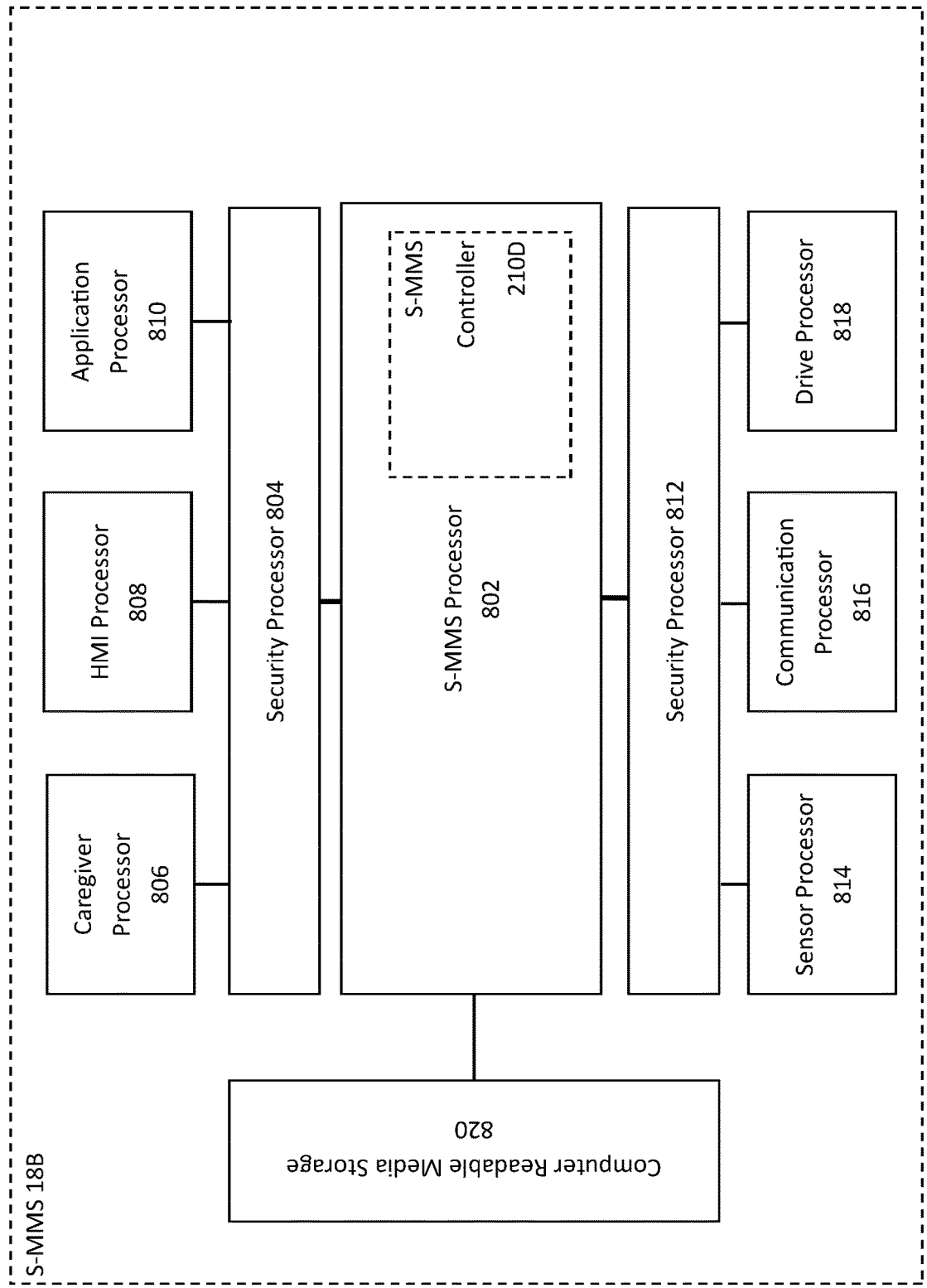
FIG. 8 depicts an embodiment of an S-MMS hardware architecture.

With a focus now on the one or more hardware processors that the S-MMS controller 210 is executed on, and interacts with, FIG. 8 depicts a hardware embodiment of an S-MMS 18B architecture. The depicted electrical architecture comprises an S-MMS processor 802 between two security processors 804 and 812, each of which is hardware. The S-MMS processor 802 may be paired with a lock-step processor (not depicted) for critical life, health, and safety applications, in some embodiments. The security processors 804 and 812 may host (i.e. execute) modules and other software, such as the previously disclosed secure abstraction APIs 335 and 345. Additionally or alternatively, the security processors may host services, such as watch-dog and data source authentication services. The S-MMS controller 210D is hosted on an S-MMS processor 802. The processors may comprise one or more of a processor, multiple processors, an application-specific integrated circuit, or a field-programmable gate array.

The S-MMS controller 210D utilizes computer readable storage media 820, which includes the memory 320, for data storage and retrieval during operation. Executable program instructions for the S-MMS controller 210D also may be stored in the memory 320. The memory 320 is one or more of a volatile and non-volatile non-transitory computer medium for storing information and may be located onboard the S-MMS 18B, may be remote storage available on a smart device or server, or some combination of the foregoing. One or more secure, encrypted memory partitions are used to store ePHI and other secure health data. The data stored on the secure memory is only made available to one or more pre-authorized systems, wherein the pre-authorized system comprises a device or service associated with an individual user. This may include a mobile motorized system, a smart device, a computer, a data terminal, or a device or service associated with an approved third party.

The S-MMS 18B may comprise multiple additional processors beyond the core S-MMS processor 802. In the case of a power wheelchair S-MMS, these additional hardware processors may include one or more caregiver processors 806, one or more HMI processors 808, one or more application processors 810, one or more sensor processors 814, one or more communication processors 816, and one or more drive processors 818, each of which is hardware. Each processor executes software and may produce control signals wherein the control signal is a wired or wireless signal, and wherein the control signal comprises one or more of a digital or an analog signal, and generally comprises or indicates data, instructions, and/or a state. A brief description of each of the additional processors for the depicted embodiment is provided below.

A caregiver processor 806 may be physically attached to the S-MMS or may be part of a remote device. In one embodiment, a caregiver processor 806 is a duplicate HMI and associated processor for the S-MMS that allows a caregiver to physically drive or otherwise maneuver or control the S-MMS or its components.

An HMI processor 808 may accept one or more user inputs from one or more HMI devices, such as a joystick or touch screen, and convert them into one or more control signals with data and/or instructions which are transmitted in response to the one or more user inputs at the HMI. Control instructions may comprise one or more of a calculation, a logical comparison, a state, a change in state, an instruction, a request, data, a sensor reading or record, an adjustment of an operating parameter, a limitation of a feature or capability, or an enablement of a feature or capability.

An application processor 810 may include one or more processors embedded in ancillary products, such as a seat controller, lighting controller, or $3^{rd}$ party device. Typically, these processors receive one or more control signals that causes them to respond with a preconfigured response, wherein the preconfigured response may include moving, measuring, changing a state, transmitting data, or taking operational control of the associated hardware (e.g. raising, lowering, or angling a seat or increasing or decreasing a light brightness or turning a light on or off). An application processor 810 may additionally or alternatively supply data about the S-MMS or use data generated from one or more sensors.

A sensor processor 814 receives data generated from one or more sensors used by the S-MMS or otherwise associated with one or more characteristics of the mobile system or a user of the mobile system. The received data may be stored in a memory and/or transmitted. Multiple sensors may use a single sensor processor 814 or multiple processors. Additionally or alternatively, individual sensors may have their own (e.g. dedicated) processors.

A communication processor 816 is used to establish one or more connections with one or more devices and transmits communications to, and receives communications from, one or more devices through associated devices of the S-MMS (e.g. one or more transceivers). Devices may communicate with the processor via wired or wireless means. These devices may be located on the S-MMS 18B or may be remote to the S-MMS 18B. A communication processor 816 may be part of a communication system for a mobile system for secure transmission and/or secure reception of data. In some embodiments, the S-MMS processor 802 may have an integrated communication processor or the S-MMS processor performs the functions of the communication processor.

In an exemplary embodiment, a communication processor 816 on the S-MMS 18B is configured to establish secure connections between the S-MMS 18B and one or more other wireless devices over which data is transmitted and received by the communication processor and the one or more wireless devices. Responsive to a secure connection being established by the communication processor 816 with a wireless device, the communication processor retrieves from a secure memory 820 one or more of stored first data or stored second data; wherein first data is data generated from one or more sensors associated with one or more characteristics of the mobile system (e.g. sensors on or used by the S-MMS 18B for measurement of distances, angles, or planes at which the S-MMS is operating, drive speed or direction, angular momentum, or other operational characteristics of the S-MMS itself) and second data is data generated from one or more sensors associated with a user of the mobile system (e.g. user presence in the seat, heart rate, seat moisture, or other characteristics of the user of the S-MMS). One or more of the first data and second data is then communicated to the wireless device via the secure connection for storage in a secure second memory of the wireless device. The wireless device associated and the communication processor 816 may communicate using one or more of cellular, 802.11, Wi-Fi, 802.15, Bluetooth, Bluetooth Low Energy, 802.20, and WiMAX.

A drive processor 818 receives one or more control signals, for example from the S-MMS controller 210D, that cause the drive processor to respond with a preconfigured response to the steering system and/or drive motor(s) of the S-MMS, wherein the preconfigured response includes one or more of taking operational control of the steering system or drive motor(s), steering the S-MMS, or starting and/or stopping one or more drive motors to move the S-MMS in one or more directions. A drive processor 818 may additionally or alternatively supply data generated from one or more sensors associated with one or more characteristics of the mobile system to the S-MMS controller 210D.

As described above, one of the goals of the present disclosure is to create a situational awareness system; the approach is iterative, in terms of implementation, meaning incremental steps are proven and become reliable over time, which can be tested against a growing requirement. Underlying the architecture of such an approach are modules that grow with the system through each growth step, with the concept of reusability through a modular approach; this is also known as a functional build-up over time.

In some embodiments, one or more sensors may be mounted to different physical locations on an S-MMS 18. In some embodiments, the sensing area/view/field of one or more sensors may overlap the sensing area/view/field of one or more other sensors or a contiguous sensing field may exist between sensors to obtain a complete 360-degree sensing area view around the S-MMS 18, which is referred to herein as a federation of sensors. In some embodiments, the one or more sensors are non-cooperating independent sensors that generate a detection response to objects with some confidence (e.g. generate a control signal that indicates one or more objects were detected and a distance to the one or more objects or other measurement data relative to the one or more objects). In such an embodiment, the kinematic states of detection that can be determined include position and time of detection. In some embodiments, control logic may be deployed in an S-MMS controller 210 to create an integrated system of systems within the S-MMS 18.

Figure 9:
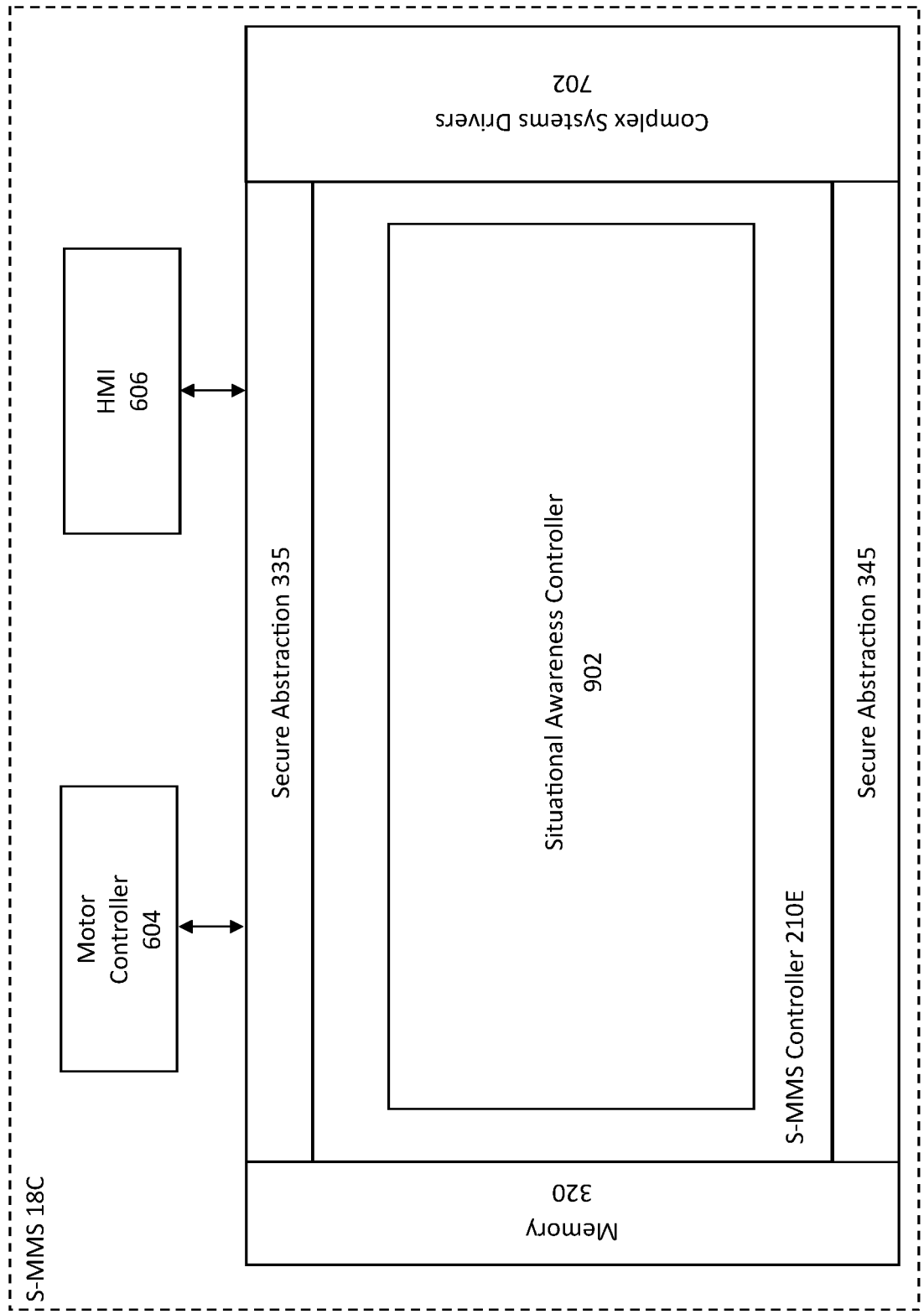
FIG. 9 depicts an S-MMS controller hosting a situational awareness controller.

FIG. 9 depicts an integrated S-MMS situational awareness controller 902 hosted in the S-MMS controller 210E. The situational awareness controller 902 operates with data generated from one or more sensors of the S-MMS or other mobile system, such as one or more of time, location, orientation, position, distance, temperature, heat, mass, force, pressure, light, resistance, voltage, current, power, video, and images. The sensors are oriented in such a way to obtain a view around the S-MMS; the sensor volumes (detection areas, fields, views, or regions) may overlap to achieve 360-degrees situational awareness in some instances. A motor controller 604 and Human Machine Interface (HMI) 606 communicate with the situational awareness controller 902. These interfaces, in some embodiments, use open and published API's 335 so an application developer can select appropriate control and HMI hardware for a desired application.

Figure 10:
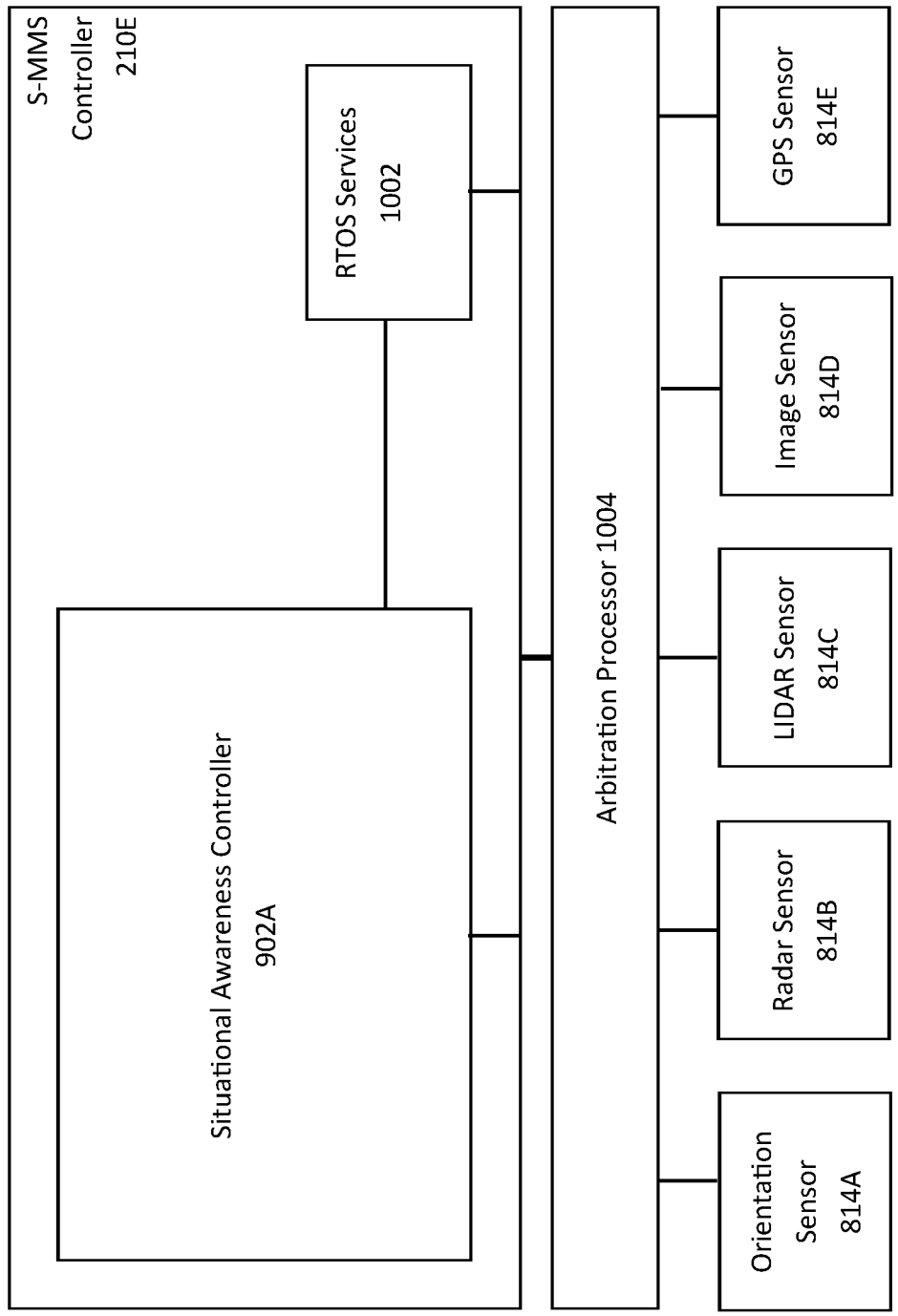
FIG. 10 depicts an embodiment of an S-MMS architecture wherein the S-MMS controller hosts a situational awareness controller.

FIG. 10 depicts an embodiment of a S-MMS 18 architecture wherein the S-MMS controller 210E hosts a situational awareness controller 902A that is supported by real-time operating system (RTOS) services 1002. The RTOS services 1002 may include a number of services, including communications management, memory management, watchdog services, and prognostics and health management (PHM). In an embodiment of RTOS services 1002, PHM includes monitoring communications with components and external hardware systems through heartbeat messages, memory management and memory isolation, and systems tests. Systems tests include startup built in self-tests to ensure system wide high reliability, management of repair cycles, and system redundancy.

PHM includes a number of tests. A power-on self-initiated built in test (SBIT performs a comprehensive system test and logs the test reports to memory. The test reports can be transmitted through a secure wireless connection to a secure database. A periodic built in test (PBIT) assures that the S-MMS has not become unsafe since the SBIT. Safety-critical devices normally define a "safety interval", a period of time too short for injury to occur. The PBIT of the most critical functions normally is completed at least once per start-up interval. The PBIT in some embodiments operates as a subset of the SBIT with similar logging and reporting functions. Finally, an initiated built in test (IBIT) is available in some embodiments to the user locally from the HMI. However, the IBITs are normally reserved for the technicians during annual or scheduled maintenance. In some embodiments, the S-MMS is serviced through a communication network and technicians can access the S-MMS remotely for testing, maintenance, and repair.

With a focus on the sensors needed to obtain a view around the S-MMS, multiple example sensors are shown 814A thru 814E. In the embodiment depicted, these include an orientation sensor such as a gyroscope 814A, a RADAR sensor 814B, a LIDAR sensor 814C, an image sensor such as a camera 814D, and a GPS sensor/receiver 814E. Each sensor may have a unique onboard processor or a common processor with other sensors and provide data to the processor either in a continuous stream or in response to a request. The sensor communications received from each sensor are termed sensor reports. Each sensor processor may operate at different clock speeds and may communicate with the S-MMS controller 210E using different communication protocols (e.g. serial communications, I2C communications, etc.). For these reasons, the embodiment shown includes an arbitration processor 1004 (hardware) which may take multiple inputs and convert them to a standard interface to communicate with the S-MMS controller 210E. In other embodiments, one, none, or many arbitration processors may be required.

Figure 11:
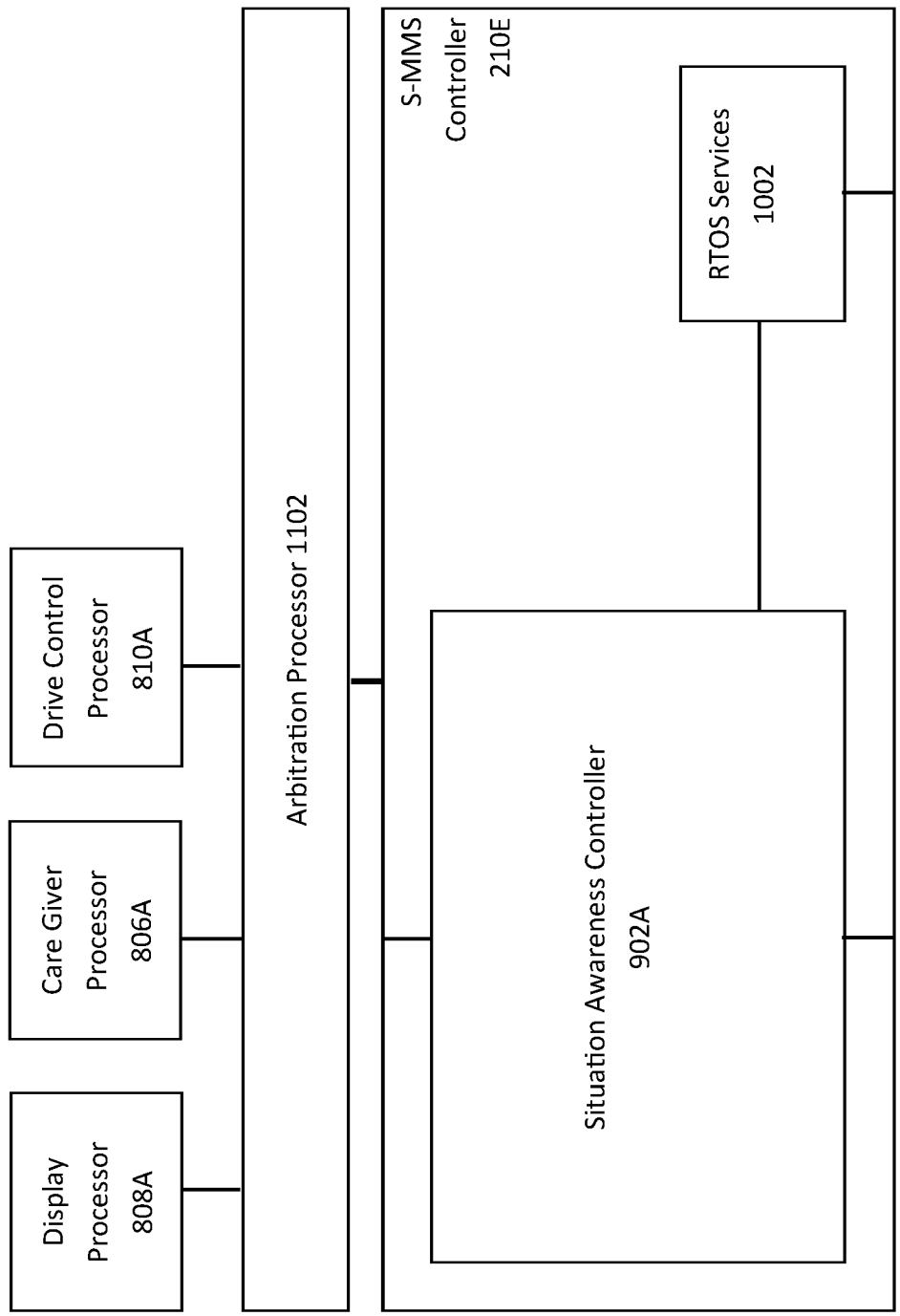
FIG. 11 depicts processors for the system of FIG. 10.

FIG. 11 depicts the S-MMS controller 210E from FIG. 10, with a focus on how additional arbitration hardware processors may be required. In the embodiment depicted, a display processor 808A, a processor onboard a caregiver device such as a remote driver override device 806A, and a drive control processor 810A communicate with the S-MMS controller 210E via an arbitration processor 1102.

Figure 12:
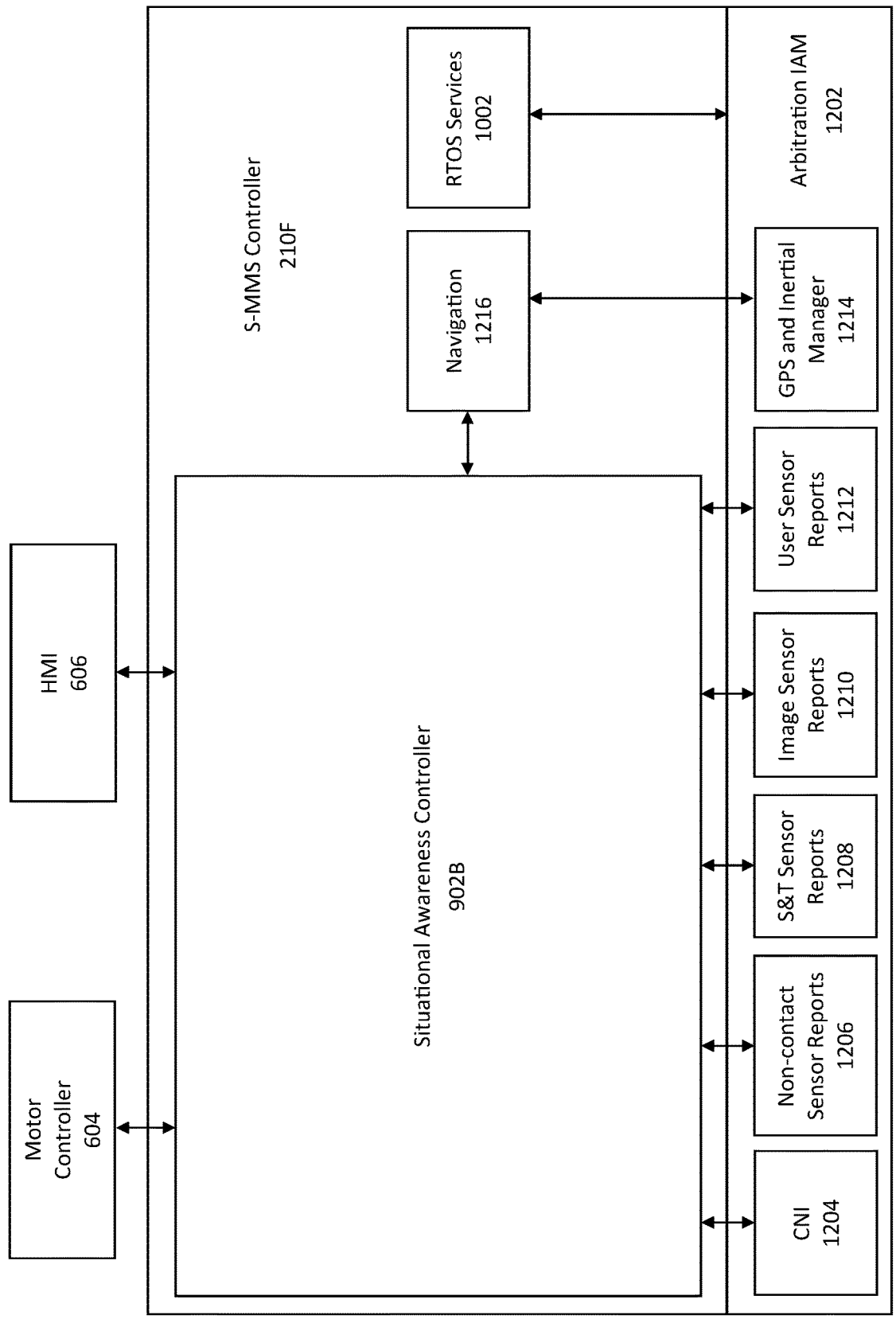
FIG. 12 depicts another embodiment of an S-MMS controller.

FIG. 12 depicts an embodiment of FIG. 6 with additional detail. The depicted embodiment comprises a situational awareness controller 902B within an S-MMS controller 210F. S-MMS situational awareness controller 902B communicates with a motor controller 604 and Human Machine Interface (HMI) 606 as depicted in FIG. 6. The depicted S-MMS controller 210F further comprises real-time operating system (RTOS) services 1002 and navigation 1216.

An arbitration Information Assurity Manager (IAM) 1202 manages sensor reports from one or more sensors on or used by the S-MMS 18 and may include communication, navigation, and identification (CNI) 1204 processing capabilities. In some embodiments, the arbitration IAM 1202 resides on a security processor 812 (FIG. 8) or dedicated arbitration processor 1004 (FIG. 10). Additionally or alternatively, functions of the CNI 1204 may be performed by a dedicated communication processor 816 (FIG. 8). Sensor reports received and managed by the arbitration IAM 1202 may include non-contact sensor reports 1206, search and track sensor reports 1208, image sensor reports 1210, and user sensor reports 1212. Sensor reports (1206-1212) may be composed of data stored in one or more of long-term or short-term system memory 320 or read from an input port on a S-MMS 18B processor (e.g. processors 812, 816, or 814). A report (1206-1212) may include additional data beyond a simple measurement, including sensor status, confidence levels, or other information.

Non-contact sensors are devices used to take a measurement, often a distance, without coming in contact with the detected object. There are many types of non-contact sensors, including optical (e.g. LIDAR), acoustic (e.g. RADAR or ultrasonic), and magnetic (e.g. hall effect sensor). Microphones may additionally be included as a non-contact sensor. Search and track sensors may include image and non-contact sensor types, but are sensors that often have larger fields of view and may scan within these fields of view. Image sensors detect and convey information that constitutes an image or series of images/video wherein the image(s)/video may contain light or electromagnetic radiation information on an area. These sensor reports interface to the specific sensor types in the system to identify measurements, detections, number, efficiency, health, degraded performance, states, statuses, and/or other data of each sensor in the sensing system.

The depicted arbitration IAM 1202 further comprises a global positioning system (GPS) and inertial manager 1214. In the depicted embodiment, the situational awareness controller 902B communicates with the CNI 1204, sensor reports 1206, 1208, 1210, and 1212 and navigation 1216. Navigation 1216 communicates with the GPS and inertial manager 1214 in the arbitration IAM 1202. The depicted embodiment of the situational awareness controller 902B includes logic to manage the sensors, including one or more of on and off, sweep rate, sensor volume, regional interrogation, and/or other operations.

The CNI 1204 manages communications through system links and off board links to enable vehicle to device, intra-vehicle, and inter-vehicle communication and coordination, including cooperative navigation among vehicles and using other devices and identification of devices and vehicles. In some embodiments, the CNI 1204 identifies other data sources and retrieves data from other data sources, including for threats detected and kinematic states of sensors, vehicles, and devices. The CNI 1204 is also responsible for GPS corrected system-wide time and processor time sync across the system in conjunction with the operating system. For example, the CNI 1204 receives an accurate time via the GPS and inertial manager 1214 and transmits that accurate time to all hardware processors along with an instruction to sync their internal clocks to that accurate time. This time coordination function is important in some embodiments since errors in time coordination can introduce as much error in system performance as a bad sensor reading in those embodiments. Propagating a sensor measurement to the wrong point in time can induce significant confusion to filters, such as a Kalman filter, especially if time goes backward due to sync errors.

The CNI 1204, in some embodiments, may be configured to receive data from one or more different sources, including other like-equipped S-MMSs, vehicles and traffic devices, among others, through a Dedicated Short-Range Transceiver (DSRC), for instance, across an IEEE 802.11P link, which may be formatted in an IEEE 1609 format. This data may help the user to better navigate next to a roadway or along paths that are shared by automobiles. Some embodiments may allow for traffic lights, speed signs, and traffic routing to be dynamically altered. For an S-MMS user, the ability to announce one's presence and thereby enable a traffic control device to effect a change in traffic, such as by changing a stop light to red, could be lifesaving.

A search and track function 1208 may be used to maintain sensor health, detect sensor failures, monitor sensor zones of coverage, and notify the situational awareness controller 902B or other component of the S-MMS controller 210F of sensor system degradation or other states. The search and track function 1208 may also manage the transition of sensors from online and off-line states (including plug and play future options).

The user sensor reports 1212, in some embodiments, may be configured to receive data from one or more sensors used to monitor user condition, user position, and/or user status. This data may allow for assistive behaviors to be triggered and/or tuned by the situational awareness controller 902B to the human in the loop of the S-MMS 18.

The GPS and inertial manager 1214 includes one or more inertial measurement unit (IMU) data services that receives one or more reports from an attitude and heading reference system (AHRS) that includes an IMU. An IMU of an AHRS consists of one or more sensors on three axes that provide attitude information of the S-MMS 18 to the GPS and inertial manager 1214, including yaw, pitch, and roll of the S-MMS and deviations to each. As an example, an x-axis may typically be lateral across the S-MMS 18 coaxial with the axles of the front wheels of the S-MMS, extending 90-degrees left and 90-degrees right, a y-axis may extend forward and rearward of the S-MMS, and a z-axis may extend vertically through the S-MMS, 90-degrees to the x and y axes. An IMU typically comprises acceleration and rate determining sensors on each axis. In the case of x, y, and z measurements, the IMU is referred to as a 6-Degree of Freedom (DOF) sensor. Some IMUs also have a small hall device on each axis to measure the magnetic line of flux of the earth's magnetic poles, similar to a compass, that allows for the calculation of true, earth referenced orientation. These IMU embodiments are referred to as a 9-DOF sensor and are more accurate than a 6-DOF sensor. However, some systems may interpolate the z-axis by detecting gravity on either the x or y axes, which may be less accurate. The IMU is fixed to the S-MMS 18 in some embodiments and provides reports to the GPS and inertial manager 1214.

The GPS and inertial manager 1214 also receives GPS signals from a GPS receiver. The GPS receiver may be mounted to the S-MMS 18, be part of a smart device paired or otherwise linked to the S-MMS, or be another receiver that transmits signals to the S-MMS or a smart device linked to the S-MMS.

Navigation 1216, in the depicted embodiment, is an inertial reference system, including an inertial navigation system (INS), for navigating using dead reckoning (DR). Dead reckoning is the process of calculating the S-MMS 18 current position by using a previously determined position, or fix, and advancing that position based upon known or estimated speeds and steering over elapsed time and heading. In one embodiment, DR uses GPS location data (e.g. via GPS and inertial manager 1214) to update the INS DR fix. Speed, heading, and elapsed time data are then provided by the INS function of navigation 1216 to the situational awareness controller 902B. S-MMS speed (e.g. velocity and/or acceleration) may be received directly from one or more motor controllers 604. Additionally, speed and heading may be received or calculated from one or more GPS and inertial manager 1214 reports. Elapsed time is provided by RTOS services 1002. The navigation 1216 allows the S-MMS 18 to navigate inside a building without GPS or otherwise (e.g. outside of GPS coverage) to a similar degree of accuracy as navigating outside with continuous GPS data or otherwise. Speed, heading, and elapsed time for navigation 1216, in some other embodiments, is calculated onboard the processors of internal and/or external sensors, including one or more GPS receivers and one or more solid state inertial measurement units (IMU). In some embodiments, the S-MMS processor 802 calculates speed, heading, and elapsed time and generates steering and drive signals, including optionally based on one or more non-contact sensor reports and/or GPS and inertial manager reports.

Figure 13:
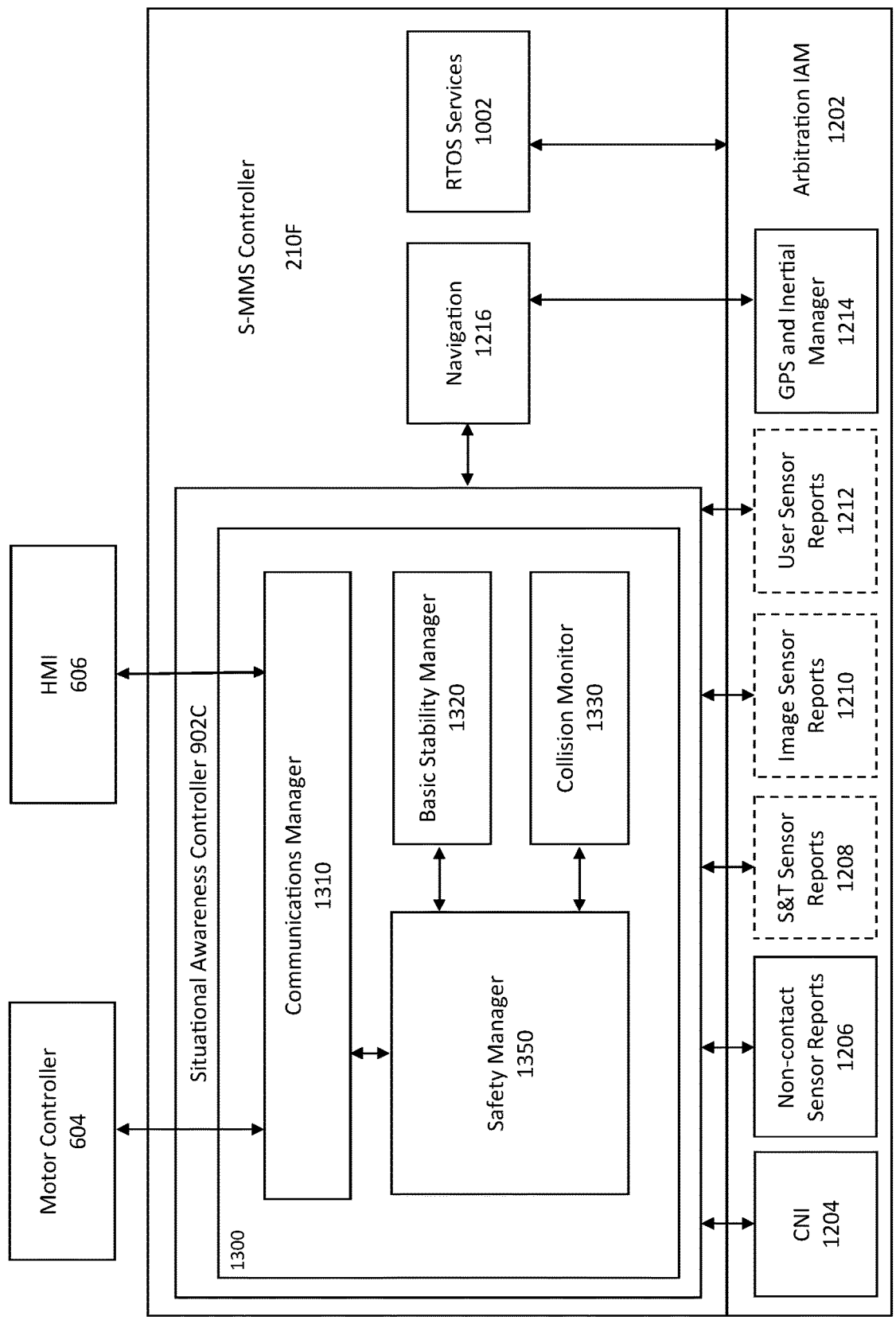
FIG. 13 depicts another embodiment of an S-MMS controller.

FIG. 13 depicts an embodiment of FIG. 12 where the situational awareness controller 902C comprises a Generation I system embodiment 1300. The system 1300 comprises a communications manager 1310, a basic stability manager 1320, a collision monitor 1330, and a safety manager 1350. Each of these processes receive data from one or more sensors, including data from the non-contact sensor reports 1206 and/or data provided via the CNI 1204. S-MMS orientation sensor reports from the GPS and inertial manager 1214 are transmitted to the situational awareness controller (SAC) 902C via navigation 1216. The human machine interface (HMI) 606 transmits user inputs to the SAC 902C.

Signals from the HMI 606 are used as an input to the SAC 902C safety manager 1350. The HMI 606 input is analyzed by the SAC 902C and compared by the SAC to the situational awareness states determined by the basic stability manager 1320 and collision monitor 1330 (e.g. unstable or collision states, as described more fully below). If an unstable or impending collision state is detected by the basic stability manager 1320 or collision monitor 1330, respectively, then the SAC 902C may replace the HMI input values by one or more new values calculated by the safety manager 1350. In this way, the SAC 902C may arbitrate messages between the HMI 606 and the motor controller 604. Additionally or alternatively, the physical behavior of the HMI 606, such as joystick force resistance, may be modified by the SAC 902C to provide feedback to the user based on the output of the safety manager 1350. The S-MMS controller 210F reports drive processor 818 (FIG. 8) outputs, application processor 810 (FIG. 8) outputs such as seating system positions, and other available data from the MMS to the SAC 902C for use in decision making by the associated processes. Communications between the HMI 606, the motor controller 604, and the safety manager 1350 may be controlled by a communications manager 1310.

The basic stability manager 1320 monitors sensor inputs from non-contact sensor reports 1206 and GPS and inertial manager 1214 and determines the current and/or predicted future stability of the S-MMS. A timeline for any necessary steering corrections and any future coupled steering maneuvers to minimize accidents due to instability are computed by the basic stability manager 1320, such as based on the non-contact sensor reports 1206 and GPS and inertial manager 1214 reports/sensor inputs. Any system cutoffs, emergency braking, and/or drive processor 818 (FIG. 8) disengagement functions also are performed by the basic stability manager 1320, such as based on the non-contact sensor reports 1206 and GPS and inertial manager 1214 reports/sensor inputs.

A collision monitor 1330 monitors sensor inputs from non-contact sensor reports 1206 and/or optionally from one or more image sensor reports 1210 and determines the current and/or predicted future time to impact for objects detected within a certain distance and/or perimeter of the S-MMS based on the non-contact sensor reports 1206 and/or optionally from the one or more image sensor reports 1210. The collision monitor 1330 is a single-mode variance system in one example. A single-mode variance system makes logical decisions by analyzing individual sensor reports, where each sensor has distinct capabilities and a fixed set of errors inherent to the sensor. The appropriate timeline for any necessary steering corrections and any future coupled steering maneuvers to minimize accidents due to collision may be computed by the collision monitor 1330, such as based on the non-contact sensor reports 1206 and/or optionally on one or more image sensor reports 1210. Any system cutoffs, emergency braking, and/or motor controller disengagement functions may be performed by the collision monitor 1330, such as based on the non-contact sensor reports 1206 and/or optionally on one or more image sensor reports 1210.

The safety manager 1350 communicates with sub-processes that look at S-MMS stability states and/or other data (e.g. via the basic stability manager 1320) and collision states and/or other data (e.g. via the collision monitor 1330) and decides what actions should be taken based on the stability and collision states and/or other data. For example, based on the stability and/or collision states and/or other data, the safety manager 1350 may modify user inputs for steering and/or drive control, e.g. via overriding/modifying user inputs received from the HMI 606 before they are communicated to the motor controller 604, process the user inputs to create an output to be sent to the motor controller 604, or transmit new outputs/instructions to the motor controller 604. The safety manager 1350 may independently send commands to both the HMI 606 (e.g. to provide instructions or feedback to the user via the HMI) and the motor controller 604 (e.g. to control steering and/or drive motors or other devices or request status of the motors and/or devices). Functions that may be performed by the safety manager 1350 include instructing sensors to take sensor readings and using a rules engine to determine control command outputs based on the states of the basic stability manager 1320 and collision monitor 1330. The goal of the safety manager 1350 is to produce a combined view of the safety of the S-MMS surroundings at any given moment. In some implementations, the functions of the safety manager 1350 may be referred to as tactical management and threat assessment and may use predictive algorithms and determination/designation of safe directions and/or velocity of travel.

The S-MMS 18, in some embodiments, communicates with other devices, such as a smart phone, tablet, or computer, (e.g. via the communication processor 816 (FIG. 8) of the S-MMS 18) with Bluetooth, Bluetooth Low Energy, Wi-Fi, and/or other wireless signals, such as light frequency navigation being deployed for indoor tracking and navigation. As these systems grow in use, the S-MMS 18 will take advantage of them. In combination with previously known GPS locations and DR, the S-MMS 18 will be able to estimate its position in indoor environments with even greater accuracy.

The term "configuration item" is either a hardware or software item. A "computer software configuration item", or CSCI, is a configuration item in software. A number of CSCIs are described below. However, there can be more or less.

Figure 14:
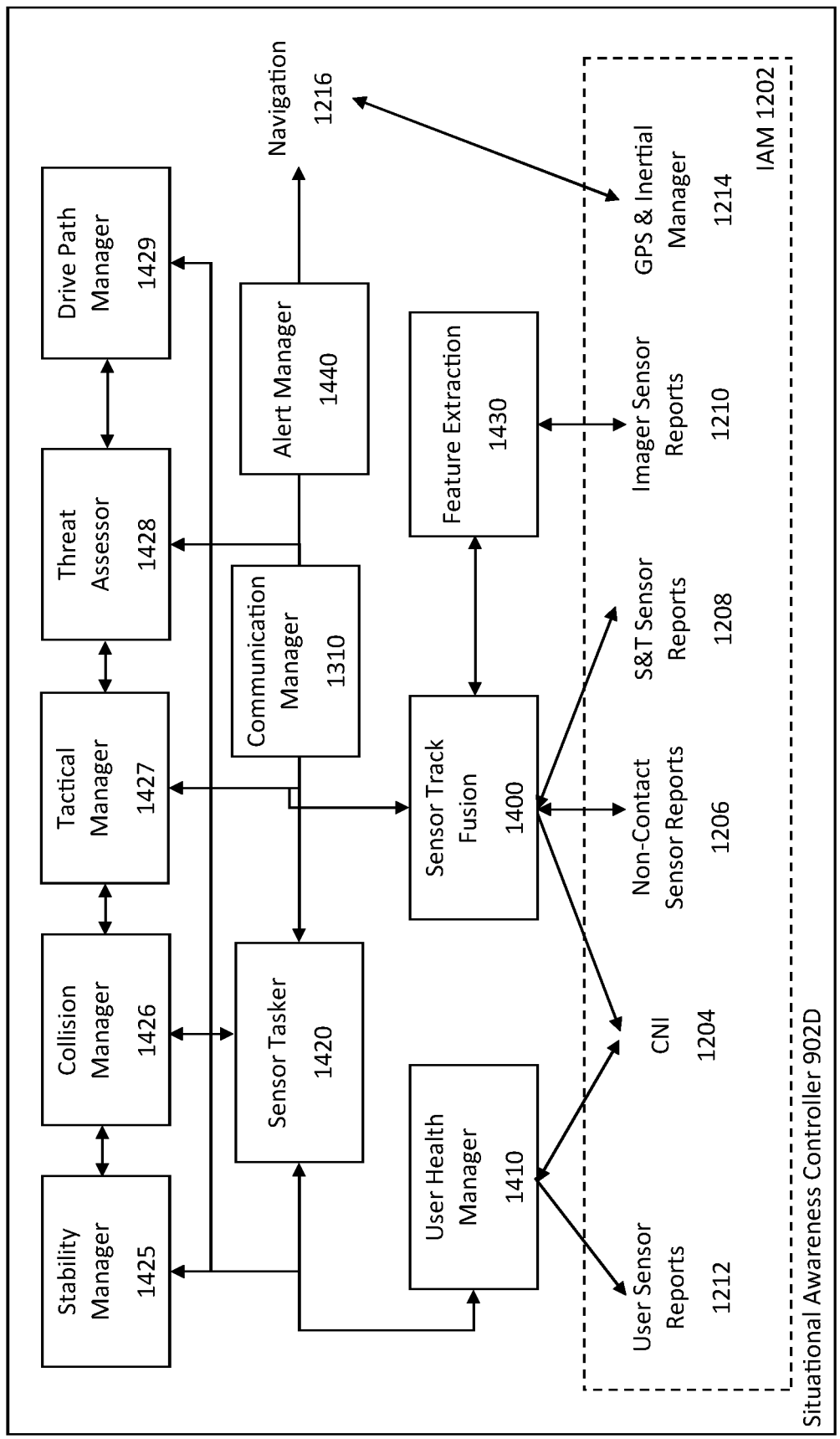
FIG. 14 depicts an embodiment of a situational awareness controller.

FIG. 14 depicts an embodiment of a situational awareness controller 902D that may be deployed in the architecture described by FIG. 13 in place of the basic stability manager 1320, collision monitor 1330, and safety manager 1350 of the SAC 902C. In addition to the functions described above, navigation 1216 tracks S-MMS position and kinematic states in real time. The real-time position and kinematic state data is used by sensor track fusion 1400 to remove any vibrations or roll/pitching actions that affect the sensor coordinate frames in which the reports are sent. Navigation 1216 can also track the S-MMS position even when the vehicle is outside of GPS coverage using a combination of dead reckoning and position orienting signals, such as indoor wireless beacons and position orienting signals from other vehicles and/or smart devices.

Sensor track fusion (STF) 1400 is responsible for processing, filtering, and reporting detections of one or more areas around an S-MMS 18 (e.g. between 0 and 360 degrees from a point or location on the S-MMS 18, 360 degrees around an S-MMS 18, and/or one or more overlapping areas from or around the S-MMS 18). This is accomplished by processing reports from the available sensors 1204-1214 and/or feature extraction 1430. Next, recursive filtering (e.g. in one embodiment a Kalman filter) is used to estimate the state of each track based on the processed reports (e.g. 1204-1214, 1430) in combination with one or more kinematic models (e.g. algorithms or mathematic equations) of possible track motion, for example, to determine if the track is in motion or stationary relative to the S-MMS. The estimate is compared to the state of each previously identified track maintained by the tactical manager 1427 of the SAC 902D. If the STF 1400 determines there is a high-quality match, the state of that track is updated in the tactical manager 1427. If not, a new track is generated and communicated to the tactical manager 1427. Upon track generation, a priority may be established based on time to impact by the threat assessor 1428, and additional sensor data may be requested by transmitting a tasking request to sensor tasking 1420.

A user health manager (UHM) 1410 is responsible for processing, filtering, and reporting changes in user behavior and/or health that may be relevant to the situational awareness controller 902D of the S-MMS. Data from user sensor reports 1212, CNI 1204, and/or HMI inputs 606 (FIG. 12) are used by the UHM 1410 to monitor individual and combined health metrics. The UHM 1410 then determines the appropriate timeline for any S-MMS controller 210F intervention or adjustments to SAC 902D behavior. The UHM 1410 may further access a user profile and log user data to secure memory linked to the user profile.

A sensor tasker (ST) 1420 responds to sensor information requests from sensor track fusion 1400 and sensor information prioritizations from the threat assessor 1428. These priorities are used by the sensor tasker 1420 to change sensor update rates for possible unsafe conditions (e.g. such as collisions or tipping danger) and to manage sensor front-end resources to maintain the highest quality tracks on the closest detections. A track is a threat to the S-MMS 18 that has been identified by the SAC 902D and given a unique identifier for use in future calculations and processes. The sensor tasker 1420 may act as a filter and utilizes the S-MMS system kinematic and identity information for decision making based on predefined decision boundaries to control the amount of sensor data provided to the SAC 902D at a given instant.

In this embodiment, a stability manager 1425 determines the stability of the S-MMS 18 and whether the upcoming ground is likely to cause instability (e.g. tipping) based on one or more inputs from navigation 1216, sensor track fusion 1400, and/or threat assessor 1428. The stability of the S-MMS 18 is calculated based on orientation readings (e.g. pitch and/or roll) received from navigation 1216 (e.g. from one or more inertial measurement units fixed to the S-MMS) in combination with a mathematical tipping model for the S-MMS 18 stored in memory and executed by the stability manager 1425. The stability manager 1425 also determines the suitability of upcoming terrain based on factors, such as topographic profile and/or surface composition as measured by one or more sensors 1204-1208 and 1210 in relation to current S-MMS 18 operation characteristics, such as orientation and S-MMS kinematics (e.g. rate of travel, direction of travel, and S-MMS configuration settings). In an example, an S-MMS 18 may have known limits for pitch and roll where tilting beyond the known limits causes the S-MMS to tip. Based on the current orientation (e.g. pitch and/or roll) of the S-MMS, the stability manager 1425 may use readings of the ground slope around the S-MMS to estimate the future pitch/roll of the S-MMS if it travels further forward. If the pitch/roll is below a threshold, the action is allowable. If not, then the action is not allowable. A list of stability conditions and their location relative to the S-MMS 18 are provided to the tactical manager 1427 for integration into the master threat assessment map. The appropriate timeline for any necessary steering actions and any future coupled steering maneuvers to minimize instability accidents may be computed by the stability manager 1425. System cutoffs, emergency braking, and/or motor controller disengagement functions may be performed by this stability manager 1425. The stability manager 1425 may further include crash event data recording and logging for use in S-MMS system diagnostics, in some embodiments.

A collision manager 1426 computes the Time to Impact (TTI) function based on one or more inputs from threat assessor 1428 and sensor fusion 1400. The TTI function uses received sensor data associated with one or more objects located around the S-MMS 18 in combination with the current state of the S-MMS 18 (e.g. heading, velocity, and/or acceleration) to estimate the time until a collision with those objects is anticipated. The collision manager 1426 then determines the appropriate timeline for any necessary steering actions and any future coupled steering maneuvers to minimize collision accidents. Any system cutoffs, emergency braking, and/or motor controller disengagement functions may be performed by the collision manager 1426. The collision manager 1426 may further include crash event data recording and logging for use in S-MMS system diagnostics, in some embodiments.

A tactical manager 1427 uses inputs from one or more of a stability manager 1425, collision manager 1426, drive path manager 1429, navigation 1216, threat assessor 1428, and/or sensor track fusion 1400 to maintain a master, 360-degree map of known objects and conditions in relation to the S-MMS 18. The tactical manager 1427 combines the outputs of the stability manager 1425 (e.g. a map and/or an identification of the ground surrounding the S-MMS) and collision manager 1426 into a single, integrated map of known tracks. Each track may be assigned a threat level by the threat assessor 1428. The current direction and speed of travel (e.g. from navigation 1216) and/or desired future direction and speed of travel (e.g. drive path manager 1429) can then be overlaid on the threat assessment map maintained by the tactical manager 1427.

A threat assessor 1428 function evaluates the multiple tracks and/or objects detected by the SAC 902D processes, including the stability manager 1425, collision manager 1426, tactical manager 1427, and feature extraction 1430, and prioritizes them. Prioritization may be based on a rules engine. The rules engine executes one or more predefined rules as part of threat assessor 1428. In one example, the rules engine uses a statistical assessment of the threat posed by each track and/or object based on the estimated time to impact to each track provided by the collision manager 1426 in combination with the safe speed determined in the direction of travel provided by the stability manager 1425 and/or drive path manager 1429. If an identified track presents a statistical risk above a predefined threshold, the threat assessor 1428 will prioritize that track above other tracks with lower calculated risk numbers. The prioritized list of tracks from the threat assessor 1428 is sent to the sensor tasker 1420 which may take additional readings or otherwise focus sensor resources on the highest threat tracks. Additionally, the prioritized list of tracks from the threat assessor 1428 may be sent to the tactical manager 1427 so that areas with a high concentration of high threat tracks may be flagged as keep-out zones.

A drive path manager (DM) 1429 is responsible for route determination, interpretation of external map data (e.g. received from external sources such as a remote server or smart device via CNI 1204) for future advanced routing functions, and generation of steering actions for autonomous by wire speed sensitive steering support. External map data, when received, must be oriented to match the S-MMS 18 reference frame by the DM 1429 so that it can be used with the threat assessment map maintained by the tactical manager 1427. The DM 1429 combines one or more inputs from the tactical manager 1427, sensor track fusion 1400, threat assessor 1428, and/or navigation 1216 in order to determine where the S-MMS 18 should drive. The DM 1429 contains a complex 6-DOF S-MMS 18 model that may be used in predictive applications to support stop and go functions, in some embodiments.

Feature extraction 1430 performs angle resolution, object detection, edge detection, and bore sight correction for the S-MMS. Angle resolution is the process of determining the location and error of the orientation of a feature (e.g. object, edge, surface, or plane) around the S-MMS 18. Bore sight correction is the process of correcting downrange measurements for sensor misalignment. The sensor tasker 1420 receives raw data of one or more image sensors via the image sensor reports 1210, uses pixel masks from the sensor tasker 1420, produces a detection report by applying one or more pixel masks to one or more image sensor reports, and assigns a unique identifier (identity) and kinematic data to each track identified in a detection report for sensor track fusion 1400 consumption. Pixel masks are used to filter out or obscure areas of an image that are not of current concern to the SAC 902D process in order to decrease compute time and resources required for the process.

In some embodiments, an alert manager 1440 may be hosted on (e.g. executed by) the SAC 902D, one of the SAC 902D processes (e.g. communications manager 1310 or stability manager 1425), and/or hosted in one or more of the application spaces 325 and/or 330 (FIG. 3).

In an embodiment, the alert manager 1440 responds to inputs from stability manager 1425, collision manager 1426, drive path manager 1429, and/or STF 1400 to alert the user to possible dangers, enabling a warning, caution, or advisory to actually come from the direction of the problem. For example, the alert manager 1440 of the SAC 902D generates one or more signals to one or more speakers on or around the S-MMS 18 causing the one or more speakers to produce one or more sounds that are either generic or particular to the particular speakers (e.g. one sound for a right lateral speaker to notify the user of an alert on the right lateral side of the S-MMS, another sound for a left lateral speaker to notify the user of an alert on the left lateral side of the S-MMS 18, another sound for a forward speaker to notify the user of an alert in front of the S-MMS, and another sound for a rear speaker to notify the user of an alert behind the S-MMS). This alert manager 1440 may receive and process data from the collision manager 1426, the stability manager 1425, and/or the UHM 1410, such as timing for predicted collision, instability, or user health issues, and coordinate one or more alerts with the time for the predicted collision, instability, or user health issue for crash mitigation or condition avoidance. This timing may be based on expected user reaction times and user health considerations. In some embodiments, an audio alerting function or 3D audio is implemented. When an obstacle or dangerous condition is detected, one or more sounds are produced from the direction of the threat by one or more speakers installed on or around an S-MMS 18.

In one embodiment, the necessary speakers are integrated as part of the HMI and controlled by the HMI processor 808 (FIG. 8). Other embodiments may alternatively or additionally include visual, haptic, or biofeedback mechanisms to provide a corresponding feedback.

The alert manager 1440 may also alert the user to degraded systems that require maintenance to keep systems operational. One example of this is integration of LED lights on each sensor or associated with each sensor processor 814 (FIG. 8). In this example, the alert manager 1440 monitors the status of the sensors (e.g. by receiving a status signal from each sensor) and transmits a signal to each sensor LED when that sensor fails causing the LED to turn on and notify users and technicians of a failed sensor. In one example, the sensor status signal is either an on state (positive voltage signal) or an off state (no voltage). The alert manager 1440 may receive multiple types of status signals from the sensors and/or other devices of the S-MMS 18 and transmit one or more signals to one or more status indicators (e.g. single or multi colored LED or other visual, audio, or signal indicator) to cause to indicator to alert the user, technician, or other person as to the status of the sensor or other device. These "Clean Lights" or other indicators may also be clustered in a central display as part of the HMI 606.

S-MMS Pairing/Partnering with a Smart Device

Figure 15:
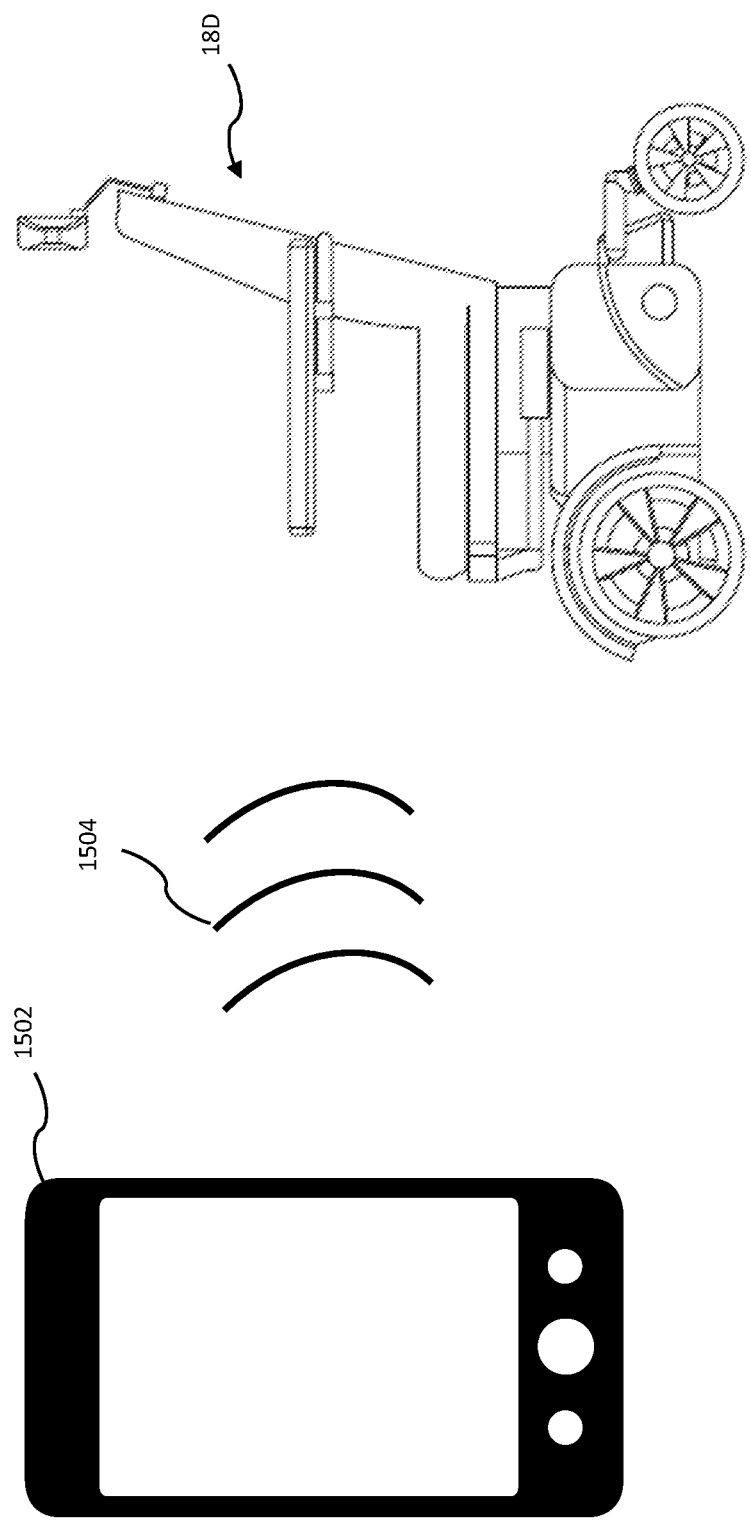
FIG. 15 depicts an embodiment of a mobile chair S-MMS in communication with a smart phone.

In one embodiment, illustrated in FIG. 15, the CNI function 1204 (FIG. 12) makes and/or manages wireless communication connections with one or more wireless systems available to transmit and receive (transceive) data relevant to a desired operation of a mobile chair S-MMS 18D. In one embodiment, a smart device 1502, such as a smart phone or smart tablet, communicates 1504 with the S-MMS 18D via the communication processor 816 (FIG. 8) of the S-MMS 18D through one or more of 802.11, Bluetooth, Bluetooth Low Energy (BLE), Near Field Communication (NFC), and/or Zigbee™, among others. These communications 1504 are typically predicated on a "just works" model, one that requires little interface with the device 1502, 18D and the underlying technology. The levels of security and privacy are device 1502, OS, and wireless service dependent.

When a smart device is connected to the S-MMS 18D, regardless of connection type, additional safeguards can be employed to ensure better levels of privacy. As a first example, 802.11 is a standard network protocol well known in the art. Higher level protocols or applications can be incorporated as desired. These protocols or applications can have capability for security, in particular security and access stacks in support of HIPAA requirements if any personal medical data needs to be collected or transmitted. These applications may be easy to use and portable.

With a focus now on Bluetooth, similar connectivity is available through a Bluetooth profile. Bluetooth profiles have been developed, produced, and maintained as standards. Some of these profiles define how devices can connect, for example, through the Lan Access Profile (LAP) that allows for what would otherwise look like an 802.11 networking connection. Another example is the Serial Access Profile. Other connections can be made through certain profiles for very specific activities, such as when connected to a vehicle. These include: Hands Free Profile, Audio Video Resource Control Profile, and Advanced Audio Distribution Profile, among others. Each of these profiles is designed to support certain systems for certain applications.

Bluetooth is somewhat more unique and therefore friendlier for the developer. Today there exists a set of device profiles designed to facilitate transmission and reception of medical device data. The APIs of this layer interact with the lower level Bluetooth Multi-Channel Adaptation Protocol (MCAP layer), but also performs Service Discovery Profile (SDP) to connect to remote Health Data Profile (HDP) devices and makes use of the Device ID Profile (DIP). This capability could be duplicated on the other protocols.

In a Bluetooth embodiment, and with a focus on security and privacy, the Bluetooth Special Interest Group (SIG) established a Medical Devices Working Group (MED WG). This group was formed to develop a profile that could provide this level of privacy, security, and interoperability between health device sources (such as blood pressure meters, weighing scales, and thermometers) and health device syncs (smart devices, such as PCs, PDAs, mobile phones, and displays) from different manufacturers. The work of the MED WG has resulted in the development of the HDP and the MCAP, which together fulfill this need.

Figure 16:
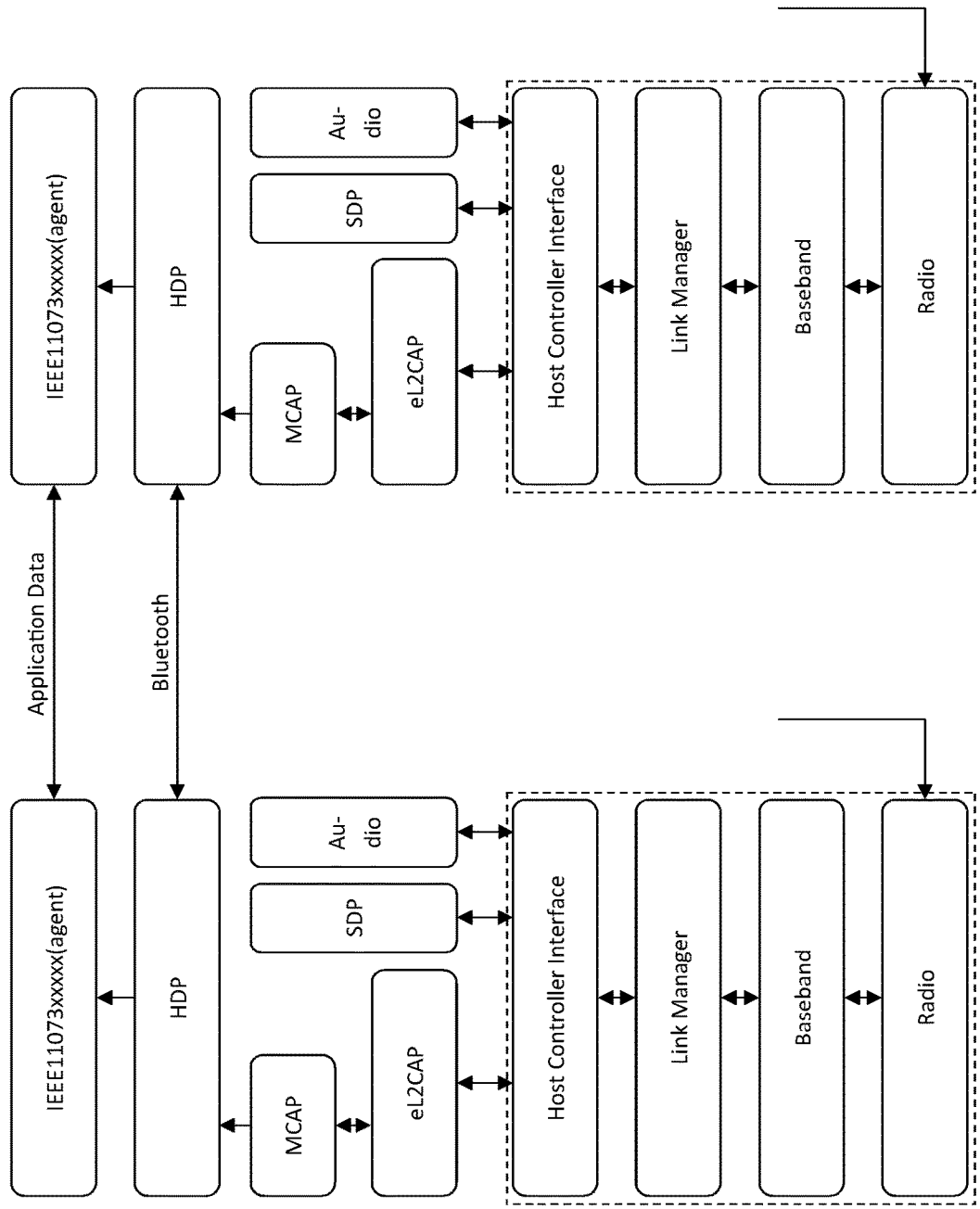
FIG. 16 depicts an embodiment of a HIPAA communication architecture for use with an S-MMS.

FIG. 16 depicts the Bluetooth HDP and defines an underlying wireless connection and protocol which may be used by an S-MMS 18 to communicate data between the S-MMS controller 210, other onboard systems or data (e.g. data from computer readable storage media 802, FIG. 8), and external devices (such as device 1502 of FIG. 15). In one example, the S-MMS 18 is paired via Bluetooth with the device 1502. For example, the S-MMS controller 210, communication processor 816, and\or other component of the S-MMS 18 pairs with the device 1502 via Bluetooth by initiating and/or accepting a secure Bluetooth connection with the device. Communications may be received and transmitted by the communication processor 816 (FIG. 8) and processed or generated by the CNI 1204 (FIG. 12) of the S-MMS 18 when communicating with another device (e.g. phone, tablet, computer, health device, etc.) via Bluetooth. Bluetooth HDP operates in conjunction with the ISO/IEEE 11073-20601 Personal Health Data Exchange Protocol (HDEP) and associated device specialization specifications to provide application level interoperability for a wide variety of personal health devices. The highest-level goals of the SIG are reducing reliance on cables and wires in order to give more freedom and possibilities to patients, healthcare workers, and users. Types of devices marketed today with which the S-MMS 18 can communicate as described above include pulse oximeters, blood glucose meters, and blood pressure monitors/devices, to name a few. Additional devices are identified below in Table 1.

In addition to the HDP, the SIG allows for the possibility of more than one device per user using a multi-channel adaption protocol (MCAP). The MCAP is designed to securely connect and manage multiple wireless medical data devices simultaneously. The S-MMS 18 uses MCAP and/or HDP via the CNI 1204 and communication processor 816 to communicate with wireless devices in some embodiments to meet a high level of medical data security needs can be met.

Smart Device with S-MMS Controller as Medical System

Figure 17:
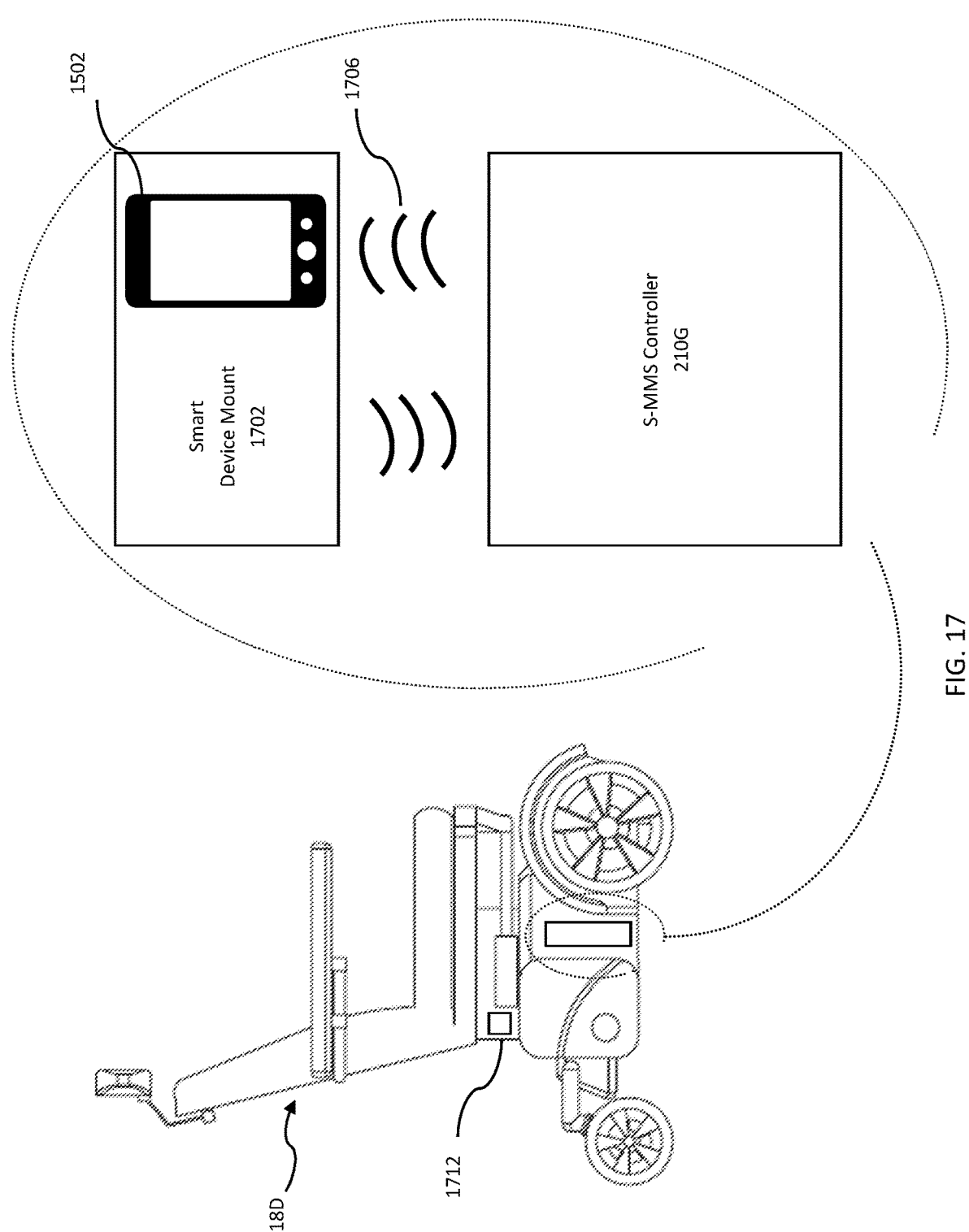
FIG. 17 depicts a smart device mount coupled to an S-MMS.

FIG. 17 depicts an embodiment of the S-MMS 18D wherein a smart device mount 1702 (AliMed—Therafin TEK Wheelchair Communication Device Holders, as an example) is affixed to an S-MMS 18D. A smart device 1502 is mounted in the smart device mount 1702 and communicatively coupled to the S-MMS controller 210G of the S-MMS 18D via a wireless connection 1706 (e.g. via Bluetooth pairing and communications). The wireless connection is established between a first wireless communication processor (e.g. communication processor 816 via the CNI 1204) on the S-MMS 18D and a second wireless processor on the paired smart device 1502. The first wireless communication processor 816 and second wireless communication processor establish secure connections between the S-MMS 18D and the smart device 1502. The processors implement the HDP profile stack and instantiate an MCAP for remote devices. A smart device, in some embodiments, includes a location determining system (LDS), such as a GPS receiver or device. In addition to the LDS, the smart device may include one or more of a micro-inertial device in the form of an accelerometer, rate sensor, or both for determining orientation of the smart device connected to the S-MMS 18D. Tracking applications, such as the FollowMee application, can be downloaded to the smart device 1502 and used to track the S-MMS 18D via GPS data or other location data received by the smart device from the S-MMS 18D (for example, from the SAC 902A-C via the communications processor 816) or on behalf of the S-MMS. The GPS or other location data collected by the tracking application may be transmitted to another device, e.g. the wireless communication processor 816 or processor 802 executing the S-MMS controller 210G, another mobile device, a secure server (hardware), or a computer via a wireless connection, to monitor the location and status of the S-MMS 18D. What is unique is the user's location data is treated and reported like medical data through the HDP and MCAP implemented by the communication processor 816 (FIG. 8) on the S-MMS 18D. The mapping of the user's location data can be done through a secure server and shared with only those authorized to receive the data. While the third party smart device mount 1702 is depicted on the side of the S-MMS 18D near the base in FIG. 17, it may be fixed to other locations. Additionally or alternatively, the smart device 1502 may be used in a similar manner when not attached to the S-MMS 18D via a device mount.

Automated Call for Help Feature: S-MMS System External Communications Example Motorized mobile system users may be unable to call for help if they have a problem. This could be due to an injury, lack of proper breath support, developmental disabilities that impede their communication skills, or any number of other physical restrictions or challenges. A simple accident could cause an S-MMS to tip. Because it is very heavy, a misjudgement of terrain may cause an S-MMS to sink and get stuck. There are a variety of disasters that an S-MMS user could encounter on any given day.

Figure 18:
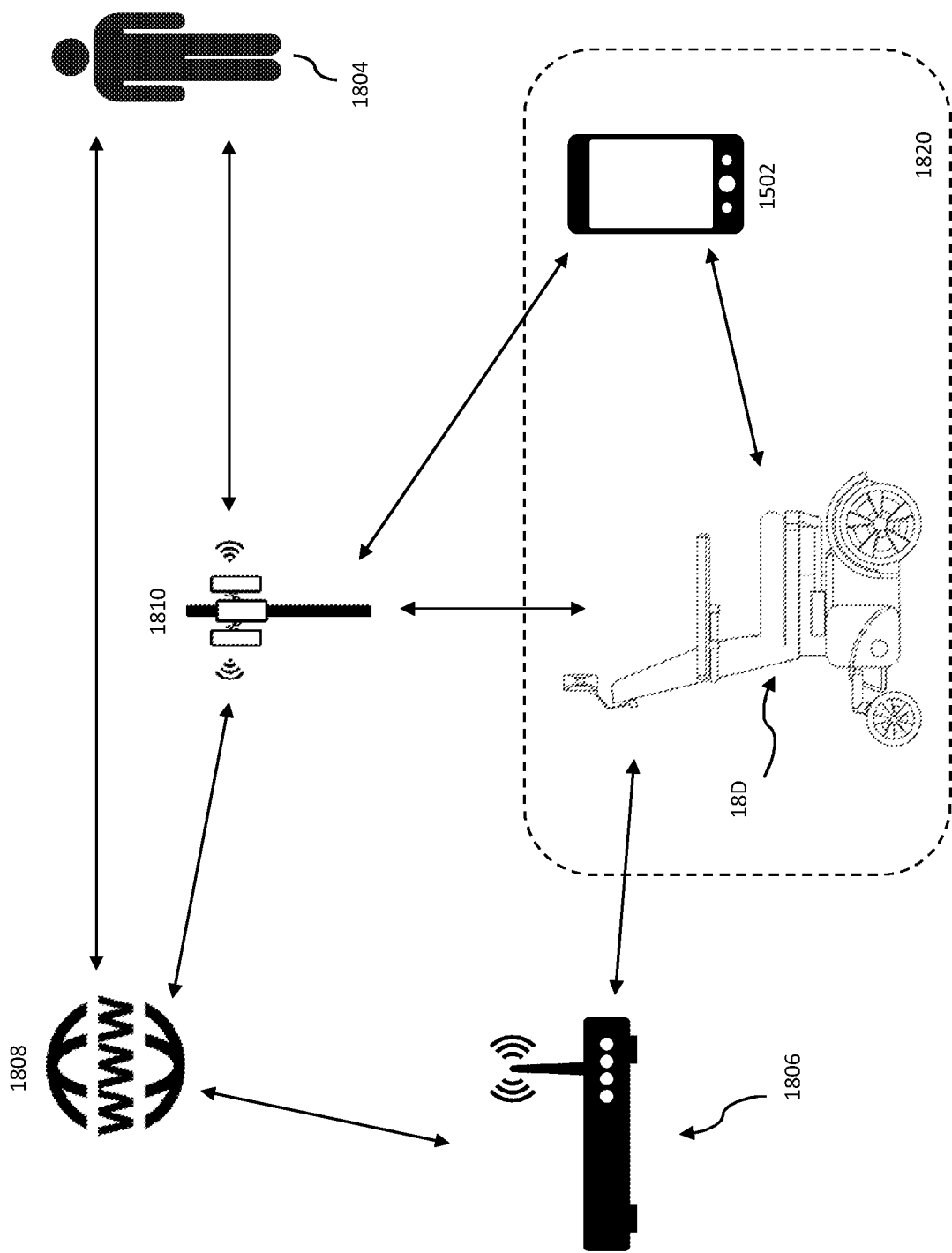
FIG. 18 depicts embodiments of an S-MMS with the ability to contact pre-identified caregivers.

The S-MMS 18D situational awareness controller 902 may incorporate a Call for Help feature that would send one or more of a notification, SMS text message or automatic video or audio call to one or more pre-programmed caregivers if the S-MMS situational awareness controller recognizes that it was having a problem for which it is programmed to respond with a response. FIG. 18 depicts multiple possible embodiments of an S-MMS 18D with the ability to contact pre-identified caregivers 1804. In one embodiment, a smart device 1502 is communicatively coupled to the S-MMS controller 210 of the S-MMS 18D via a wireless connection (e.g. via Bluetooth pairing and communications through the CNI 1204 and communications processor 816) in the manner previously described and depicted in FIGS. 15-17. The SAC 902 may transmit a command via a secure channel to an S-MMS application resident on the coupled smart device 1502 which causes the S-MMS application on the coupled smart device to use the external wireless cellular connection 1810 of the smart device to place a call or send a text message to one or more caregivers 1804 pre-programmed in the S-MMS application. In another embodiment, the S-MMS controller 210 may use one or more onboard communication processors 816 (FIG. 8) configured for cellular communication with a wireless service 1810 to place a call or send a text message to one or more pre-programmed caregivers 1804. In another embodiment, the S-MMS controller 210 may use one or more onboard communication processors 816 (FIG. 8) configured for Wi-Fi communication with a wireless router 1806 to place a call or send a text message using an online service 1808 such as Twilio which provides services that can exchange text and picture messages, place voice calls, and place video calls to mobile devices when addressed using an API provided by the service provider. The service 1808 may then contact one or more pre-programmed caregivers 1804. These different embodiments are not necessarily exclusive and may be combined so that a single S-MMS 18D is capable of selecting an appropriate communication approach based on one or more of minimizing cost to the user, the severity of incident, and data throughput needs of the preferred mode of communication.

The SAC 902 may initiate sending messages, as depicted in FIG. 18, indicating a dangerous event, a stuck chair, a low battery, etc. based on data available from the motor controller 604, the HMI 606, any of the S-MMS sensor reports 1206-1214 and/or S-MMS controller 210 functions such as navigation 1216, alerts determined by alert manager 1440, threats assessed by threat assessor 1428, states identified by user health manager 1410, or states within RTOS services 1002. In one example embodiment, if the SAC 902 identifies that HMI inputs are not resulting in motion consistent with expectations, the SAC 902 causes a message or other indicator to be generated to the user via the HMI 606 (e.g. via a screen, audio indicator, haptic feedback, or other output device) to prompt the user with the option to call for help. The user may accept by pressing a button, making a prescribed motion with a joystick, or providing other available HMI 606 inputs which are received by the SAC 902. Alternatively or additionally, if the motor controller 604 identifies a low battery, and the SAC 902 estimates that there is not enough battery remaining to get the user to a safe charging location, then the SAC 902 may cause a message to be dispatched to a local service provider for assistance.

In some embodiments, a mobile device may be used with the S-MMS 18D to share, store, transmit, modify, and/or manage data relative to the S-MMS 18D, the S-MMS user, and the environment. This pairing of the S-MMS 18D and smart device 1502 creates an enhanced S-MMS system 1820. The mobile device 1502 may communicate with the S-MMS controller 210 wirelessly (as described above via the CNI 1204 and communications processor 816) using short range communications, such as Bluetooth and near-field communications, or via wired communications through a wired communication interface on the S-MMS 18D coupled to the communications processor. For example, the wired communication interface may be a universal serial bus (USB) A-C interface, an RJ-45 interface or other interface to support internet protocol (IP) communications, or another wired interface, all of which are supported via the communications layer/interface 370. In some embodiments, data is first transmitted from the S-MMS 18D to a network device 1806, 1810 (e.g. by the S-MMS controller 210 via a wired communication interface, such as a modem 1806) before being transmitted to one or more other devices on the network using one or more network connections and/or protocols. A modem or other network adaptor on the S-MMS 18D may be configured to detect a device such as a mobile device, establish a connection such as link management protocol (LMP) connection with the device, and establish a secure data connection with the device, all of which is controlled by the CNI 1204 and communications processor 816. Additionally or alternatively, a modem or other network adaptor at a remote location may be configured to detect a device such as a S-MMS 18D, establish a connection such as link management protocol (LMP) connection with the S-MMS via the communications processor 816, and establish a secure data connection with the communications processor of the S-MMS. When a secure connection is established between two nodes (i.e. network device(s)/S-MMS), data may be securely transmitted through the network. In some embodiments, data may be transmitted through Global System for Mobile Communications (GSM), cellular, or other communication systems and/or protocols 1810. In some embodiments, the data may be transmitted by the S-MMS controller 210 via the communications processor 816 to a separate processor in a network (e.g. a hardware server or other computer) wherein the separate processor may be configured to operate on a public packet network. A public packet network (also known as a public data network) is a circuit- or packet-switched network that is available to the public and that can transmit data in digital form, such as the internet 1808. A public packet network may include one or more hardware servers which may be configured to receive, store, and retrieve data.

The Call for Help functionality may also allow a caregiver the ability to pinpoint the S-MMS 18D location in order to provide help as quickly as possible. In an embodiment, the S-MMS 18D location is known via a tracking application discussed above. In another embodiment, the S-MMS 18D location is known via the onboard GPS and inertial manager 1214 and/or navigation 1216 (FIG. 12) processes supported by one or more onboard GPS sensors/receivers 814E (FIG. 8). The ability to pinpoint the chair is always available through the tracking application, thereby providing increased security to the user and peace of mind for caregivers.

This tracking application functionality may also be utilized by MMS manufacturers, when authorized by a user, to dispatch service technicians or other assistance to the user as needed. Additionally or alternatively, a web application may be used to monitor the location of the S-MMS 18D.

Tip Alert as a Medical Event

Referring again to FIG. 17, in some embodiments, the S-MMS 18D has one or more micro-inertial devices 1712 that detect attitude changes. The micro-inertial devices 1712 transmit one or more signals to the S-MMS controller 210 either through the arbitration IAM 1202 or as part of the GPS and inertial manager 1214 data via navigation 1216 (FIG. 12). The signals from the one or more micro-inertial devices 1712 include attitude data that identifies an attitude or attitude change of the S-MMS 18D. The SAC 902C or 902D of the S-MMS controller 210 receives and processes the attitude data to determine the current attitude of the S-MMS 18D or any changes to its attitude. As an example, a 90-degree change of attitude will cause the detection of gravity by the micro-inertial device(s) 1712 on the x-axis of the S-MMS 18D if the S-MMS 18D is on one of its sides, or on the y-axis of the S-MMS 18D if it is on its front or back. In either case, the z-axis would read zero. However, if a rate sensor is used, the rotation will be detected by the rate sensor along one or more of the axes. These sensor reports can be used to sense and identify tipping of the S-MMS 18D. In the case of a power wheelchair S-MMS as an example, a tipping event may be treated as a health informatics event and therefore handled in accordance with appropriate standards. In one embodiment, the one or more micro-inertial devices, accelerometers, or other attitude, rate, or inertia determining sensors are mounted to the S-MMS 18D and communicate with the SAC 902C or 902D of the S-MMS controller 210 and/or a smart device 1502 paired to the S-MMS 18D (as previously disclosed) in accordance with the following, relevant protocols:

Personal Emergency Response Sensor 11073-10471—
        Health informatics—Personal health device communication—Device specialization—Personal Emergency Response Sensor Motion Sensor 11073-10471 Health informatics—Personal health device communication—Device specialization—Motion Sensor Fall Sensor 11073-10471 Health informatics—Personal health device communication—Device specialization—Fall Sensor Using a combination of LDS location, time, and attitude, a secure data report can be generated by the SAC 902C or 902D of the S-MMS controller 210 in the event that a tip is detected. This report may be handled in accordance with one or more of the standards listed above. In some embodiments, a key aspect of the S-MMS 18D is the use of signals and sensors associated with the user of the S-MMS by the S-MMS controller 210.

An S-MMS controller 210 may be configured to receive control inputs from an HMI and respond in a preconfigured way. It may also be configured to store sensor data related to the position and/or status of onboard system sensors.

Some embodiments of the S-MMS 18D are configured to receive data from sensors associated with the user of the S-MMS. When the sensor data relates to personal information, such as personal health data, it is stored and/or transmitted securely by the S-MMS controller 210 to protect the privacy of the user. Moreover, in order to transfer this data externally, such as to an associated smart device 1502, secure wireless protocols (e.g. Bluetooth HDP and MCAP) may be used by the S-MMS controller 210. In some embodiments, an additional wireless connection is used to connect the smart device 1502 and/or S-MMS controller 210 to a secure remote server and/or secure cloud server. In some embodiments, with each of the secure memory locations (either the memory 320 of the S-MMS 18D or the secure remote server and/or secure cloud server), access is limited to pre-authorized systems and individuals in order to protect patient privacy. With this in mind, the previously discussed data report on the tipping event may be transmitted and logged into a secure remote server designed to store information about the S-MMS 18D and/or its user. The data on the secure server may then be used by caregivers and other pre-authorized parties to monitor the life, health, and safety of the S-MMS user.

S-MMS Communication with Remote Servers and Services

Figure 19:
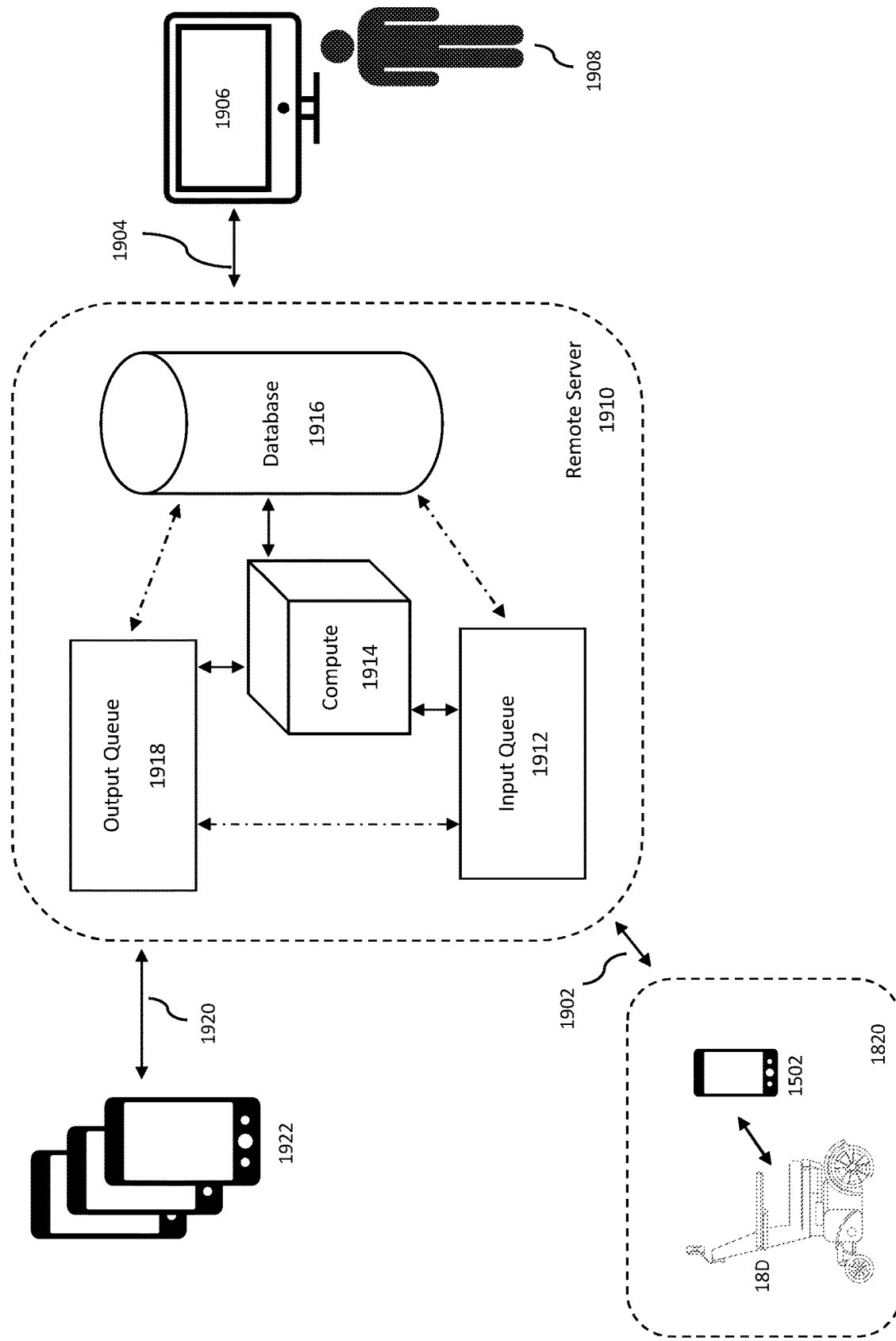
FIG. 19 depicts an embodiment of an S-MMS securely connected to a remote server.

FIG. 19 depicts an embodiment of a S-MMS system 1820 securely connected to a remote server 1910. In the depicted embodiment, a wireless processor either onboard the S-MMS 18D or associated with the S-MMS as a paired or connected wireless smart device 1502 is operably coupled to a second wireless processor via a secure wireless connection 1902, wherein the second wireless processor is configured to operate on a public packet network (see FIG. 18). The connection 1902 to the public packet network from the S-MMS system 1820 allows access to one or more remote servers 1910 configured to receive data from a secure memory on the S-MMS 18D and/or the secure memory on the associated smart device 1502 of the S-MMS system 1820. The received data may then be stored in a secure memory on the remote server 1910 wherein the secured, stored data is accessible to pre-authorized systems or pre-authorized persons.

In an embodiment, an S-MMS controller 210 retrieves a key (e.g. a code or security credential) from secure memory on a paired device 1502 over a wireless connection (secure in an embodiment). This key may be stored on a secure memory on the S-MMS 18D and is then transmitted to a remote server 1910. The key, provided by the paired device 1502, is used by the remote server 1910 compute engine 1914 or input queue service 1912 to authenticate the S-MMS 18D on the remote server 1910 and identify the S-MMS system 1820 with a unique, authorized user account. This key authentication authorizes the input queue 1912 to receive further messages transmitted from the S-MMS system 1820 to the remote server 1910 and/or associate those messages with a unique user account. Additionally or alternatively, the key authentication may authorize the output queue 1918 to send data to the S-MMS system 1820 for use by the S-MMS controller 210 on the S-MMS 18D and/or paired device 1502. In an embodiment, the paired smart device 1502 may be replaced by an alternative device configured to transmit or receive wireless signals such as an RF tag or BLE beacon.

In an embodiment, a pre-authorized system may be a web interface 1906 accessed through an internet connected device wherein a pre-authorized user 1908 logs in using security credentials and may view a history of events and other data associated with a particular S-MMS user or the S-MMS of that user. In another embodiment, the web interface 1906 may be used to communicate with the S-MMS user or modify or add data to the S-MMS users' unique data file. Data transmitted to the web interface 1906 may be delivered via a secure sockets layer (SSL) connection.

In one embodiment, the remote server 1910 may be configured to accept, process, store and complete specific actions based on messages from an S-MMS system 1820. FIG. 19 depicts a remote server 1910 configured to receive incoming messages from an S-MMS system 1820 via a secure connection 1902. Messages may be sent from the S-MMS system 1820 when a particular event takes place (e.g. on a tipping event as previously described), at state events (e.g. at startup of the device), and/or at pre-scheduled times (e.g. at midnight each night). These incoming messages are received by an input queue 1912 of the remote server 1910. Messages from the input queue 1912 may then be sent to one or more of a compute engine 1914, a database 1916, and an output queue 1918. The compute engine 1914 may compare data included in incoming messages from the input queue to predefined rules. Additionally or alternatively, the compute engine 1914 may work as a filter to associate individual messages with unique user accounts prior to storing data in a database 1916. The compute engine 1914 may also, based on the content of a received message, push alerts or action requests to an output queue 1918. The output queue 1918 may be a subscription/publication service that, when activated, sends alerts to internet connected devices 1922, such as an S-MMS users' caregiver's smart device. Alerts may be sent as text messages, voice messages, voice calls, or video over a cellular and/or Internet Protocol (IP) network 1920, including the internet. In some embodiments, the services 1912-1918 on the remote server 1910 may be executed on one or many individual server instances that work together to complete tasks as a single unit on one or more hardware processors. Additionally or alternatively, multiple other remote server architectures are possible to accomplish the intended functionality. As a non-limiting example, dashed-dot lines have been included to show alternative connections that may be enabled in some embodiments. Additionally, the compute function may include more advanced machine learning logic, such as a neural network, in some embodiments. Diagnostics and other basic server components have been left off of the diagram for the purpose of clarity.

Examples and Applications of the Previously Described Systems with a Focus on Health Infomatics Pairing of an S-MMS system 1820 via secure, high speed wireless connections 1902 to one or more remote servers 1910 (as disclosed previously) allows S-MMS users continuous connectivity with caregivers, assistance services, and family. This continuous connectivity may be configured so that a user must initiate it. Additionally or alternatively, connections may be triggered based on rules and/or conditions identified by caregivers, technicians, and/or other approved individuals. In some embodiments, one or more caregivers may be notified by the remote server 1910 and/or S-MMS controller of the S-MMS 18D in the event that the S-MMS stays docked for charging outside of expected hours that were previously indicated as the S-MMS being in use. In the case of a mobile chair user, this could indicate a need for assistance.

Another exemplary use of secure communications is the ability for an S-MMS user to get real-time assistance from a remote party that can see and hear both the user and the S-MMS 18 surroundings.

One exemplary embodiment includes remote access for an educational assistant to a mobile chair user with a disability to take notes for the user, read signage that may be confusing, or otherwise provide real-time assistance to the S-MMS user. Remote access for the educational assistant may be provided by one or more of the wireless connections depicted in FIG. 18 with the video and audio provided by one or more of a paired smart device 1502 (FIG. 18), onboard cameras or microphones, image and audio sensors embedded in the S-MMS (e.g. 814 FIG. 8, 814D FIG. 10), or audio/video sensors wirelessly paired to the S-MMS 18D via CNI 1204 (FIG. 12). In some embodiments, logs of these sessions may be stored in onboard memory (820 FIG. 8) by the CNI 1204 or other process of the S-MMS controller 210E or 210F or pushed to a remote server (1910 FIG. 19).

In another example, remote access is provided for a caregiver, such as a physical therapist, for medical check-ins and/or to walk the mobile chair user through stretches and exercise both with and without the assistance of the power chair. In one embodiment, a pre-authorized physical therapist 1908 may log into a remote, internet connected device 1906 or 1922 (FIG. 19). Via an internet service 1808 (FIG. 18), or a remote server 1910 (FIG. 19), the physical therapist may request to establish a session with the S-MMS 18D, such as via the CNI 1204. In one embodiment, the user may choose to accept or deny the requested session by indicating their selection on the S-MMS 18E HMI 606 or via the HMI on a paired smart device 1502 (FIG. 15). If accepted by the user, the S-MMS controller 210D-F will select data from the motor controller 604, HMI 606, SAC 902C-D, as well as data streams from onboard sensors (e.g. image sensor reports 1210) to be securely transmitted to the remote user via the CNI 1204. S-MMS 18D motions may be instigated by the user and/or the remote party. In some embodiments, the S-MMS controller 210E or 210F may accept inputs received from the physical therapist as equivalent to inputs received from the onboard HMI 606.

In another example, remote access is provided for training of a ATV MMS driver. In one example, an experienced or professional driver could use the S-MMS 18 data stream to provide guidance and training to a less experienced S-MMS driver. In this embodiment, the smart device 1922 (FIG. 19) of the professional driver may be provided (via the means previously disclosed) with a video stream from one or more cameras located on or around the S-MMS 18 overlaid with a simulated set of gages and steering/throttle positions of the S-MMS 18 for viewing on the smart device.

The collection of health data is a complicated and now regulated matter. As previously disclosed, the S-MMS 18D will allow for integration of data from multiple sensors in (e.g. ingestible sensors), on (e.g. wearable), and around (e.g. smart home devices) the S-MMS user. In some embodiments, a communication processor 816 (FIG. 8) on the S-MMS 18D is configured to establish secure connections to communicate data between the S-MMS 18D and one or more other wireless devices. The wireless devices associated with a communication processor 816 (FIG. 8) may communicate using one or more of cellular, 802.11, Wi-Fi, 802.15, Bluetooth, 802.20, and WiMAX. The data received via these wireless connections may be received by the S-MMS 18D as CNI 1204 via the arbitration IAM 1202. Additionally or alternatively, sensor data may be received from wired or wireless sensors onboard the S-MMS 18D as user sensor reports 1212 via the arbitration IAM 1202 (FIG. 12). In either case, the data is made available to the S-MMS controller 210D-F and may be stored in secure memory 820 (FIG. 8). Much of the data collected in this manner can be classified as health informatics information.

The IEEE has established a Data Exchange Specification under ISO/IEEE11073-20601 and generally refers to the generation and collection of data as Health Informatics—Personal Health Data Communication. Table 1 below is a listing of twenty-nine identified data generating sources for the IEEE 11073 requirement. IEEE 11073 is herein incorporated by reference in its entirety.

TABLE 1

| | | |
|---|---|---|
| Basic ECG (heart rate) | 11073-10406 | Health informatics - Personal health device communication - Device specialization - Basic ECG (heart rate) |
| Blood Pressure Monitor | 11073-10407 | Health informatics - Personal health device communication - Device specialization - Blood pressure monitor |
| Body Composition Analyzer | 11073-10420 | Health informatics - Personal health device communication - Device specialization - Body composition analyzer |
| Body Thermometer | 11073-10408 | Health informatics - Personal health device communication - Device specialization Body thermometer |
| Body Weight Scale | 11073-10415 | Health informatics - Personal health device communication - Device specialization Body weight scale |
| Carbon Monoxide (CO) Sensor | 11073-10471 | Health informatics - Personal health device communication - Device specialization - Carbon Monoxide (CO) Sensor |
| Cardiovascular Fitness and Activity Monitor | 11073-10441 | Health informatics - Personal health device communication - Device specialization - Cardiovascular Fitness and Activity Monitor |
| Contact Closure Sensor | 11073-10471 | Health informatics - Personal health device communication - Device specialization - Contact Closure Sensor |
| Enuresis Sensor | 11073-10471 | Health informatics - Personal health device communication - Device specialization - Enuresis Sensor |
| Fall Sensor | 11073-10471 | Health informatics - Personal health device communication - Device specialization - Fall Sensor |
| Gas Sensor | 11073-10471 | Health informatics - Personal health device communication - Device specialization - Gas Sensor |
| Glucose Meter | 11073-10417 | Health informatics - Personal health device communication - Device Specialization - Glucose meter |
| Independent Living Activity Hub | 11073-10471 | Health informatics - Personal health device communication - Device specialization - Independent Living Activity Hub |

TABLE 1-continued

| | | |
|---|---|---|
| International Normalized Ratio (INR) Monitor | 11073-10418 | Health informatics - Personal health device communication - Device Specialization - International Normalized Ratio (INR) Monitor |
| Medication Dosing Sensor | 11073-10471 | Health informatics - Personal health device communication - Device specialization - Medication Dosing Sensor |
| Medication monitor | 11073-10472 | Health informatics - Personal health device communication - Device specialization - Medication monitor |
| Motion Sensor | 11073-10471 | Health informatics - Personal health device communication - Device specialization - Motion Sensor |
| Peak Flow Monitor | 11073-10421 | Health informatics - Personal health device communication - Device specialization - Peak flow monitor |
| Personal Emergency Response Sensor | 11073-10471 | Health informatics - Personal health device communication - Device specialization - Personal Emergency Response Sensor |
| Property Exit Sensor | 11073-10471 | Health informatics - Personal health device communication - Device specialization - Property Exit Sensor |
| Pulse Oximeter | 11073-10404 | Health informatics - Personal health device communication - Device specialization - Pulse oximeter |
| Smoke Sensor | 11073-10471 | Health informatics - Personal health device communication - Device specialization - Smoke Sensor |
| Step Counter based on 10441 | 11073-10441 | Health informatics - Personal health device communication - Device specialization Step Counter based on 10441 |
| Strength Fitness Equipment | 11073-10442 | Health informatics - Personal health device communication - Device specialization - Strength fitness equipment |
| Switch Sensor | 11073-10471 | Health informatics - Personal health device communication - Device specialization - Switch Sensor |
| Temperature Sensor | 11073-10471 | Health informatics - Personal health device communication - Device specialization - Temperature Sensor |
| Usage Sensor | 11073-10471 | Health informatics - Personal health device communication - Device specialization - Usage Sensor |
| Water Sensor | 11073-10471 | Health informatics - Personal health device communication - Device specialization - Water Sensor |

Adherence to health informatics standards and best practices, as disclosed above, will allow data generated by S-MMS 18 and connected devices to efficiently be pulled into new or existing patient electronic health records (EHRs). Users, caregivers, and/or doctors may directly select system-generated data to include in standard EHRs such as certain medical records and/or discharge summaries. These EHRs may use additional standards such as the Clinical Document Architecture (CDA) or Consolidated Data Architecture (C-CDA).

In some embodiments, user, environment, and/or health data may be transmitted between an S-MMS controller 210 (which includes all of S-MMS controllers 210-210F) and other networks, systems, devices, and servers (see FIGS. 18 and 19). The S-MMS controller 210 may receive one or more data sets relative to one or more sensors located in, on, and around the S-MMS via wired or wireless connections via the arbitration IAM 1202 (FIG. 12). Additionally or alternatively, the S-MMS controller 210 may receive data or one or more data sets from external sensors and/or information services (i.e. weather stations, traffic lights, other MMSs, among others) via internet connected services 1808 (FIG. 18). These data and data sets may be separated according to level of security needed in transmittal, or by other methods as determined by user preferences and/or preset data security requirements. For instance, on the one hand, environment data such as local weather is publically available and therefore requires little to no security in its transmittal. On the other hand, user data related to health conditions and other personal information requires higher levels of security in transmission.

The data may be stored in one or more of local memory or remote memory (either the memory 320 of the S-MMS 18 or the secure remote server and/or secure cloud server 1910). To store the data remotely, it is transmitted from the S-MMS by the communication processor 816 to another storage location. In some embodiments, this data is securely transmitted via direct wired cable connection. In some embodiments, this data is transmitted wirelessly by the S-MMS controller 210 via the communication interface 370, such as to a mobile device.

Temperature, Moisture, Urine, and Perspiration Monitoring

Figure 20:
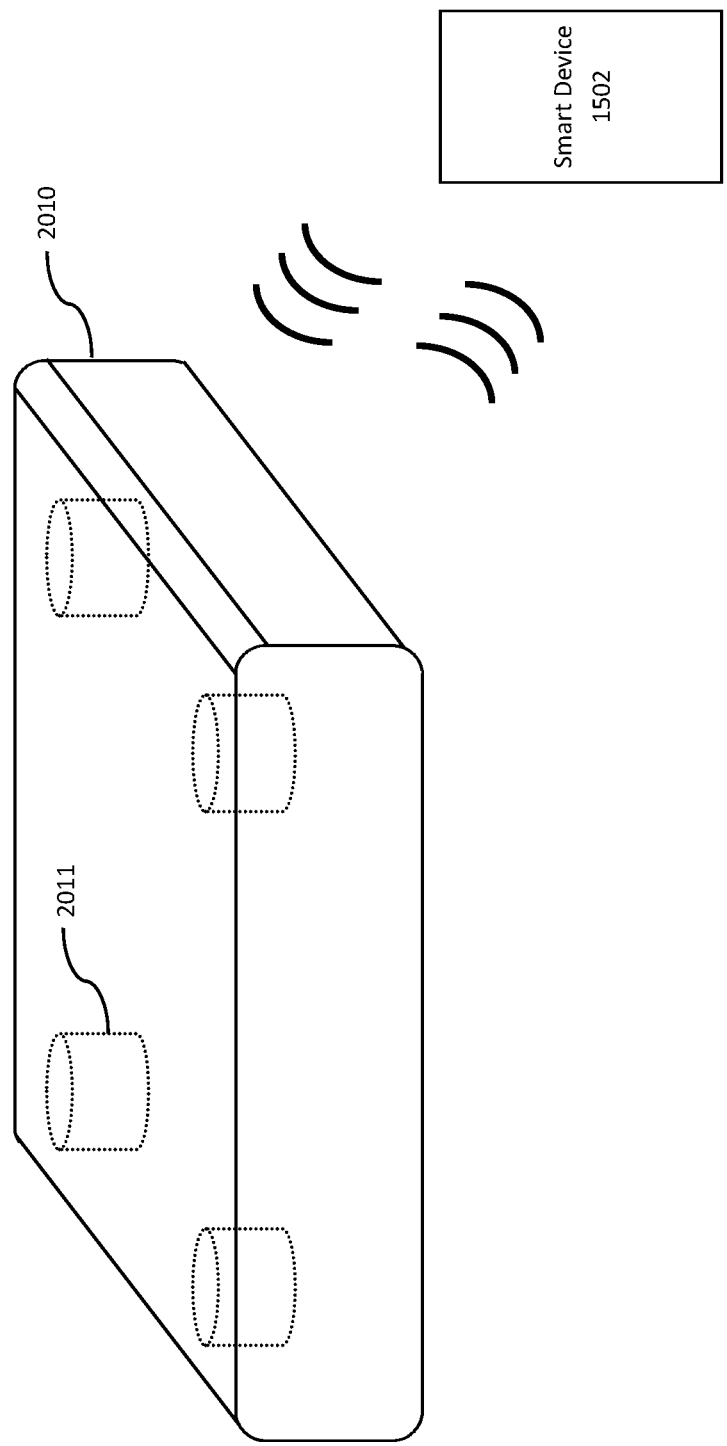
FIG. 20 depicts an embodiment of one or more sensors in a seat in communication with a smart device.

In some embodiments, one or more sensors may be included on, in, and/or around the S-MMS 18 to gather user data. FIG. 20 depicts an embodiment wherein moisture sensors 2011 are included in the seat 2010 of a S-MMS 18. Multiple built-in sensor deployments are envisioned as part of S-MMS 18. However, there is a need to go beyond just built-in or from-the-manufacturer sensor integrations. Technology is changing rapidly and, therefore, an S-MMS 18 must allow rapid integration of new technologies and sensors over the course of the S-MMS lifecycle. For this purpose, a smart device 1502 may be securely coupled to an S-MMS 18 through Bluetooth, as described above. The smart device 1502 can obtain and log bio-medical data, and other user data, received from sensors located on and around the S-MMS 18 and/or its user. The data may be received directly by the smart device 1502 from the S-MMS 18 or a server, such as by a software application operating on the smart device that is associated with the S-MMS, its user, or the user's caregiver. An example of such an application is a phone or tablet application downloaded from the Apple App Store, Google Play, or The Windows Store that can be associated with the S-MMS 18 (e.g. via pairing the phone to the S-MMS via Bluetooth), from a server as described above by entering a user name and password and/or other security data, from a user account linked to the application, or otherwise. Additionally or alternatively, the sensor data may be may be received by the S-MMS controller 210 and passed to the smart device 1502 via the CNI 1204 (FIG. 12) by a communication processor 816 (FIG. 8, such as by the above-described application and other above described methods). The data collected from the seat 2010 is securely stored in one or more of the S-MMS 18 memory 820 and/or smart device 1502 memory. Additionally or alternatively, the data may be securely transmitted out to a user or caregiver as previously disclosed (FIG. 18 and FIG. 19).

Rules and/or preferences may be established for when to send an alert. These rules may be stored, managed, and enforced remotely by the compute engine 1914 on a secure, remote server 1910 (FIG. 19). Additionally or alternatively, the rules and preferences may be stored, managed, and enforced on an application operating on the smart device 1502. In this example, the smart device application optionally received sensor data generated by one or more sensors, processes the sensor data according to the rules and/or preferences, and either generates an alert on the smart device (e.g. via vibration, audio/sound, light via the LED or otherwise, or via an image, alert, or video on the smart device's screen) or transmits a signal to the S-MMS 18 to cause the alert manager 1440 (FIG. 14) or other process of the S-MMS controller 210 to generate one or more alerts as described above. Alerts may be sent to the user or caregiver in accordance with the standards for the corresponding sensor type established in Table 1 shown previously (e.g. Temperature Sensor, 11073-10471).

Wireless communication of data over Bluetooth may provide common, secure communication between the S-MMS 18, the smart device 1502, and one or more sensors. For Bluetooth communication between the S-MMS 18 and smart device 1502, the MCAP may be implemented as part of the Bluetooth stack running on the communication processor 816 and used to collect data from the sensors. The MCAP may also be implemented for communication with one or more sensors of the S-MMS 18 (e.g. 2011). The HDP may be implemented as part of the communication protocol to handle transmission to an off-board server for collection and disposition. Additionally or alternatively, secure, paired BLE via GATT may be used by some embodiments.

Figure 21:
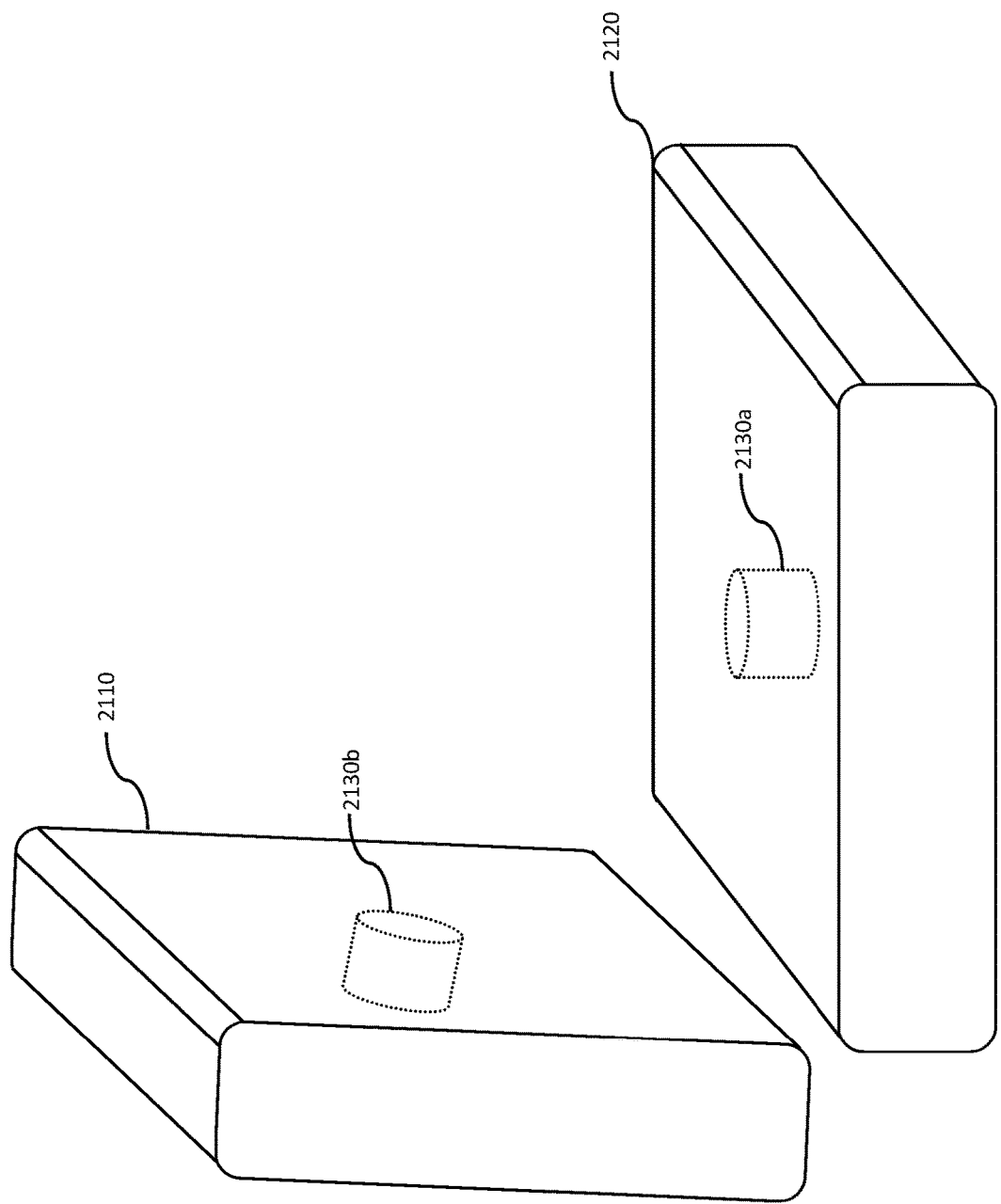
FIG. 21 depicts example sensors in a seat back and/or bottom cushion of an S-MMS.

FIG. 21 illustrates an embodiment of a user temperature tracking system for an S-MMS 18. In some embodiments of an S-MMS 18 temperature tracking system, one or more temperature and humidity sensors 2130*a*,*b* such as those made by Sensirion, may be embedded in one or more of a seat back 2110 and a seat bottom 2120 of an MMS. MMS drivers are particularly susceptible to many conditions that may be correlated with increased occupant temperature. Several examples of these conditions include pressure sores due to sitting in a fixed position for an extended period of time, heat exhaustion, and cognitive impairment (particularly for mobile chair S-MMS users with complicating medical conditions such as CP). The temperature and humidity sensors 2130*a*,*b* transmit one or more signals to the S-MMS controller 210 by the above-described methods and mechanisms. The S-MMS controller 210 determines the temperature and/or humidity (e.g. moisture) of the seat back 2110 and/or bottom 2120 and may initiate one or more actions based on the temperature and/or humidity (e.g. transmit a message to a caregiver or cause an audible or visual alert). The user temperature data may be processed and transmitted in accordance with Body Thermometer standard 11073-10408.

In some embodiments, two or more sensor readings may be combined by the S-MMS controller 210 to increase confidence in determining a given condition. As an example, in order to differentiate between rain, perspiration, sweat, and urine when wetness is detected (e.g. by humidity sensor 2130*a*), readings from one or more of a salinity and pH sensor may be combined with a general moisture reading. Sweat has a low pH, usually in the range of 4.0 to 4.5, and high salinity. Urine, on the other hand, has a relatively high pH (4.5-8.0) and relatively low salinity. By combining data readings from one or more of pH and salinity sensors with a general moisture sensor, the S-MMS controller 210 or related server 1910 can better interpret moisture as rain, a physiological response to external conditions (e.g. temperature, stress, etc.), or incontinence, among other possibilities. For example, user perspiration may be indicated if a low pH reading is received in combination with a positive moisture reading. This information may then be stored and/or analyzed by the S-MMS controller 210 and related server 1910 either locally or remotely.

User Presence and Heart-Rate Monitoring

Figure 22:
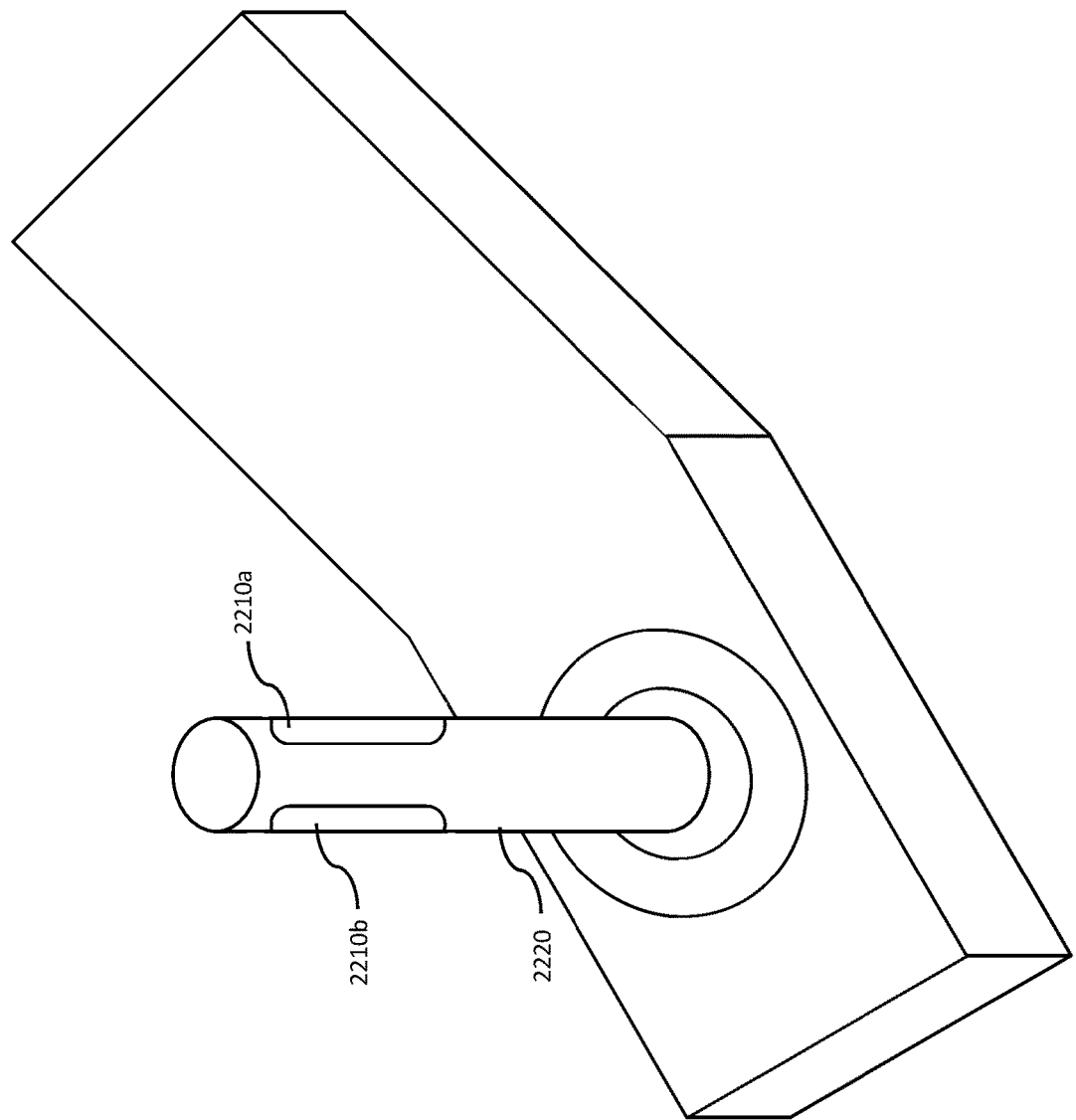
FIG. 22 depicts an embodiment of a heart rate tracking joystick for an S-MMS.

FIG. 22 illustrates an embodiment of a heart rate tracking HMI for an S-MMS 18. By placing at least two conductive regions 2210*a*,*b* on an S-MMS 18 steering interface, such as a joystick controller 2220, the user presence and heart rate can be tracked accurately while the user is steering. User presence may be established by a continuity check between the two conductive regions. In one embodiment, a resistor divider scheme is implemented to detect contact of a user's finger tips with the conductive pads. Heart rate may be calculated based on measuring the electrical activity associated with the heart that can be detected through the skin. In an embodiment, voltages received from a resistor divider scheme are amplified and fed to a processor which filters the received signal to reject high frequency noise and then runs a peak detection algorithm to identify unique heart beats. In one embodiment, the processor may be configured as a sensor processor 814 (FIG. 8) and may communicate with the S-MMS controller 210 as a user sensor report 1212 via the arbitration IAM 1202 (FIG. 12). Reference is made to health informatics measurement of heart rate and user presence (referencing ISO/IEEE 11073, Basic ECG (heart rate) 11073-10406 and Contact Closure Sensor 11073-10471), which is incorporated fully herein by reference.

In addition to providing valuable health information on the user, S-MMS controller 210 may also be configured to not move the S-MMS 18 unless a heart rate (or user electrical connection on both conductive regions 2210*a*,*b*) is sensed by the system. Mobile chair users report frustration with accidentally bumping the steering interface on their mobile chair, causing the mobile chair to move. In this example, the two conductive regions 2210*a*,*b* are sensors, and they transmit signals to the S-MMS controller 210 indicating one or both conductive regions is engaged (e.g. being grasped) by a user. The S-MMS controller 210 processes these signals and determines when the joystick 2220 is being fully grasped by the user. The S-MMS controller 210 then determines based on the sensor signals received from the two conductive regions 2210*a*,*b* whether or not to allow movement of the S-MMS 18 mobile chair. The S-MMS controller 210 allows movement of the S-MMS 18, in this example, when the S-MMS controller 210 determines the user is grasping both conductive regions 2210*a*,*b* of the joystick 2220. Requiring a complete grasp of the joystick, with confirmation through a user conductive electrical connection on both conductive regions 2210*a*,*b*, would allow rejection of many non-intentional inputs to the joystick.

User Weight Monitoring

Figure 23B:
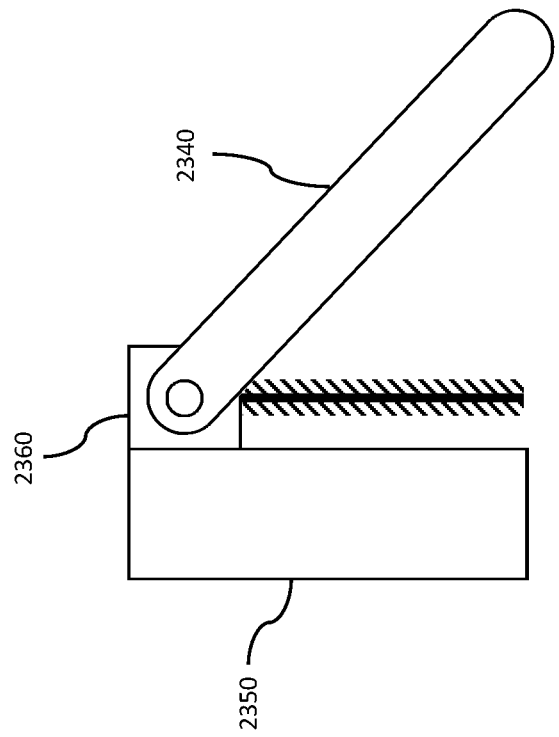
FIG. 23B illustrates one or more mounts with embedded strain sensor(s) used to connect a seating assembly mechanism or support to a mobile chair S-MMS chassis.
Figure 23A:
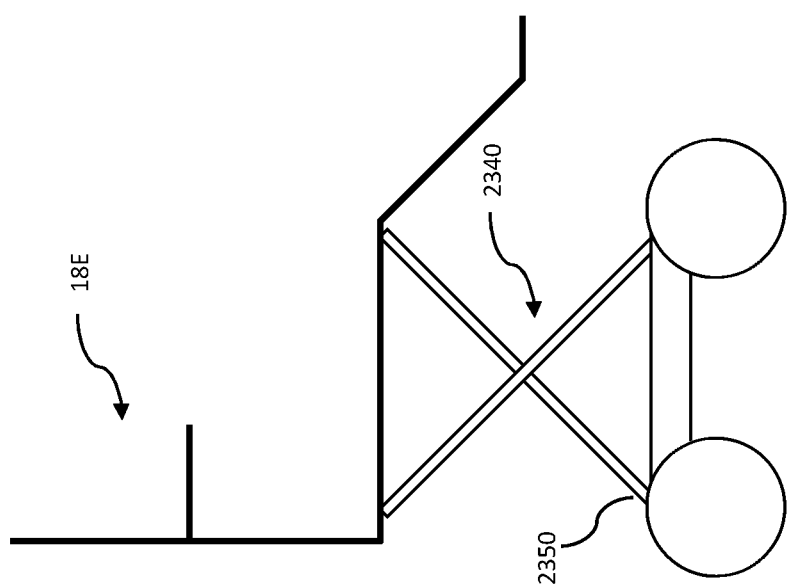
FIG. 23A illustrates one or more strain sensing bolts utilized to mount a post or actuator from a seat assembly to a mobile chair S-MMS chassis.

In some embodiments, the S-MMS 18 may include the ability to calculate a user's weight. FIGS. 23A and 23B depict two exemplary embodiments of the mobile chair S-MMS 18E with strain sensors used in the connection between the seating assemblies and chassis of the S-MMS 18E. In some embodiments, these sensors allow the S-MMS controller 210 to determine the weight of the occupant. FIG. 23A illustrates an embodiment where one or more strain sensing bolts 2360 are utilized to mount a post or actuator from the seat assembly 2340 to the mobile chair S-MMS chassis 2350. The bolts determine changes based on mechanical strain. These include one or more of capacitive, resistive, and inductive sensors. These bolts may be used, for example, to determine occupancy and weight of an occupant. FIG. 23B illustrates an embodiment where one or more mounts with embedded strain sensor(s) 2360 are used to connect a seating assembly 2340 mechanism or support to the mobile chair S-MMS chassis 2350. As an example, the force applied at the seat assembly/chassis interface can be measured (e.g. using the strain sensing provisions previously disclosed) and transmitted to the S-MMS controller 210 as the measured weight as described above) the fixed weight of the S-MMS 18E seating components can be subtracted from the measured weight by the S-MMS controller 210 to result in the user weight, and the user weight can then be reported out to a paired smart device 1502 or a secure server 1910 using the above-described methods and mechanisms, in some embodiments. In this approach, the collection of data through from embedded sensors, the execution algorithms within the S-MMS controller 210 for occupant weight determination, and the communication with the smart device 1502 or secure server 1910 are done in a secure manner. In an embodiment, the communication with the smart device 1502 may use Bluetooth and implement the HDP. Additionally or alternatively, secure, paired BLE transmission via GATT may be used by some embodiments. The presence of a user may also be determined by detecting user weight in the seat of the S-MMS 18E. Fluctuations in user weight may also be tracked in some embodiments.

Integration of Wireless User and Environmental Sensors

In an embodiment, the S-MMS 18 includes a communication system, comprising a wireless transceiver to communicate with a second wireless transceiver on an external system, wherein the wireless transceivers communicate via one or more of dedicated short-range communications or an ad hoc network. The wireless transceiver of the S-MMS 18 may be part of the communications layer/interface 370, receive and transmit communications from its communications processor 816, and receive and transmit communications to its communications processor for processing by the S-MMS controller 210 or CNI 1204. Similarly, the second wireless transceiver of the external devices will receive and transmit communications to its wireless processor for processing and receive communications from its wireless processor for transmission to the S-MMS 18.

Figure 24:
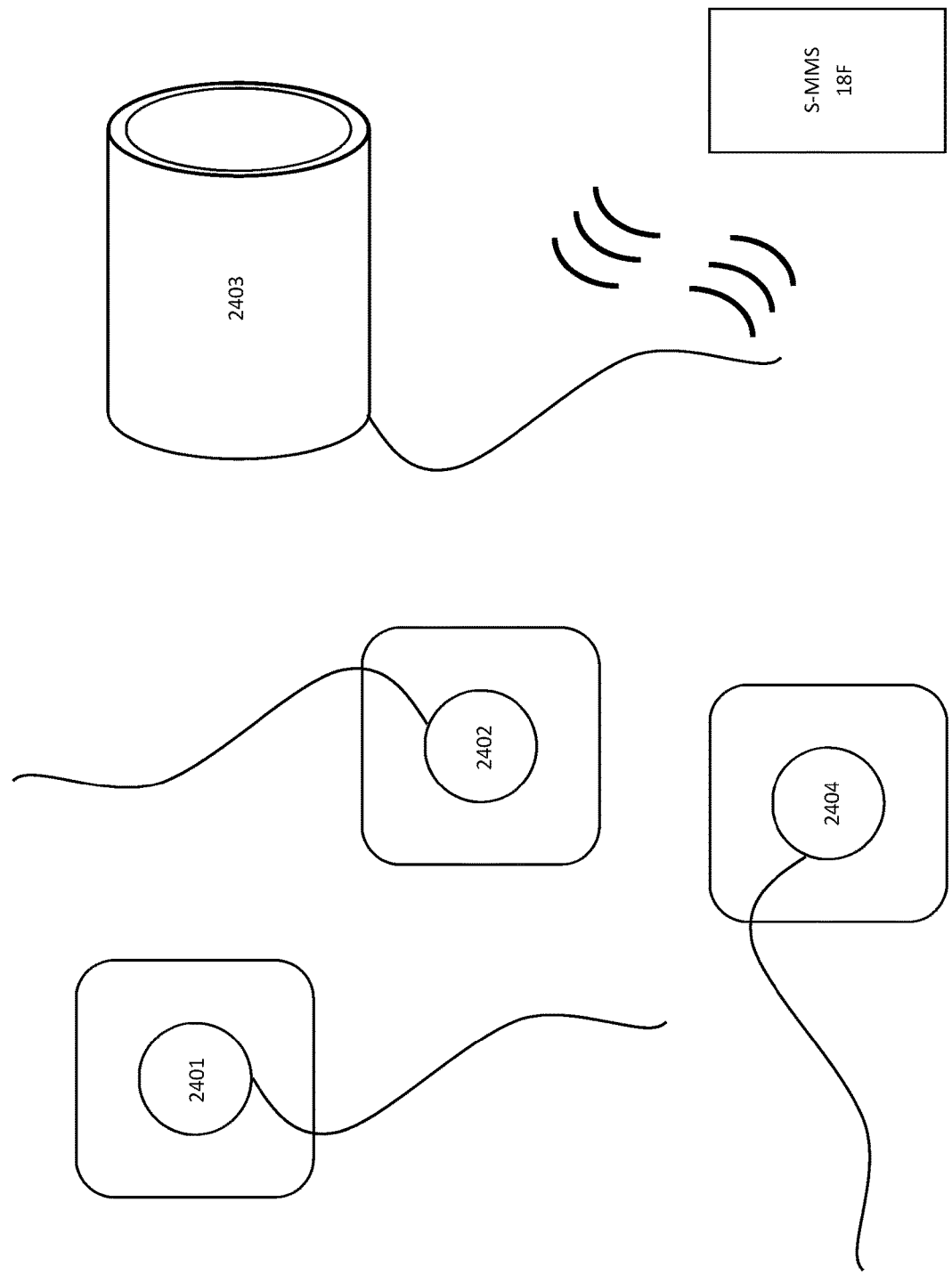
FIG. 24 depicts health data generating devices in communication with an S-MMS.

FIG. 24 depicts several health data generating devices in communication with the S-MMS 18F. In some embodiments, one or more sensors 2401-2404 are securely connected Bluetooth-based sensors which connect using the MCAP and HDP to the S-MMS controller 210. The sensors 2401-2404 can be one or more of blood pressure, glucose, blood oxygen levels, heart rate, respiration rate, perspiration, salinity, pH, bioelectrical impedance, electrodermal activity, galvanic skin resistance, temperature, and other such sensors capable of generating data related to the comfort and/or health of a user. User sensitive data may be securely collected and may be transmitted through the MCAP and HDP stack by the S-MMS controller 210 to a compliant server. Rules engines may be established on the S-MMS controller 210 as part of the SAC 902 (including SAC 902-902C) to send commands to one or more components of the S-MMS based on sensor data or otherwise, such as commands to the motor controller 604 (e.g. activation of an onboard cooling system for the user if perspiration is detected), commands to the HMI 606 (e.g. user alerts or input requests), or commands to off board systems via CNI 1204. Additionally or alternatively, rules may be established for the user on a remote server 1910 (FIG. 19). Data from the sensors 2101-2104 may be transmitted to the remote server as described above, and, based on the processed sensor data, the remote server may transmit information regarding comfort level and/or health back to the user or caregiver as previously disclosed in FIGS. 18 and 19 in accordance with the IEEE rules disclose in Table 1. Additionally or alternatively, secure, paired BLE transmission via GATT may be used by some embodiments.

Internet of Things Integration

Referring to FIG. 25, home automation is a rapidly evolving technology that meshes smart devices into an automated home experience that reacts to the presence and commands of the occupants. For mobile chair S-MMS users, home automation creates a home environment over which they can have better control without installing specialized assistive devices. Enabling the command of home features like lights, doors, media, curtains, and locks through home automation gives access to those devices through means that are accessible to people of all abilities. Home automation means a more independent, more accessible life for mobile chair users and individuals with disabilities.

Mobile chair navigation can be hindered by darkened rooms and locked doors, and the location of controls for things like curtains and lights that may not be conveniently located. The control location may be located behind furniture, at the opposite end of a hallway, or there may be multiple controls in a small space that would require time-consuming and precise navigation to reach. In addition, physical or cognitive impairments may inhibit or significantly slow the operation of the controls. A S-MMS 18 with the ability to control devices or trigger home automation events creates a responsive, accessible home that enables and speeds the control of home features.

In one example, the S-MMS 18G may communicate with an in-home smart automation device, such as the Nest thermostat and a smart lighting controller, to determine where the user is within their house and/or control the smart automation device. For example, The S-MMS controller 210 may broadcast via CNI 1204 its location data (calculated by navigation 1216) or another signal to the other authorized devices in the home. The other signal may be particular to one or more smart automation devices or generic to cause the one or more smart automation devices to activate one or more pre-configured actions or settings (e.g. light or temperature levels, music, television/videos, blinds, etc.) based on the received signal. This broadcast may use non-secure internet-of-things protocols previously disclosed. This allows the user to activate lights and heating/cooling within their house simply by entering (e.g. where the smart automation device is configured to activate one or more pre-configured actions or settings upon receiving the S-MMS 18G location data or other signal generated by the S-MMS controller to activate the corresponding action or setting of the smart automation device). Additionally, lights may be turned on and off as the user enters and exits rooms in a similar manner, as depicted by FIG. 25. The disclosed functionality may be further assisted by onboard sensor reports such as light sensors and/or temperature sensors embedded in the S-MMS 18G.

Events may be preprogrammed on one or more home automation devices based on signals from the S-MMS 18G or may use logic based on location of the S-MMS 18G, time of day, etc. The HMI 606 on the S-MMS 18G may also be used to control or trigger home automation devices by causing the S-MMS controller 210 to take actions. For example, the HMI 606 of the S-MMS 18G might be a control pad that has one or more buttons or inputs designated as one or more actions that trigger one or more events or settings in whichever room the S-MMS 18G is located. As an example, a user may navigate into the living room and push the action button of the HMI 606, triggering the S-MMS controller 210 to send a wireless signal using the CNI 1204 and an onboard communications processor 816 which causes the lights and TV to come on. Then the user may navigate to the bedroom, push the same or different action button of the HMI 606, triggering the lights on, a motorized harness that moves to the side of the bed, and music to start playing.

In some embodiments, the S-MMS 18G also may integrate with sensors located in the vicinity of the S-MMS 18G as previously disclosed. This pairing with nearby devices allows unique behavior for users in distress. As a non-limiting example, if the S-MMS controller 210 detects an elevated heart rate via a heart rate monitor (e.g. FIG. 22) onboard the S-MMS 18G, the S-MMS controller 210 may set a distress state and notify help as previously disclosed to a pre-authorized caregiver (e.g. via the alert manager 1440 or otherwise generating an alert or notification; see example discussion of tipping and FIG. 18). As part of the message sent to a pre-authorized caregiver, the S-MMS controller 210 may pair with a nearby Nest Cam via WiFi (as an example) and stream video of the user to the pre-authorized caregiver using one or more of a streaming web service 1808 or a forwarding service on a remote server 1910.

Communications with Vehicles, Vehicle Infrastructure and Other S-MMS

Figure 26:
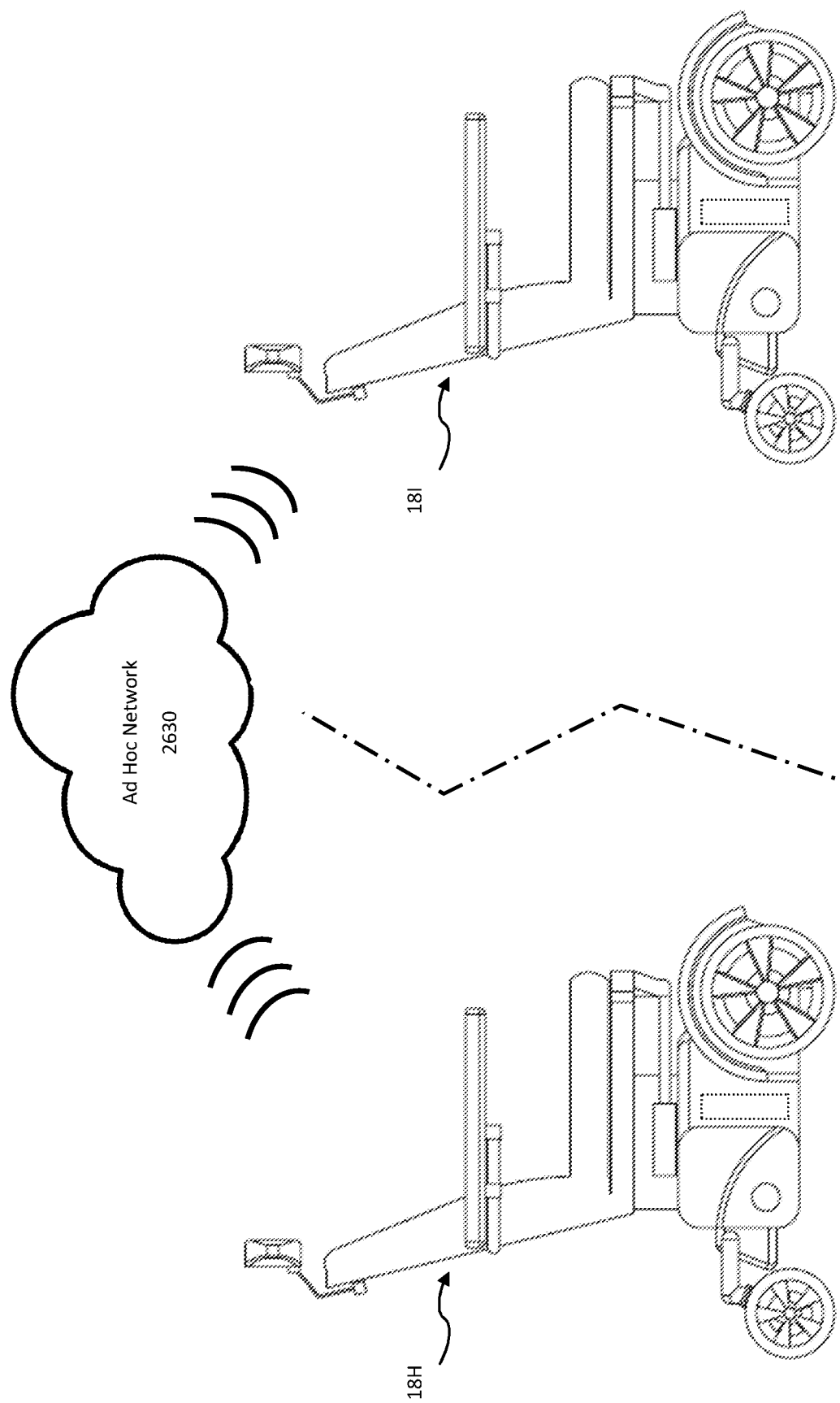
FIG. 26 depicts two mobile chair S-MMSs in communication with each other via an ad hoc network.

FIG. 26 depicts two mobile chair S-MMSs 18H and 18I in communication with each other via an ad hoc network. In some embodiments, the CNI 1204 process uses one or more onboard communication processors 816 operably configured with a wireless transceiver on the S-MMS 18H-I in support of Vehicle-to-vehicle (V2V) and Vehicle-to-everything (V2X) communication with wireless transceivers on other V2V and V2X systems. V2V is a technology designed to allow automobiles to communicate to each other. V2X allows communication of information from a vehicle, via wireless transceiver, to a second vehicle that may affect the second vehicle, and vice versa. It is a vehicular communication system that incorporates other more specific types of communication as V2I (Vehicle-to-Infrastructure), V2V (Vehicle-to-vehicle), V2P (Vehicle-to-Pedestrian), V2D (Vehicle-to-device) and V2G (Vehicle-to-grid). V2X communications systems form a dedicated short-range, wireless ad hoc network 2630 on the roads. In an embodiment, two S-MMS 18H and 18I are configured to communicate with each other over a V2X network.

V2X communication is based on WLAN technology and works directly between vehicles or the infrastructure, which form a vehicular ad-hoc network, as two V2X transceivers come within each other's range. Hence V2X communication does not require any infrastructure for vehicles to communicate, which promotes safety in remote or little developed areas. V2X has low latency and the ability to communicate instantly. V2X transmits messages known as Common Awareness Messages (CAM) and Decentralized Notification Messages (DENM) or Basic Safety Message (BSM). The data volume of these messages is very low. Messages may contain a range of content including the identity, type and kinematic states of the entity containing each V2X transceiver. The radio technology is standardized as part of the WLAN IEEE 802.11P family of standards and known in the US as WAVE (Wireless Access in Vehicular Environments) and in Europe as ITS-G5, both of which are incorporated herein in their entirety. As a further embodiment with the above initiatives in view, the communication layer/interface 370 of the S-MMS 18H-I is equipped with an 802.11P transceiver that operates on a nationwide network that enables communications between vehicles and roadside access points or other vehicles, and the S-MMS controller 210 is configured to process such communications and generate such communications, such as via the CNI 1204.

As was previously discussed, WAVE or IEEE 1609 defines numerous protocols and messaging formats for the communication initiatives. What has not been considered in these initiatives is the use of the 802.11P system by users of non-automobile systems, and in particular this case, an S-MMS 18H-I equipped with an 802.11P transceiver.

Figure 27:
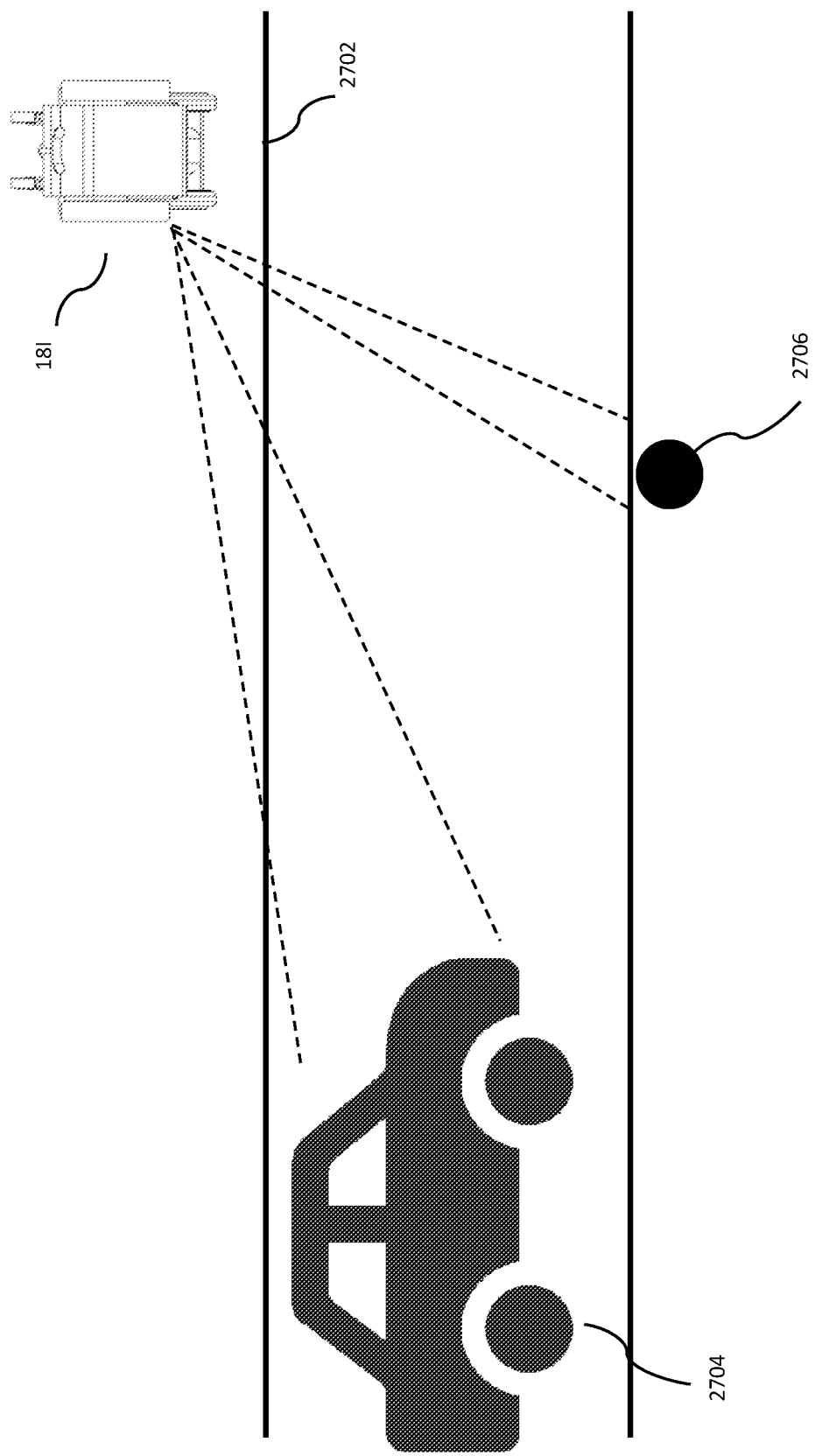
FIG. 27 depicts an S-MMS equipped with an 802.11P transceiver.

The CNI 1204 is responsible for managing communications as well as cooperative data exchanges. FIG. 27 depicts the user of an S-MMS 18I equipped with an 802.11P transceiver and the CNI 1204 configured to manage 802.11P communications. In this way, a secure communication system is created comprising a vehicular ad hoc network 2630 for exchanging secure messages. In this ad hoc network, a first security manager is located with a portable transceiver, which is physically coupled to one or more of the S-MMS 18H/I, linking data for transmission off-board the S-MMS to a second processor and second security manager connected to the vehicular ad hoc network 2630, wherein the vehicular ad hoc network is coupled to vehicles and vehicle infrastructure.

Currently, most traffic lights at street intersections operate according to a fixed setting. However, in reality, vehicle flow rates of the directions at intersections are not always equivalent. As a result, a traffic light at a first roadway may turn red when no car is driving on the crossing roadway, or remain in red when all cars on the crossing roadway have passed the intersection. With the addition of the V2X capability, it is anticipated that traffic lights in the future will be able to dynamically operate according to vehicle flow rates; however, the concept of adaptive flow rates have not anticipated a S-MMS 18I equipped with a V2X transceiver and configured to assist the user in safely navigating the roadway.

As a first example, the S-MMS 18I approaches a traffic signal 2706. At a cross walk 2702, the 802.11P transceiver on the S-MMS 18I picks up the signals from the traffic light 2706. The CNI 1204 receives the signals from the traffic light 2706 via the 802.11P transceiver and transmits the signal to the S-MMS controller 210, which processes the signals to determine a message must be sent indicating the direction the S-MMS 18I is traveling and the anticipated crossing time and generates the corresponding message. The CNI 1204 receives the message from the S-MMS controller 210 and transmits the message via the S-MMS 18I 802.11P transceiver. In other embodiments, a second message will be transmitted by the S-MMS 18I (via the S-MMS 18I components described above) when the roadway has been successfully traversed.

In another example, the user exits their own vehicle in a parking lot at a mall, and now must traverse the parking lot to enter the mall. The 802.11P transceiver equipped S-MMS 18I will start transmitting a message (as described above) indicating there is an S-MMS 18 in the parking lot at a certain location, moving a certain direction in an effort to enter the mall. This message is picked up by V2X equipped vehicles 2704 in the parking lot, putting the drivers of these vehicles on notice of the S-MMS user. Further, as a vehicle 2704 approaches, warning messages can be transmitted by the S-MMS 18I such that an audible or haptic alarm is sounded to the driver. As with the first example, the 802.11P transceiver equipped S-MMS 18I can control traffic lights in the mall parking lot or report unsafe conditions for the user if need be.

In a further embodiment of V2X, and as a follow on to the CNI discussion above, a smart home may be equipped with 802.11P transceivers as well. These transceivers are dedicated short range communications devices by design and are functionally designed for data exchange without much overhead. In one example, the user has an elevator in the home, the elevator needs to be summoned from another floor, the user indicates which floor they are on and which floor they wish to travel to via the HMI 606 on the S-MMS 18I, this information is transmitted by the 802.11P equipped S-MMS 18I in a message in the manner described above to the elevator, the elevator communication device receives the message, and the elevator processing device processes the message to dispatch the elevator, open the door, and wait for the user to load. Once loaded, the user only needs to wait for the elevator to traverse to the desired floor and open the door. This example works well with a user that has controls in only a single location in the elevator and allows for the user to load and not to have to worry about pressing a key for operation.

In some embodiments, with the rapid advent of autonomous driving vehicles, it is expected that vehicles in the future will indeed drive autonomously. The vehicles may be equipped with WAVE 802.11P as part of that system. A user that uses an S-MMS 18I may use the 802.11P equipped S-MMS 18I to generate a message to summon a driverless vehicle to a mall entrance from a parking spot to be picked up or dispatch the vehicle to a parking spot.

User Identification and Unique User Profiles

As previously disclosed, the S-MMS controller 210 may be processing ePHI relating to the user and storing ePHI in system memory 320. Additionally or alternatively, the S-MMS controller 210 may be communicating ePHI data to external sources such as external servers 1910. By HIPAA requirements, this data must be encrypted at rest and secured in transit. In addition, access control protocols are required to limit the accessibility of ePHI to pre-authorized individuals. A data access control strategy is needed in order for the previously disclosed system architecture and communication strategies to comply with HIPAA requirements for ePHI handling. Creating individual user profiles allows for a robust access control strategy and opens up new possibilities for MMS features.

At initial setup, each S-MMS 18 may be configured with a unique user profile that informs the S-MMS controller 210 of the individual user's baseline capabilities, preferences, and information. The user profile may be stored in onboard memory 320. Additionally or alternatively, the user profile may be stored on a remote server 1910. In some embodiments, user data and/or S-MMS data for a user profile may be gathered over time and used to update a unique user profile. In some embodiments, data may be saved to a user's profile where it may be accessed by a user, caregiver, third party, and/or by the S-MMS controller 210 or related server 1910 in future analyses. In some embodiments, the analyzed data may be sent to a caregiver by the S-MMS controller 210 or related server 1910 when attention may be needed.

In some embodiments, the S-MMS controller 210 uses the user data in the user profile to learn about the user and to adapt to the user accordingly. In some embodiments, the user data in the user profile may include aspects such as reaction time and skill. Along with user data, information about the S-MMS 18 may be gathered and stored in the user profile, including make and model and information regarding any associated accessories. The user profiles may be stored externally to the S-MMS 18 at a remote server 1910 associated with the S-MMS 18, on an associated smart device 1502, or on another electronic key and available for import when the user switches systems, for instance when they are traveling. The ability to port a user profile allows for simple, quick, seamless, and comfortable transitions between different S-MMSs 18.

Figure 28:
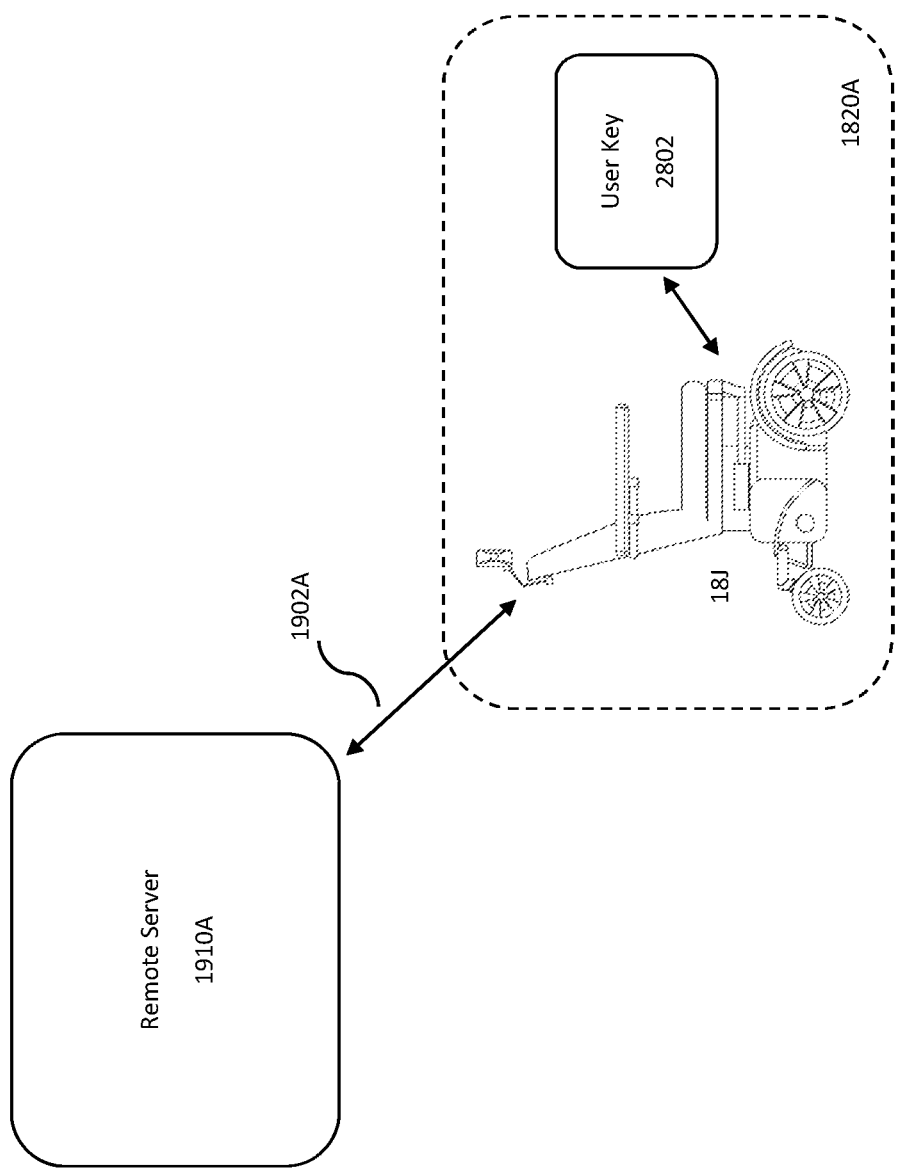
FIG. 28 depicts an embodiment of an S-MMS which receives a user key.

FIG. 28 depicts an embodiment of an S-MMS 18J which receives a user key 2802. Presence of a user key 2802, when received by the S-MMS 18J via one or more onboard communication processors 816, may allow the S-MMS controller 210 to access an onboard user profile stored in memory 320, access user data in a user profile stored on a secure remote server 1910A and write to either memory locations 320, 1910A. Where and how user data is stored and retrieved may be determined by user preferences and settings. The user key may be transmitted from one or more of a smart device 1502 configured to provide a preconfigured access code, an electronic key (such as a memory stick) which physically connects to the S-MMS 18J and provides an access code, or a wireless device configured to communicate with the S-MMS controller 210.

In addition to security, use of the user profile, and associated key, opens new possibilities for S-MMS users. In one example, a user profile contains data about the user (e.g. weight, other physical or cognitive characteristics of the user that would be relevant to an S-MMS or its operation, reaction time, and/or a numeric indicator of skill), user preferences, data identifying functionality and capabilities of an S-MMS based on a user, such as speed limitations, drive and steering limitations based on HMI input, seat position, sensor calibrations, user-preferred joystick or other HMI calibrations, user reaction time, and/or other S-MMS and user data. The user decides to fly to visit a friend or relative. It is decided that the user's normal S-MMS 18 is a larger and heavier chair that is impractical, too costly, or simply too complicated to deal with while traveling. In this case, the user may be transferred to a simpler folding and less complex chair to travel with. When the user arrives at the destination, an S-MMS 18J rental chair is provided. The user uses their smart device to couple to the new S-MMS 18J. Once connected, the user profile is requested from a remote server 1910 (e.g. by the S-MMS 18J rental chair or smart device) and loaded into a memory 320 of the new S-MMS 18J by the remote server and used to configure the new S-MMS controller 210 such that its functionality and behavior is now identical to their home S-MMS.

In an embodiment, the user key 2802 is provided to the S-MMS 18J rental chair via a secure Bluetooth connection 1504 from a paired smart device 1502 associated with the S-MMS user. In an example, the user profile is logged into the secure memory of a smart device 1502, such that when connected, the file is automatically transferred to the new S-MMS 18J. In another example, a second S-MMS 18J is equipped with features and capabilities not within the user's skill set. These additional capabilities are locked off for the duration of the use by the second S-MMS's S-MMS controller 210, based on the restrictions associated with and stored in the user profile. A caregiver or other pre-authorized individual may be presented with a personal identification number (PIN) or other access provision by the smart device 1502, the HMI of the second S-MMS 18J, or otherwise to access these features if the care giver felt the user could either learn the new features safely or had a past experience with the features such that the user would remain safe maneuvering in and around objects and other people.

In some embodiments, an important element of an S-MMS 18J is the integration of a smart device 1502 such as a smart phone or tablet into an integrated system 1820A. But, some users may not have the ability effectively use or obtain a smart device. For these users, a suitable alternative key may be needed to access basic features of some embodiments of the S-MMS 18J and associate their individual user profile with the S-MMS 18J they are using. For these users, Bluetooth, near field communication, radio frequency (RF) technology, and other alternatives may be used to communicate the user profile or an access code from a device to the S-MMS 18J. In an embodiment, the electronic key 2802 is a short-range RFID tag encased in a bracelet or wearable which transmits a unique alphanumeric code when excited by a properly configured transceiver at the request of the S-MMS controller 210.

Figure 29:
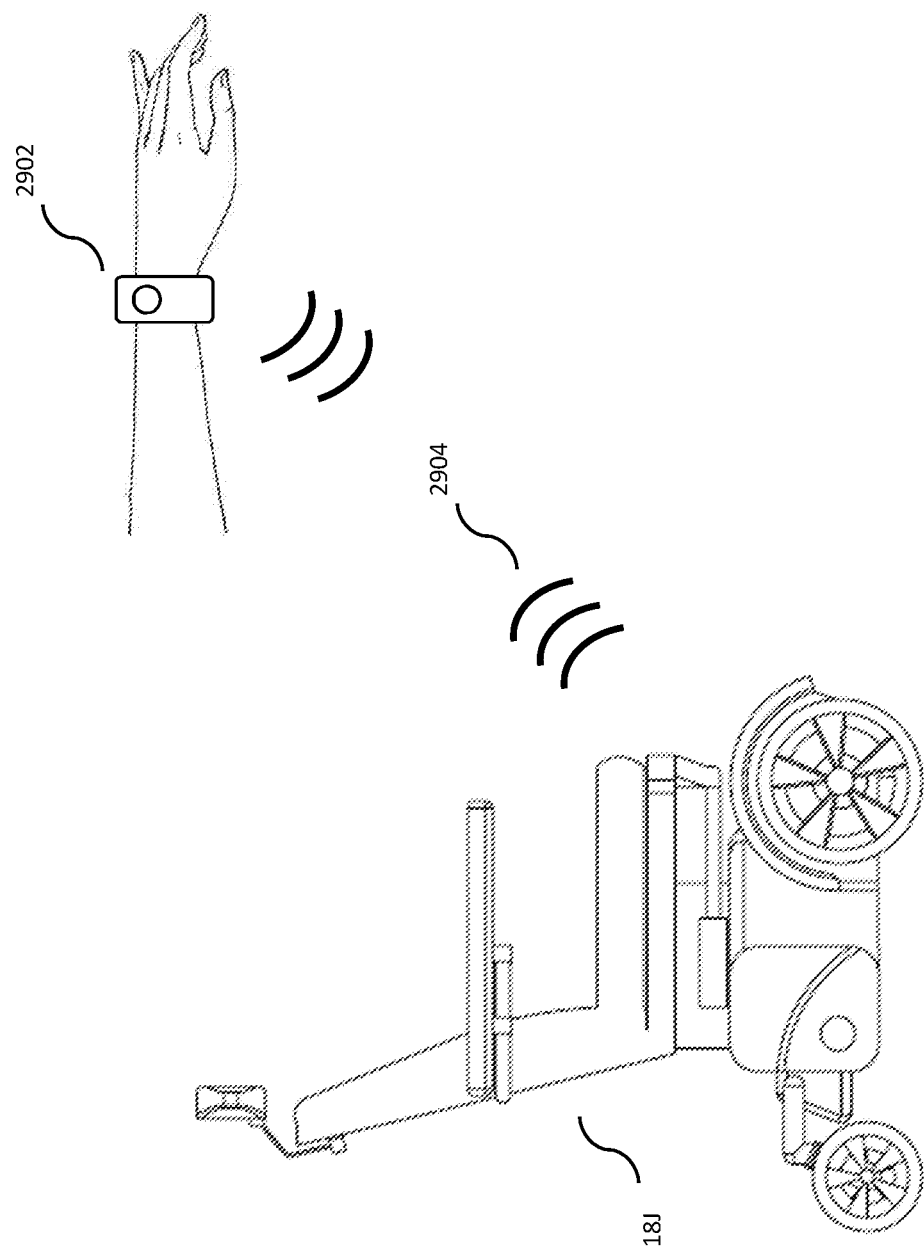
FIG. 29 depicts an embodiment of a user key in which a user may wear a device with an embedded RF transceiver.

FIG. 29 illustrates an embodiment in which a user may wear a device such as a wrist band, necklace, ring or other accessory 2902 with an embedded RF transceiver. The RF transceiver may be passive or active, with active transceivers allowing longer-range communication 2904 but requiring a power source such as a battery. When a user with a compatible wearable 2902 uses the S-MMS 18J, the wearable 2902 may act as the key 2802 to the S-MMS 18J. User profile information may be stored locally on the wearable device 2902 itself or communication between the wearable device and the S-MMS 18J may cause the S-MMS to retrieve a user profile matching a code from the wearable device from a remote server or other memory (as described above). In an embodiment, the RF transceiver previously described may be replaced with a Bluetooth Low Energy (BLE) transceiver.

Managing Data and Maintaining User Customization

The ability to select and/or characterize specific data sets from bulk data collected by health infomatics sources associated with the S-MMS 18 is a function of a proposed secure architecture. The rapid pace of change in technology is outpacing the medical establishments' ability to qualify new technologies as valid diagnostic tools. In some embodiments, current heart rate monitors integrated into a smart watch do not provide data at a quality level acceptable for use in medical records; however, this data may be of a quality level sufficient to be used to notify caregivers to check on a patient. Alternatively or additionally, it may only be useful to the user of the S-MMS 18 for personal improvement, tracking workout outcomes, or triggering certain S-MMS 18 actions such as reminders on the HMI 606.

In some embodiments, a user, technician, or caregiver, may associate a particular device or sensor to one or more select quality and/or functional groups so that the S-MMS 18 can properly offer the data in different modes of operation and/or for visibility to different end users. In one embodiment, a $3^{rd}$ party activity monitor may be wirelessly connected to the S-MMS 18 (either directly through the CNI 1204 or via an associated smart device 1502). The activity monitor may be a consumer activity monitor that is not validated for medical use and is intended only for self-improvement use by the user. In this scenario, a pre-authorized individual may use a software application on a smart device 1502, 1922 or a web interface on a web connected device 1906 to select the activity monitor and assign it to a quality group. This quality group assignment is then stored as part of the previously disclosed user profile. Additionally or alternatively, the sensor may be assigned to a quality group and viewed via the S-MMS 18 HMI 606. A non-limiting example of possible quality groups may include:

Validated Medical Data Source.
Non-validated Medical Data Source.
Self-improvement Data.

Sensors and data may also, in some embodiments, be characterized by the individuals who need access to the data. A non-limiting example of possible functional groups may include:

Data for S-MMS General Functions.
Data for S-MMS Safety Critical Functions.
Data for Caregiver.
Data for Therapist or Doctor X.
Data for MMS Technician.
Data for Study X.

The ability to securely store and robustly group the health infomatics data is expected to increase the pace of science in the art and provide for construction of a more complete picture of user health. The S-MMS 18 will allow deployment of new, promising technologies rapidly to the target population. At first, the data will be integrated as a nice-to-have feature or data source and may be grouped simply as Self-improvement Data and/or Data for Study X. As the science validates use of the data, it may graduate to be used for control of S-MMS 18 functions (by the S-MMS controller 210 and remote server compute engine 1914), and eventually with more vetting included as a Validated Medical Data Source and used to control S-MMS 18 critical safety functions on the S-MMS controller 210. Additionally or alternatively, specific therapists, doctors, and/or other parts of a user's support team may choose to opt in and out of channels that the user enables for them based on what data offers the most value and/or as science validates or invalidates use of different data sets.

Using Cloud Data

Figure 30:
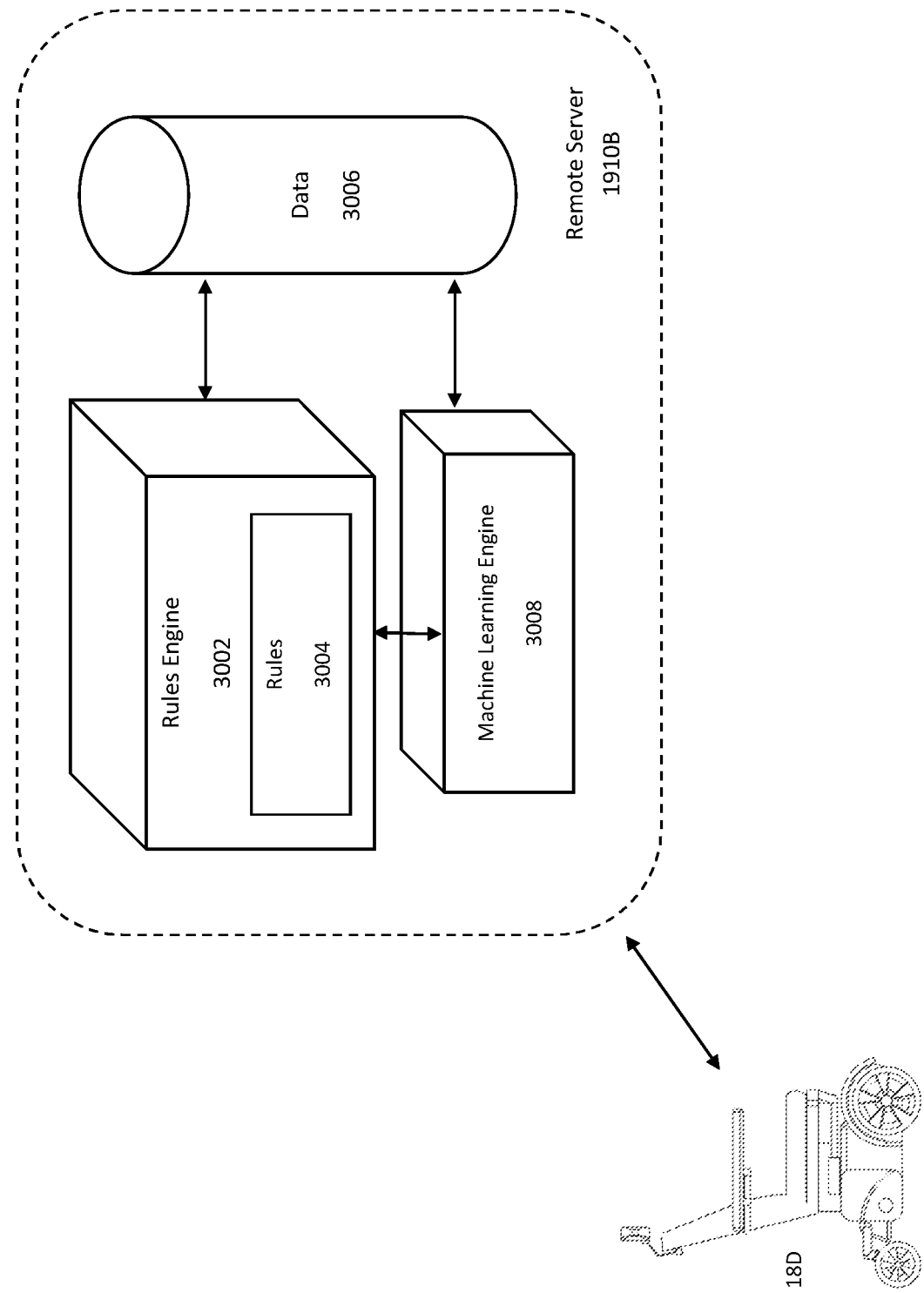
FIG. 30 depicts one or more S-MMSs connected to a remote server.

Adaptive learning (sometimes called machine learning) can be viewed in many ways. One example is using collected data to "inference" a rules engine with subjective probability, or what is known as Bayesian probability. Another example is using collected data to train a neural network or other "AI" machine learning system to identify and react to specific events or conditions. In some embodiments, multiple forms of adaptive or machine learning may be combined on a single remote server instance. FIG. 30 depicts one or more S-MMSs 18D connected to a remote server 1910B. Large sets of data 3006 may be collected by a single S-MMS 18D, additionally data from multiple S-MMSs 18D may be combined and stored on one or more remote servers 1910B. Data 3006 may include how a user operates an S-MMS 18D over time, user health and comfort data, user reaction times, places of use, sensor data, diagnostics, or any other information available to the S-MMS controller 210. This data can then be utilized by rules engines 3002 and machine learning engines 3008 for many purposes.

In some embodiments, a rules engine 3002 is maintained in the secure network remote server 1910B. The rules 3004 in the rules engine 3002 may start out as hard-set rules based on known values or based only on frequency and propensity of some event that is observed and documented. As part of the evolutionary approach of the S-MMS 18D development, future generations will implement the concept of probability as mentioned above; in this case an interpretation of the concept of probability is based on a much richer set of data 3006. Probability may be used to interpret a reasonable expectation representing a state of knowledge or as quantification of belief. This new belief is based on additional available data. For example, users will either improve over time, remain steady state, or lose capability over time. Receiving and logging this data over time, inferencing the data subjectively, and shaping the models against a much richer set of data are possible and inevitable.

In some embodiments, one or more sensors gather data related to the user (e.g. heart rate, respiration rate, galvanic skin response, humidity, etc.). In an example, all user data is normal except for moisture, which is reporting high. In some embodiments, for certain conditions such as traveling through a rain storm, the rules 3004 may be hard-set to ignore this condition. However, in an embodiment, it is noted from other data sources the regional temperature is very high. With this additional data, it is reasonable to interpret this situation against the larger set of data (location and outside temperature) and identify it with potential discomfort. Generally, this is also referred to as Bayesian probability, which belongs to a category of evidential probabilities (evidence based). Over time, these evidence-based probabilities will begin to shape the basic rules and models. This is sometimes referred to as subjective probability. In some embodiments, the rules 3004 of the rules engine 3002 may be used to automate or improve server 1910B functions previously disclosed, such as the conditions under which caregivers are alerted.

Using Onboard Data

In some embodiments, one or more of the rules and machine learning engines (3002 and 3008) may instead be incorporated into the S-MMS controller 210 onboard the S-MMS 18D and processed by an S-MMS processor 802. In this embodiment, data for the machine learning engine may be accessed from onboard memory 320 or remote data 3006 stored on one or more remote servers 1910B.

Regardless of the location of the rules and machine learning engines (3002, 3008) the outputs of the engines may be used to modify, block, or initiate actions by the S-MMS controller 210. In some embodiments, the location capabilities of the S-MMS 18D or paired smart device (e.g. GPS and/or DR) may be used to enforce restrictions on certain users. In this embodiment, a rules engine 3002 monitors S-MMS 18D location as reported by navigation 1216 to the SAC 902. If the current location is outside a predefined area (a rule 3004), then the rules engine 3002 may transmit a message to the S-MMS controller 210 which may, in turn, take an action such as to notify a caregiver or stop the S-MMS 18D from traveling further by transmitting a stop command to the motor controller 604. Assisted living facilities may use this to limit residents from leaving the campus or theme parks may use this to stop EVCs' from leaving a particular park. In such a configuration, a caregiver, technician, and/or administrator may indicate on a map the approved and/or restricted areas for that particular user's profile (as previously disclosed). These zones may be rules-based dependent on criteria such as dates, times, MMS parameters (e.g. one example might be battery charge level), user status (e.g. defined health metrics), and/or other metrics.

In some embodiments rules may be created regardless of location. For example, when it is determined the user can operate in the daylight safely, rules 3004 can be constructed such that at some pre-determined benchmark (as example, lack of mishaps, proficiency at maneuvering in tight or crowded spaces, or some other pre-determined proficiency standard) the user may "graduate" to operating at night or in a crowded urban setting, for example.

To continue the example, with the newly achieved benchmark, the S-MMS 18D comprises lights and/or sensors that aid a user in navigating in dark or dim light, or some other unconventional setting. One or more cameras or light sensors located on a smart device or attached to the S-MMS 18D may be used to determine the amount of ambient light. An example is an application available from Trajkovski Labs that functions as a professional light intensity (lux) meter for a smart device 1502. This application detects the ambient light in terms of lux value and reports the value through the secure connection to the S-MMS controller 210 which includes a rules engine 3002. When it is detected that the environment is dark or dim enough to impede visibility, the S-MMS controller 210 may respond according to preset user preferences or provide the user with a set of options to choose from on the HMI 606. Depending on user or operator preferences (e.g. as listed in a user profile stored in memory 320 of the S-MMS 18 or the remote server 1910), dim/dark light detection may cause one or more automatic systems to be activated by the S-MMS controller 210 to allow for better visibility and/or intelligence about the surroundings. For instance, the S-MMS controller 210 may activate one or more lights that are located on the S-MMS 18, in or around the environment, and/or in smart devices owned by, and in proximity to, the user. As the user gains subdued light experience, the operations the user has successfully completed along with the light levels are logged by the S-MMS controller 210 into the user profile.

In some embodiments, in order to allow for operation in dim light or at night, a user must demonstrate proficiency at daylight navigation. This requirement is intended to provide the user with safety and confidence while operating the S-MMS 18 in low visibility environments. As long as the user continues to operate safely, they are allowed to operate on their own. There is an override function and code that allows a trainer or caregiver to work with the user under supervision.

In a short discussion of later embodiments and how data and models will be handled, the move is made from adaptive systems to predictive systems based on the 1-sigma variances, and reports from disparate sensor sources, along with a level of confidence based on the individual reports from sensors, individual confidences, or variances and how the two variances vary together to yield a covariance.

Some embodiments of the S-MMS include data models that are based on historical data, or based on observations of states of sensors at a finite time, in this case $T_1$. At this time an event is measured, processed, transmitted, and related to other data. This can be done very quickly, e.g. tenths of a second or even seconds. Regardless of delay, it is all historic. Other embodiments of the S-MMS include predictive systems, based on models, multiple models of state, sensors that have known and repeatable characteristics, and known variances as plotted against a standard distribution of measurements. Included in the model are as many elements of error as can be identified, along with the balance as white noise. An embodiment goal may be the sum of all errors, and white noise error cannot be measured equal to 100% system error. An estimator may be used based on the model and sensors used, to make an estimate of state or likelihood of the next report. Next an observation may be made of state (measurement from one or more of the sensors), the measurements may be compared to the prediction, the model can be modified or the "co-variance" of sensors can be used to make a new prediction, and the cycle goes on. With this approach, all of the state predictions are based on a probability of measurement against the models. An important embodiment factor may be that sensor measurements are predicted and then actual measurements from the sensors are taken. By the time system latency catches up, the S-MMS system is still into the future by some amount, and by the time it is presented, it is real-time.

Cloud and Onboard Data Use Example

It is important to note, that this combination of situational awareness with user data (e.g. reaction times, user history, and/or health informatics previously discussed) is expected to allow new types of health and welfare monitoring and optimization. These health and welfare monitoring and optimization processes may be hosted onboard the S-MMS controller 210 and on remote servers 1910 or combinations of the two. It may, in some embodiments, use machine learning such as rules engines 3002 or other types of machine learning engines 3008. As a simple non-limiting example of a predictive system, the S-MMS controller 210 may determine a statistical correlation of slower reaction times and higher stress (perhaps based on electrodermal activity, analysis of images of the user, or analysis of video of the user) when operating along a particular, common route and may offer an alternative route to the user.

As a non-limiting example of what one combination of the disclosed embodiments permits, consider an S-MMS 18 user who may be dealing with intermittent pain. It is known that individuals in pain lose some level of cognitive, and sometime motor, function. Moreover, pain can be a difficult thing to assess, particularly for those individuals who have some level of cognitive impairment. General practice for assessment of pain in cognitively impaired individuals is to combine behavior observations, measurement of physiological factors, and when possible some form of pain self-assessment by the individual. Two of the common behaviors looked for to assess pain are looking for unusual body movements like rocking or fidgeting and looking for changes in activity patterns. Common physiological factors used to help assess pain include increased heart rate, blood pressure, and/or respiratory rate.

An S-MMS 18 configured to recognize pain based on processing sensor reports and other inputs along with rules of a rules engine to determine a likelihood of user pain and then respond to the user pain with a pre-configured output, such as an HMI output or alert, may provide increasing assistance and/or autonomous operation to the user as pain levels increase. When needed, the S-MMS 18 may contact caregiver(s) or medical assistance in a manner previously disclosed, may provide user health data to these individuals, and may even deliver the user to a location for assistance when needed by having the S-MMS controller 210 take operational control of the S-MMS 18 and provide commands to the motor controller 604 based, for example, on the outputs of the SAC 902D drive path manager 1429 or other S-MMS controller components. User health data may include any of the available S-MMS 18 data, including orientation, location, position, distance, time, force, mass, weight, pressure, temperature, image, video, light, resistance, voltage, current, power, raw sensor data, conclusions data, patient measurements, chemical, moisture, electrodermal, bio-electric impedance, galvanic skin resistance, heart rate, pulse, respiratory rate, blood pressure, wetness, pH, salinity, sight, hearing, reaction time, pain status, emotional state, event, state, or action data as appropriate.

Initial pain may be flagged by a rules engine embedded in the user health manager (UHM) 1410 of the SAC 902D, based on a statistical analysis of a combination of factors. In some embodiments, the statistical analysis of factors is based on correlation between increased fidgeting measured by unusual fluctuations in the user weight as measured by the weight tracking system (FIG. 23) (which may fluctuate as a user moves in the chair) and increased heart rate as measured by an onboard joystick monitor (FIG. 22). Based on this correlation, the SAC 902D may flag a possible concern. Based on this concern, the S-MMS controller 210 may connect to and access historical user data which is stored securely on a remote server 1910. This data may be used by machine learning engine 3008 to look for past false alarms or situations that would explain the current readings. Assuming the historical analysis doesn't negate the concern, the S-MMS controller 210 may activate the user-facing camera of the user's paired smart device 1502 and use a secure wireless connection to run images against a facial recognition based emotional state and/or pain monitor machine learning engine 3008 on a remote server 1910 such as Microsoft Azure's Emotion API. The emotional state and/or pain monitor may provide a numerical assessment of pain to the S-MMS controller 210. As the received numerical pain level increases, the UHM 1410 may cause the S-MMS controller 210 to begin ignoring HMI 606 inputs and either stop the S-MMS 18 or instead use drive path manager 1429 and navigation 1216 to drive the S-MMS 18J to a pre-defined safe location. At some threshold, the S-MMS 18 may offer, by the S-MMS controller 210 via the HMI 606, to connect to the users' doctor or caregiver and send a secure packet of real-time data for their analysis using the previously disclosed methods.

Evergreen System: Apps on an Extensible S-MMS

The system architecture disclosed allows for a new, extensible model for MMSs. By allowing the integration of a smart device and allowing deployment of applications to the S-MMS 18 in a secure manner, new technologies can be rapidly, safely deployed to market. As an illustrative example, consider an accessory manufacturer that produces seat cushions for a mobile chair S-MMS 18. If the manufacturer develops a new, smart seating cushion that actively measures shear force on the occupant and adjusts the cushion seat profile to alleviate shear, then they face multiple challenges. They may want to store data and/or provide data to the user in a secure, compliant manner. They may want to use power seat functionality that exists on the S-MMS 18 to assist their active cushion. By using systems of the disclosed S-MMS 18, the cushion manufacturer can be confident that they can integrate to the S-MMS 18 and that data will be handled in a secure, compliant manner. Moreover, they can control S-MMS 18 functions while being confident that they will not interfere with safety critical functions thanks to the API's and separation of hosted applications.

From a technician and/or user standpoint, the ability to purchase a product (such as the example cushion) and go to the S-MMS app store to download the necessary application will make integration of new technologies with their S-MMS 18 less stressful. The S-MMS application may be downloaded on their smart device from the app store and deployed on their smart device, the S-MMS 18, or a combination of the two. Aspects of their unique user profile may be made available to the S-MMS application or an authorized third-party application, and data may be shared with their secure data files. Applications associated with a given user may have the ability to follow the user between S-MMSs as they associate their smart device or profile with a new system.

Integrating Smart Device to HMI

Figure 31:
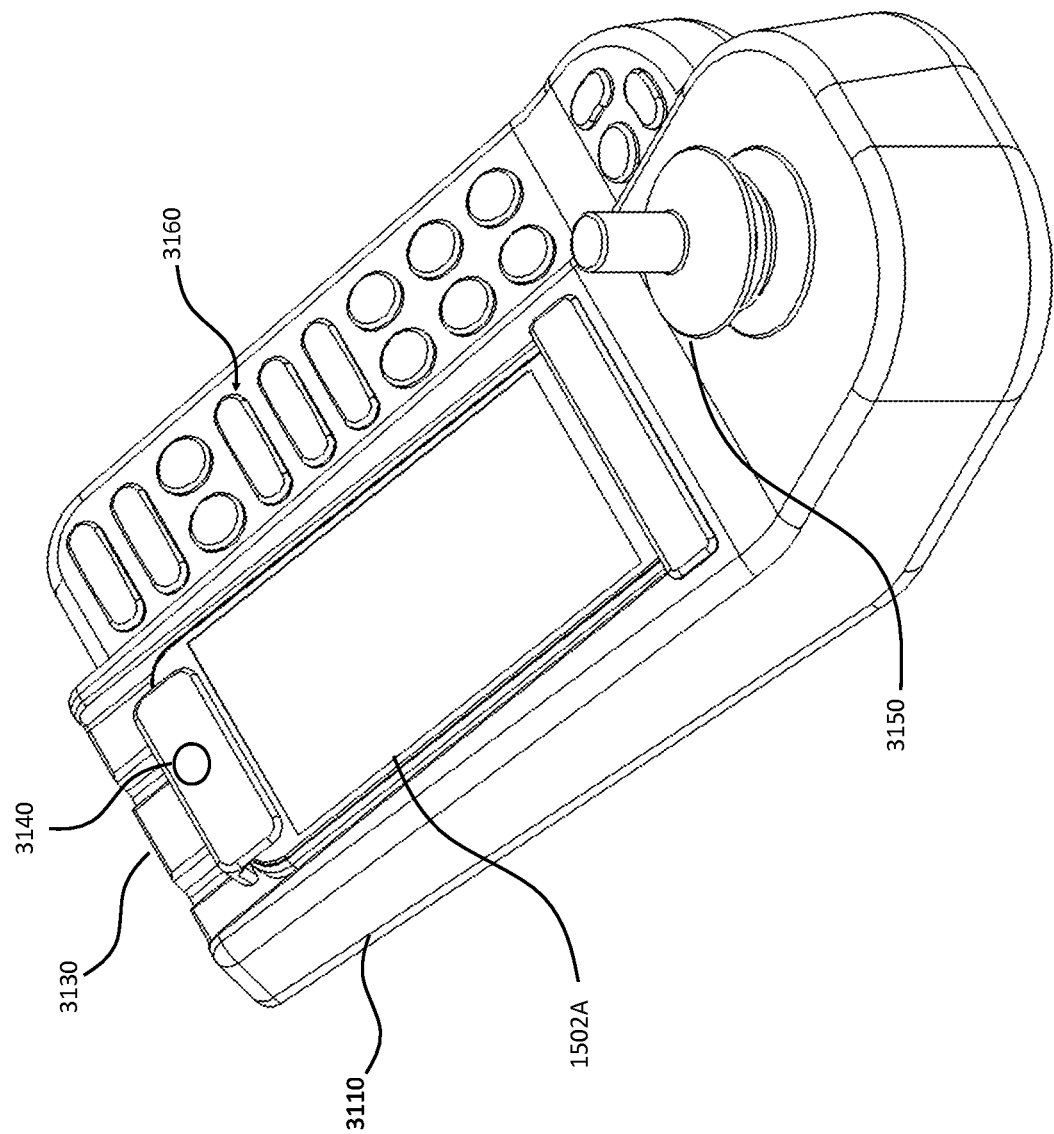
FIG. 31 illustrates an exemplary embodiment of a smart device integrated with an S-MMS user interface.

FIG. 31 illustrates an exemplary embodiment of a smart device 1502A integrated with an S-MMS 18 user interface unit 3110. The user interface unit 3110 may include one or more control features, such as buttons 3160 or other input devices, which control functions of the S-MMS (e.g., power, turn signals), a steering device such as a joystick 3150, and/or a dock 3140 for the paired smart device 1502A. In the depicted embodiment, the smart device 1502A is integral with the S-MMS user interface unit 3110 so that the screen and other features of the smart device can be utilized by the S-MMS 18 for associated display or input functions of the S-MMS 18. The microphone and speaker of the smart device 1502A also may be used for input and output functions of the S-MMS 18. The docking feature 3130 allows removal of the smart device 1502A for use separate from the S-MMS 18 as desired. The dock 3180 may allow virtual/screen buttons, hard buttons, sensor(s), cameras, and other input and/or output devices and communication mediums and protocols of the smart device 1502A to be used by the S-MMS 18 and its associated processes.

Alternative embodiments of a user interface unit for use with a smart device 1502A are envisioned. Examples of these alternative embodiments include:
  Use of a traditional joystick or steering device (such as handle bars in the case of an ATV) with the smart device 1502A held separately.
  Use of the touch interface on the smart device 1502A to steer and control the S-MMS 18 without the need for additional hardware.
  Use of the absolute orientation sensor data of the smart device 1502A to allow control of the S-MMS 18 and steering without the need for additional hardware.
  Use of a capacitive joystick, adhered to the smart device 1502A, to steer the S-MMS 18.
Integration of the smart device 1502A allows unique user feedback and assistance. Several applications include:
  Use of vibration warnings via the smart device 1502A in additionally or alternatively to haptic feedback on the joystick or seat of the S-MMS 18. Vibration warnings may be used to signal a system override of user input, a warning of upcoming unsafe conditions, and/or other events that the user must be notified of or must be confirmed.
  Use of visual alerts, such as pop-up notifications, lights, or screen colors to provide feedback to the user.
  Use of the smart device 1502A as a "heads-up-display" that displays situational awareness information such as a map of threat levels and safe areas around the S-MMS 18.
  Pairing with external cameras and/or using the internal smart device camera to show images, such as live video feeds for driver assistance linked to threat reports. As a non-limiting example, the smart device 1502A might display video from a rear-facing camera on the S-MMS 18 if an obstacle or other object is detected. Additionally or alternatively, the smart device 1502A might display live video from a camera mounted in a room (not on the S-MMS 18) in this situation.
  Additionally, or alternatively, audio warnings and tones may be used to notify the user of actions of the S-MMS 18 and/or request actions of the user.

To facilitate the understanding of the embodiments described herein, a number of terms are defined below. The terms defined herein have meanings as commonly understood by a person of ordinary skill in the relevant art. Terms such as "a," "an," and "the" are not intended to refer to only a singular entity, but rather include the general class of which a specific example may be used for illustration. The terminology herein is used to describe specific embodiments, but their usage does not delimit the disclosure, except as set forth in the claims.

The term "circuit" means at least either a single component or a multiplicity of components, either active and/or passive, that are coupled together to provide a desired function. Terms such as "wire," "wiring," "line," "signal," "conductor," and "bus" may be used to refer to any known structure, construction, arrangement, technique, method, and/or process for physically transferring a signal from one point in a circuit to another. Also, unless indicated otherwise from the context of its use herein, the terms "known," "fixed," "given," "certain", and "predetermined" generally refer to a value, quantity, parameter, constraint, condition, state, process, procedure, method, practice, or combination thereof that is, in theory, variable, but is typically set in advance and not varied thereafter when in use.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment.

Communication between various systems and devices is disclosed herein. Communication may occur using wired and/or wireless communication methods and protocols including, but not limited to, cellular, 802.11, Wi-Fi, 802.15, Bluetooth, 802.20, and WiMAX.

Non-Transitory Computer Readable Medium

The various operations of methods described above may be performed by any suitable means capable of performing the operations, such as various hardware and/or software component(s), circuits, and/or module(s).

The various illustrative logical blocks, modules, and circuits described in connection with the present disclosure may be implemented or performed with a hardware processor, a digital signal processor (DSP), an application specific integrated circuit (ASIC), a field programmable gate array signal (FPGA) or other programmable logic device (PLD), discrete gate or transistor logic, discrete hardware components, or combinations thereof designed to perform the functions described herein. A hardware processor may be a microprocessor, commercially available processor, controller, microcontroller, or state machine. A processor may also be implemented as a combination of two computing components, e.g., a combination of a DSP and a microprocessor, a plurality of microprocessors, one or more microprocessors in conjunction with a DSP core, or any other such configuration.

In one or more aspects, the functions described may be implemented in software, firmware, or any combination thereof executing on a hardware processor. If implemented in software, the functions may be stored as one or more executable instructions or code on a non-transitory computer-readable storage medium. A computer-readable storage media may be any available media that can be accessed by a processor. By way of example, and not limitation, such computer-readable storage media can comprise RAM, ROM, EEPROM, CD-ROM or other optical disk storage, magnetic disk storage or other magnetic storage devices, or any other medium that can be used to store executable instructions or other program code or data structures and that can be accessed by a processor. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Processes or steps described in one implementation can be suitably combined with steps of other described implementations.

Certain aspects of the present disclosure may comprise a computer program product for performing the operations presented herein. For example, such a computer program product may comprise a computer readable storage medium having instructions stored (and/or encoded) thereon, the instructions being executable by one or more processors to perform the operations described herein.

Software or instructions may be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a terminal and/or base station can obtain the various methods upon coupling or providing the storage means to the device.

For the sake of convenience, the operations are described as various interconnected functional blocks or distinct software modules. This is not necessary, however, and there may be cases where these functional blocks or modules are equivalently aggregated into a single logic device, program, or operation with unclear boundaries. In any event, the functional blocks and software modules or described features can be implemented by themselves or in combination with other operations in either hardware or software.

Having described and illustrated the principles of the systems, methods, processes, and/or apparatuses disclosed herein in a preferred embodiment thereof, it should be apparent that the systems, methods, processes, and/or apparatuses may be modified in arrangement and detail without departing from such principles. Claim is made to all modifications and variation coming within the spirit and scope of the following claims.

What is claimed is:

1. A system for a motorized mobile chair comprising:
at least one processor of the motorized mobile chair to:
receive one or more control instructions from a human machine interface (HMI) of the motorized mobile chair, the one or more control instructions transmitted in response to one or more user inputs at the human machine interface;
generate a signal based on the one or more control instructions that causes the motorized mobile chair to respond with a preconfigured response;
receive sensor data from one or more sensors of the motorized mobile chair, the sensor data comprising first data comprising attitude data of the motorized mobile chair and second data generated from one or more sensors associated with one or more characteristics of a user of the motorized mobile chair;
store the sensor data in a first memory associated with the motorized mobile chair, the sensor data comprising the first data comprising the attitude data of the motorized mobile chair and the second data generated from the one or more sensors associated with the one or more characteristics of the user of the motorized mobile chair;
determine a tipping of the motorized mobile chair has occurred based on the attitude data of the motorized mobile chair;
transmit to a remote server at least one of the attitude data of the motorized mobile chair and a communication identifying the tipping of the motorized mobile chair when the at least one processor determines the tipping of the motorized mobile chair has occurred;
receive an authentication key from a device external to the motorized mobile chair;
transmit the authentication key received from the device external to the motorized mobile chair from the motorized mobile chair to the remote server, wherein the authentication key, when authenticated by the remote server, corresponds to a unique user account, and at least some data in the first memory associated with the motorized mobile chair can be associated with the unique user account and stored in a second memory; and
transmit the second sensor data from the motorized mobile chair to the remote server for association with the unique user account and storage in the second memory in association with the unique user account when the authentication key has been authenticated by the remote server.

2. The system of claim 1 wherein:
when the authentication key has been authenticated by the remote server, other data associated with the unique user account may be retrieved from the second memory for transmission to the motorized mobile chair; and
the processor receives the other data and stores the other data in the first memory.

3. The system of claim 1 wherein the processor receives the authentication key from at least one of a third memory on a paired wireless device over a wireless connection, a wearable device, a radio frequency tag identification device, a Bluetooth Low Energy beacon transmitting device, and a memory stick.

4. The system of claim 1 wherein the processor receives the authentication key from a third memory on a paired device over a secure wireless connection.

5. The system of claim 1 wherein the authentication key comprises at least one of a code and a security credential.

6. The system of claim 1 wherein the first memory comprises memory of the motorized mobile chair or memory of a wireless device connected to the motorized mobile chair.

7. The system of claim 1 wherein the second sensor data is stored in a user profile, and the processor transmits the user profile to the remote server for storage.

8. The system of claim 1 wherein the authentication key is received by the processor to enable the processor to access the first memory.

9. The system of claim 1 wherein the authentication key is received by the processor to enable the processor to access a user profile, and the user profile comprises one or more of data about the user, user preferences, and data identifying capabilities of the motorized mobile chair based on the user.

10. The system of claim 1 wherein the authentication key is received by the processor to enable the processor to access a user profile, and the user profile comprises one or more of user reaction time, user preferences, speed limitations of the motorized mobile chair based on the user, drive limitations of the motorized mobile chair based on the user, steering limitations of the motorized mobile chair based on the user, seat position data, sensor calibration data, and human machine interface calibration data.

11. The system of claim 1 wherein the authentication key is received by the processor to enable the processor to access a user profile, and the user profile comprises personal health data.

12. The system of claim 11 wherein the personal health data comprises user data for at least one of medical data, raw sensor data, conclusions data, patient measurements, weight, temperature, heart rate, pulse, respiratory rate, blood pressure, blood glucose level, wetness, sight, hearing, reaction time, pain status, emotional state, orientation, location, event, state, and action.

13. The system of claim 1 wherein the human machine interface comprises at least one of a brain machine interface, a joystick, a touchscreen, a voice command interface, an audio indicator, a tactile surface array, and a sip and puff type array.

14. The system of claim 1 wherein the one or more control instructions each comprise at least one of a calculation, a logical comparison, a change in state, an adjustment of an operating parameter, a limitation of a feature or capability, and an enablement of a feature or capability.

15. The system of claim 1 wherein the control signal comprises at least one of a wired signal and a wireless signal, and wherein the control signal further comprises at least one of a digital signal and an analog signal.

16. The system of claim 1 wherein the preconfigured response comprises at least one of taking operational control, steering, starting, and stopping.

17. The system of claim 1 wherein the first data comprises data of at least one of time, location, orientation, position, distance, temperature, heat, mass, force, pressure, light, resistance, voltage, current, power, video, and images.

18. The system of claim 1 wherein the second data comprises data of at least one of orientation, location, position, distance, time, force, mass, weight, pressure, temperature, image, video, light, resistance, voltage, current, power, medical data, raw sensor data, conclusions data, patient measurements, chemical, moisture, electro-dermal, bio-electric impedance, galvanic skin resistance, heart rate, pulse, respiratory rate, blood pressure, blood glucose level, wetness, sight, hearing, reaction time, pain status, emotional state, event, state, and action.

19. The system of claim 1 wherein the processor communicates using at least one of cellular communications, 802.11 communications, Wi-Fi communications, 802.15 communications, Bluetooth communications, Bluetooth Low Energy communications, radio frequency communications, 802.20 communications, and WiMAX communications.

20. The system of claim 1 wherein the remote server is in a packet network, and the packet network comprises a data transmission network using packet switching.

21. The system of claim 1 wherein the first memory and the second memory each comprises secure memory.

22. The system of claim 1 wherein the processor receives the attitude data of the motorized mobile chair from one or more micro-inertial devices.

23. The system of claim 1 wherein the processor receives the attitude data of the motorized mobile chair from one or more accelerometers.

24. The system of claim 1 wherein the processor receives the attitude data of the motorized mobile chair from at least one of one or more attitude determining sensors, one or more rate determining sensors, and one or more inertia determining sensors.

25. The system of claim 1 wherein the processor generates the signal based on the one or more control instructions and the determined tipping of the motorized mobile chair.

26. The system of claim 1 wherein the processor generates a secure data report regarding the tipping when the processor determines the tipping of the motorized mobile chair has occurred and transmits the secure data report to the remote server as the communication identifying the tipping of the motorized mobile chair.

27. The system of claim 1 further comprising the remote server, wherein the remote server:
receives the at least one of the attitude data and the communication identifying the tipping of the motorized mobile chair; and
in response, transmits an alert to a caregiver device.

28. The system of claim 1 further comprising the remote server, wherein the second memory is associated with the remote server, and the remote server uses the second sensor data by one or more processes of the remote server in association with the unique user account.

29. A system for a motorized mobile chair comprising:
at least one first processor of the motorized mobile chair to:
receive one or more control instructions from a human machine interface (HMI) of the motorized mobile chair, the one or more control instructions transmitted in response to one or more user inputs at the human machine interface;
generate a signal based on the one or more control instructions that causes the motorized mobile chair to respond with a preconfigured response;
receive sensor data from one or more sensors of the motorized mobile chair, the sensor data comprising first data comprising attitude data of the motorized mobile chair and second data generated from one or more sensors associated with one or more characteristics of a user of the motorized mobile chair;
store the sensor data in a first memory associated with the motorized mobile chair, the sensor data comprising the first data comprising the attitude data of the motorized mobile chair and the second data generated from the one or more sensors associated with the one or more characteristics of the user of the motorized mobile chair;
determine a tipping of the motorized mobile chair has occurred based on the attitude data of the motorized mobile chair;
transmit from the motorized mobile chair at least one of the attitude data of the motorized mobile chair and a communication identifying the tipping of the motorized mobile chair when the at least one processor determines the tipping of the motorized mobile chair has occurred;
receive an authentication key from a device external to the motorized mobile chair;
transmit the authentication key received from the device external to the motorized mobile chair from the motorized mobile chair; and
transmit the second sensor data from the motorized mobile chair for association with a unique user account and storage in a second memory in association with the unique user account; and
a remote server comprising at least one second processor to:
receive the at least one of the attitude data of the motorized mobile chair and the communication identifying the tipping of the motorized mobile chair;
receive and authenticate the authentication key, which, when authenticated, corresponds to the unique user account; and
receive the second sensor data from the motorized mobile chair and, when the authentication key has been authenticated, associate the second sensor data from the motorized mobile chair with the unique user account and store the second sensor data in the second memory in association with the unique user account.

30. The system of claim 29 wherein:
when the authentication key has been authenticated by the remote server, the remote server retrieves other data associated with the unique user account from the second memory and transmits the other data to the motorized mobile chair; and
the first processor receives the other data and stores the other data in the first memory.

31. The system of claim 29 wherein the first processor receives the authentication key from at least one of a third memory on a paired wireless device over a wireless connection, a wearable device, a radio frequency tag identification device, a Bluetooth Low Energy beacon transmitting device, and a memory stick.

32. The system of claim 29 wherein the first processor receives the authentication key from a third memory on a paired device over a secure wireless connection.

33. The system of claim 29 wherein the data is stored in a user profile, and the first processor transmits the user profile to the remote server for storage.

34. The system of claim 29 wherein the authentication key is received by the first processor to enable the first processor to access the first memory.

35. The system of claim 29 wherein the authentication key is received by the second processor to enable the second processor to access a user profile, and the user profile comprises one or more of data about the user, user preferences, and data identifying capabilities of the motorized mobile chair based on the user.

36. The system of claim 29 wherein the authentication key is received by the first processor to enable the first processor to access a user profile, and the user profile comprises one or more of user reaction time, user preferences, speed limitations of the motorized mobile chair based on the user, drive limitations of the motorized mobile chair based on the user, steering limitations of the motorized mobile chair based on the user, seat position data, sensor calibration data, and human machine interface calibration data.

37. The system of claim 29 wherein the authentication key is received by the second processor to enable the second processor to access a user profile, and the user profile comprises personal health data.

38. The system of claim 29 wherein the remote server is in a packet network, and the packet network comprises a data transmission network using packet switching.

39. The system of claim 29 wherein the first processor receives the attitude data of the motorized mobile chair from one or more micro-inertial devices.

40. The system of claim 29 wherein the first processor receives the attitude data of the motorized mobile chair from one or more accelerometers.

41. The system of claim 29 wherein the first processor receives the attitude data of the motorized mobile chair from at least one of one or more attitude determining sensors, one or more rate determining sensors, and one or more inertia determining sensors.

42. The system of claim 29 wherein the first processor generates the signal based on the one or more control instructions and the determined tipping of the motorized mobile chair.

43. The system of claim 29 wherein the first processor generates a secure data report regarding the tipping when the first processor determines the tipping of the motorized mobile chair has occurred and transmits the secure data report to the remote server as the communication identifying the tipping of the motorized mobile chair.

44. The system of claim 29 wherein the second processor:
receives the at least one of the attitude data and the communication identifying the tipping of the motorized mobile chair; and
in response, transmits an alert to a caregiver device.

45. The system of claim 29 wherein the second memory is associated with the remote server, and the second processor of the remote server uses the second sensor data by one or more processes of the remote server in association with the unique user account.

46. A method for a motorized mobile chair comprising:
receiving, by a processor of the motorized mobile chair, one or more control instructions from a human machine interface (HMI) of the motorized mobile chair, the one or more control instructions transmitted in response to one or more user inputs at the human machine interface;
generating a signal based on the one or more control instructions that causes the motorized mobile chair to respond with a preconfigured response;
receiving, by the processor, sensor data from one or more sensors of the motorized mobile chair, the sensor data comprising first data comprising attitude data of the motorized mobile chair and second data generated from one or more sensors associated with one or more characteristics of a user of the motorized mobile chair;

storing, by the processor, the sensor data in a first memory associated with the motorized mobile chair, the sensor data comprising the first data comprising the attitude data of the motorized mobile chair and the second data generated from the one or more sensors associated with the one or more characteristics of the user of the motorized mobile chair;

determining, by the processor, a tipping of the motorized mobile chair has occurred based on the attitude data of the motorized mobile chair;

transmitting, by the processor to a remote server, at least one of the attitude data of the motorized mobile chair and a communication identifying the tipping of the motorized mobile chair when the processor determines the tipping of the motorized mobile chair has occurred;

receiving an authentication key from a device external to the motorized mobile chair;

transmitting the authentication key received from the device external to the motorized mobile chair from the processor to the remote server, wherein the authentication key, when authenticated by the remote server, corresponds to a unique user account, and at least some data in the first memory associated with the motorized mobile chair can be associated with the unique user account and stored in a second memory; and transmitting the second sensor data from the processor to the remote server for association with the unique user account and storage in the second memory in association with the unique user account when the authentication key has been authenticated by the remote server.

47. The method of claim 46 wherein:
when the authentication key has been authenticated by the remote server, other data associated with the unique user account may be retrieved from the second memory for transmission to the motorized mobile chair; and
the processor receives the other data and stores the other data in the first memory.

48. The method of claim 46 wherein the processor receives the authentication key from at least one of a third memory on a paired wireless device over a wireless connection, a wearable device, a radio frequency tag identification device, a Bluetooth Low Energy beacon transmitting device, and a memory stick.

49. The method of claim 46 wherein the processor receives the authentication key from a third memory on a paired device over a secure wireless connection.

50. The method of claim 46 wherein the second sensor data is stored in a user profile, and the processor transmits the user profile to the remote server for storage.

51. The method of claim 46 wherein the authentication key is received by the processor to enable the processor to access the first memory.

52. The method of claim 46 wherein the authentication key is received by the processor to enable the processor to access a user profile, and the user profile comprises one or more of data about the user, user preferences, and data identifying capabilities of the motorized mobile chair based on the user.

53. The method of claim 46 wherein the authentication key is received by the processor to enable the processor to access a user profile, and the user profile comprises one or more of user reaction time, user preferences, speed limitations of the motorized mobile chair based on the user, drive limitations of the motorized mobile chair based on the user, steering limitations of the motorized mobile chair based on the user, seat position data, sensor calibration data, and human machine interface calibration data.

54. The method of claim 46 wherein the authentication key is received by the processor to enable the processor to access a user profile, and the user profile comprises personal health data.

55. The method of claim 46 wherein the processor receives the attitude data of the motorized mobile chair from one or more micro-inertial devices.

56. The method of claim 46 wherein the processor receives the attitude data of the motorized mobile chair from one or more accelerometers.

57. The method of claim 46 wherein the processor receives the attitude data of the motorized mobile chair from at least one of one or more attitude determining sensors, one or more rate determining sensors, and one or more inertia determining sensors.

58. The method of claim 46 wherein the processor generates the signal based on the one or more control instructions and the determined tipping of the motorized mobile chair.

59. The method of claim 46 wherein the processor generates a secure data report regarding the tipping when the processor determines the tipping of the motorized mobile chair has occurred and transmits the secure data report to the remote server as the communication identifying the tipping of the motorized mobile chair.

60. The method of claim 46 wherein:
the remote server receives the at least one of the attitude data and the communication identifying the tipping of the motorized mobile chair; and
in response, the remote server transmits an alert to a caregiver device.

61. The method of claim 46 wherein the second memory is associated with the remote server, and the method further comprises processing the second sensor data by one or more processes of the remote server in association with the unique user account.

62. A method for a motorized mobile chair comprising:
receiving one or more control instructions from a human machine interface (HMI) of the motorized mobile chair by at least one first processor of the motorized mobile chair, the one or more control instructions transmitted in response to one or more user inputs at the human machine interface;
generating a signal based on the one or more control instructions that causes the motorized mobile chair to respond with a preconfigured response;
receiving sensor data by the first processor from one or more sensors of the motorized mobile chair, the sensor data comprising first data comprising attitude data of the motorized mobile chair and second data generated from one or more sensors associated with one or more characteristics of a user of the motorized mobile chair;
storing the sensor data in a first memory associated with the motorized mobile chair by the first processor, the sensor data comprising the first data comprising the attitude data of the motorized mobile chair and the second data generated from the one or more sensors associated with the one or more characteristics of the user of the motorized mobile chair;
determining a tipping of the motorized mobile chair has occurred based on the attitude data of the motorized mobile chair;
transmitting, from the motorized mobile chair, at least one of the attitude data of the motorized mobile chair and a communication identifying the tipping of the motorized mobile chair;

receiving an authentication key from a device external to the motorized mobile chair;

transmitting the authentication key received from the device external to the motorized mobile chair by the first processor;

transmitting, by the first processor, the sensor data for association with a unique user account and storage in a second memory in association with the unique user account;

receiving, by a remote server, the at least one of the attitude data of the motorized mobile chair and the communication identifying the tipping of the motorized mobile chair, the remote server comprising a second processor;

receiving the authentication key by the remote server, which, when authenticated, corresponds to the unique user account; and receiving the second sensor data from the motorized mobile chair by the remote server and, when the authentication key has been authenticated by the remote server, associating the second sensor data from the motorized mobile chair with the unique user account and storing the second sensor data in the second memory in association with the unique user account.

63. The method of claim 62 wherein:

when the authentication key has been authenticated by the remote server, the remote server retrieves other data associated with the unique user account from the second memory for transmission to the motorized mobile chair; and the first processor receives the other data and stores the other data in the first memory.

64. The method of claim 62 wherein the first processor receives the authentication key from at least one of a third memory on a paired wireless device over a wireless connection, a wearable device, a radio frequency tag identification device, a Bluetooth Low Energy beacon transmitting device, and a memory stick.

65. The method of claim 62 wherein the first processor receives the authentication key from a third memory on a paired device over a secure wireless connection.

66. The method of claim 62 wherein the data is stored in a user profile, and the first processor transmits the user profile to the remote server for storage.

67. The method of claim 62 wherein the authentication key is received by the first processor to enable the first processor to access the first memory.

68. The method of claim 62 wherein the authentication key is received by the second processor to enable the second processor to access a user profile, and the user profile comprises one or more of data about the user, user preferences, and data identifying capabilities of the motorized mobile chair based on the user.

69. The method of claim 62 wherein the authentication key is received by the first processor to enable the first processor to access a user profile, and the user profile comprises one or more of user reaction time, user preferences, speed limitations of the motorized mobile chair based on the user, drive limitations of the motorized mobile chair based on the user, steering limitations of the motorized mobile chair based on the user, seat position data, sensor calibration data, and human machine interface calibration data.

70. The method of claim 62 wherein the authentication key is received by the second processor to enable the second processor to access a user profile, and the user profile comprises personal health data.

71. The method of claim 62 wherein the first processor receives the attitude data of the motorized mobile chair from one or more micro-inertial devices.

72. The method of claim 62 wherein the first processor receives the attitude data of the motorized mobile chair from one or more accelerometers.

73. The method of claim 62 wherein the first processor receives the attitude data of the motorized mobile chair from at least one of one or more attitude determining sensors, one or more rate determining sensors, and one or more inertia determining sensors.

74. The method of claim 62 wherein the first processor generates the signal based on the one or more control instructions and the determined tipping of the motorized mobile chair.

75. The method of claim 62 wherein the first processor generates a secure data report regarding the tipping when the first processor determines the tipping of the motorized mobile chair has occurred and transmits the secure data report to the remote server as the communication identifying the tipping of the motorized mobile chair.

76. The method of claim 62 wherein:

the remote server receives the at least one of the attitude data and the communication identifying the tipping of the motorized mobile chair; and in response, the remote server transmits an alert to a caregiver device.

77. The method of claim 62 wherein the second memory is associated with the remote server, and the method further comprises processing the second sensor data by one or more processes of the remote server in association with the unique user account.

* * * * *